US005849553A

United States Patent [19]
Anderson et al.

[11] Patent Number: 5,849,553
[45] Date of Patent: *Dec. 15, 1998

[54] MAMMALIAN MULTIPOTENT NEURAL STEM CELLS

[75] Inventors: David J. Anderson, Altadena, Calif.; Derek L. Stemple, Newton, Mass.

[73] Assignee: California Institute of Technology, Pasadena, Calif.

[*] Notice: The term of this patent shall not extend beyond the expiration date of Pat. No. 5,629,159.

[21] Appl. No.: 485,612

[22] Filed: Jun. 7, 1995

Related U.S. Application Data

[63] Continuation-in-part of Ser. No. 188,286, Jan. 28, 1994, Pat. No. 5,654,183, which is a continuation-in-part of Ser. No. 969,088, Oct. 29, 1992, abandoned, which is a continuation-in-part of Ser. No. 920,617, Jul. 27, 1992, abandoned.

[51] Int. Cl.$^6$ ............................. C12N 15/85; C12N 15/09
[52] U.S. Cl. .................. 435/172.3; 435/69.1; 435/320.1; 435/325; 435/353
[58] Field of Search ................................ 435/69.1, 172.3, 435/320.1, 325, 353

[56] References Cited

U.S. PATENT DOCUMENTS

| | | | |
|---|---|---|---|
| 4,705,751 | 11/1987 | Mosher | 435/70.4 |
| 4,707,448 | 11/1987 | Major | 435/240.25 |
| 5,061,620 | 10/1991 | Tsukamota et al. | 435/7.21 |
| 5,087,570 | 2/1992 | Weissman et al. | 435/240.1 |

FOREIGN PATENT DOCUMENTS

| | | |
|---|---|---|
| 89 03872 | 5/1989 | WIPO . |
| 93 01275 | 1/1993 | WIPO . |
| 94 09119 | 4/1994 | WIPO . |
| 94 10292 | 5/1994 | WIPO . |

OTHER PUBLICATIONS

Orkin et al. 1995 "Report and Recommendations of the Panel to assess the NIH Investment in Research on Gene Therapy".

Lo, L.–C., et al., "V–myc Immortalization of Early Rat Neural Crest Cells Yields a Clonal Cell Line Which Generates Both Glial and Adrenergic Progenitor Cells." *Developmental Biology*, 145:139–153 (1991).

Stemple, D.L., et al., "A Schwann Cell Antigen Recognized by Monoclonal Antibody 217c is the Rat Low–Affinity Nerve Growth Factor Receptor." *Neuroscience Letters*, 124:57–60 (1991).

Murphy, M., et al., "Generation of Sensory Neurons is Stimulated by Leukemia Inhibitory Factor." *Proc. Natl. Acad. Sci. USA*, 88:3498–3501 (1991).

Perris, R., et al., "Local Embryonic Matrices Determine Region–Specific Phenotypes in Neural Crest Cells." *Science* 241:86–89 (1988).

Morrison–Graham, K., et al., "Extracellular Matrix from Normal but Not Steel Mutant Mice Enhances Melanogenesis in Cultured Mouse Neural Crest Cells." *Developmental Biology* 139:299–307 (1990).

Boisseau, S., et al., "Mammalian Neuronal Differentiation: Early Expression of a Neuronal Phenotype from Mouse Neural Crest Cells in a Chemically Defined Culture Medium." *Development* 106:665–674 (1989).

Smith–Thomas, L.C., et al., "Expression of Schwann Cell Markers by Mammalian Neural Crest Cells in vitro" *Development* 105:251–262 (1989).

Deville, F.S.S.C., et al., "Developmental Potentialities of Cells Derived from the Truncal Neural Crest in Clonal Cultures." *Developmental Brain Research* 66:1–10 (1992).

Baroffio, A., et al., "Common Precursors for Neural and Mesectodermal Derivatives in the Cephalic Neural Crest." *Development* 112:301–305 (1991).

Baroffio, A., et al., "Clone–Forming Ability and Differentiation Potential of Migratory Neural Crest Cells." *Proc. Natl. Acad. Sci. USA* 85:5325–5329 (1988).

Dupin, E., et al., "Schwann–Cell Differentiation in Clonal Cultures of the Neural Crest, as Evidenced by the Anti–Schwann Cell Myelin Protein Monoclonal Antibody." *Proc. Natl. Acad. Sci. USA* 87:1119–1123 (1990).

Cohen, A.M., et al., "A Clonal Approach to the Problem of Neural Crest Determination." *Developmental Biology* 46:262–280 (1975).

Sieber–Blum, M., et al., "Clonal Analysis of Quail Neural Crest Cells: They Are Pluripotent and Differentiate in Vitro in the Absence of Noncrest Cells." *Developmental Biology* 80:96–106 (1980).

Duff, R.S., et al., "In Vitro Clonal Analysis of Progenitor Cell Patterns in Dorsal Root and Sympathetic Ganglia of the Quail Embryo." *Developmental Biology* 147:451–459 (1990).

Bronner–Fraser, M., et al., "Developmental bPotential of Avian Trunk Neural Crest Cells In Situ." *Neuron* 3:755–766 (1989).

(List continued on next page.)

*Primary Examiner*—John I. LeGuyader
*Attorney, Agent, or Firm*—Flehr Hohbach Test Albritton & Herbert LLP; Richard F. Trecartin; Robin M. Silva

[57] ABSTRACT

The invention includes mammalian multipotent neural stem cells and their progeny and methods for the isolation and clonal propagation of such cells. At the clonal level the stem cells are capable of self regeneration and asymmetrical division. Lineage restriction is demonstrated within developing clones which are sensitive to the local environment. The invention also includes such cells which are transfected with foreign nucleic acid, e.g., to produce an immortalized neural stem cell, and immortalized cell lines which are capable of subsequent disimmortalization. The invention further includes transplantation assays which allow for the identification of mammalian multipotent neural stem cells from various tissues and methods for transplanting mammalian neural stem cells and/or neural or glial progenitors into mammals. A novel method for detecting antibodies to neural cell surface markers is disclosed as well as a monoclonal antibody to mouse LNGFR.

25 Claims, 44 Drawing Sheets

OTHER PUBLICATIONS

Bronner–Fraser, M., et al., "Cell Lineage Analysis Reveals Multipotency of Some Avian Neural Crest Cells." *Nature* 355:161–164 (1988).

Fraser, S.E., et al., "Migrating Neural Crest Cells in the Trunk of the Avian Embryo are Multipotent." *Development* 112:913–920 (1991).

Frank, E., et al., "Lineage of Neurons and Glia in Chick Dorsal Root Ganglia: Analysis in vivo with a Recombinant Retrovirus." *Development* 111:895–907 (1991).

Le Douarin, N.M., "Cell Line Segregation During Peripheral Nervous System Ontogeny." *Science* 231:1515–1522 (1986).

Gorham, J.D., et al., "The Expression of the Neuronal Intermediate Filament Protein Peripherin in the Rat Embryo." *Developmental Brain Research* 57:235–248 (1990).

Portier, M.M., et al., "Regulation of Peripherin in Mouse Neuroblastoma and Rat PC 12 Pheochroomocytoma Cell Lines." *Dev. Neurosci.* 6:215–266 (1983/84).

Portier, M.M., et al., "Peripherin, a New Member of the Intermediate Filament Protein Family." *Dev. Neurosci.* 6:336–344 (1983/84).

Parysek, L.M., et al., "Distribution of a Novel 57 kDa Intermediate Filament (IF) Protein in the Nervous System." *The Journal of Neuroscience* 8:555:563 (1988).

Parysek, L.M., et al., "A Type III Intermediate Filament Gene Is Expressed in Mature Neurons." *Neuron* 1:395–401 (1988).

Anderson, D.J., et al., "A Biopotential Neuroendocrine Precursor Whose Choice of Cell Fate is Determined by NGF and Glucocorticoids." *Cell* 47:1079–1090 (1986).

Birren, S.J., et al., "A v–myc–Immortalized Sympathoadrenal Progenitor Cell Line in Which Neuronal Differentiation is Initiated by FGF but Not NGF." *Neuron* 4:189–201 (1990).

Potten, C.S., et al., "Stem Cells: Attributes, Cycles, Spirals, Pitfalls and Uncertainties Lessons for and From the Crypt." *Development* 110:1001–1020 (1990).

Hall, P.a., et al., "Stem Cells: The Generation and Maintenance of Cellular Diversity." *Development* 106:619–633 (1989).

Raff, M.C., et al., "A Glial Progenitor Cell that Develops in vitro into an Astrocyte or an Oligodendrocyte Depending on Culture Medium." *Nature* 303:390–396 (1983).

Jessen, K.R., et al., "Three Markers of Adult Non–Myelin––Forming Schwann Cells, 217c(Ran–1), A5E3 and GFAP: Development and Regulation by Neuron–Schwann Cell Interactions." *Development* 109:91–103 (1990).

Reynolds, B.A., et al., "Generation of Neurons and Astrocytes from Isolated Cells of the Adult Mammalian Central Nervious System." *Science* 255:1707–1710 (1992).

Porter, S., et al., "Schwann Cells Stimulated to Proliferate in the Absence of Neurons Retain Full Functional Capability." *The Journal of Neuroscience* 6:3070–3078 (1986).

Brockes, J.P., et al., "Studies on Cultured Rat Schwann Cells. I. Establishment of Purified Populations from Cultures of Peripheral Nerve." *Brain Research* 165:105–118 (1979).

Huzar, D., et al., "Migration and Proliferation of Cultured Neural Crest Cells in W Mutant Neural Crest Chimeras." *Development* 112:131–141 (1991).

Anderson, D.J., "The Neural Crest Cell Lineage Problem: Neuropoiesis." *Neuron* 3:1–12 (1989).

Dodd, J., et al., "Spatial Regulation of Axonal Glycoprotein Expression on Subsets of Embryonic Spinal Neurons." *Neuron* 1:105–116 (1988).

Ross, A.H., et al., "Characterization of Nerve Growth Factor REceptor in Neural Crest Tumors Using Monoclonal Antibodies." *Proc. Natl. Acad. Sci. USA* 81:6681–6685 (1984).

Johnson, D., et al., "Expression and Structure of the Human NGF Receptor." *Cell* 47:545–554 (1986).

Chandler, C.E., et al., "A Monoclonal Antibody Modulates the Interaction Nerve Growth Factor with PC12 Cells." *The Journal of Biological Chemistry* 259:6882–6889 (1984).

Chao, M.V., et al., "Gene Transfer and Molecular Cloning of the Human NGF Receptor." *Science* 232:518–521 (1986).

Radeke, M.J., et al., "Gene Transfer and Molecular Cloning of the Rat Nerve Growth Factor Receptor." *Nature* 325:593–597 (1987).

Weskanp, G., et al., "Evidence that Biological Activity of NGF is Mediated through a Novel Subclass of High Affinity Receptors." *Neuron* 6:649–663 (1991).

Lendahl, U., et al., "CNS Stem Cells Express a New Class of Intermediate Filament Protein." *Cell* 60:585–595 (1990).

Hockfield, S., et al., "Identificateion of Major Cell Classes in teh Developing Mammalian Nervous System." *The Journal of Neuroscience* 5:3310–3328 (1985).

Friedman, B., et al., "Monoclonal Antibody Rat 401 Recognizes Schwann Cells in Mature and Developing Peripheral Nerve." *The Journal of Comparative Neurology* 295:43–51 (1990).

Stemple, D., et al., "Isolation of a Stem Cell for Neurons and Glia from the Mammalian Neural Crest." *Cell* 71:973–985 (1992).

Reynolds, B.A., et al., "EGF–and TGFα–Responsive Striatal Embryonic Progenitor Cells Produce Both Neurons and Astrocytes." *Soc. Neurosc. Abst.* 15–1147 (1990).

Reynolds, B.A., et al., "A Non–Transformed, Growth Factor–Dependent Stem Cell Line Derived from the Embryonic Mouse CNS Produces Neurons, Astrocytes and Oligodendrocytes." *Current Contents/Life Sciences, Excerpta Medica (EMBASE) and Neuroscience Abstracts* 4(3) :208 (1992).

Bartlett, P.F., et al., "Immortalization of mouse neural precursor cells by teh c–myc oncogene" *Proc. Natl. Acad. Sci. USA* 85:3255–3259 (1988).

Bernard, O., et al., "Role of the c–myc and the N–myc Proto–Oncogenes in the Immortalization of Neural Precursors." *Journal of Neuroscience Research* 24:9–10 (1989).

Murphy, M., et al., "Cell Lines Derived from Mouse Neural Crest are Representative of Cells at Various Stages of Differentiation" *Journal of Neurobiology* 22(5):522–535 (1991).

Shah, N.M., et al., "Glial Growth Factor Restricts Mammalian Neural Crest Stem Cells to a Glial Fate." No. 005 Article, 11 page (1994).

Wigler, et al. *Proc. Natl. Acad. Sci. USA* 76:1373–1376 (1979).

Johnson, et al. *Proc. Natl. Acad. Sci. USA* 89:3596–3600 (1992).

Ito, K., et al., "Pluripotent and Developmentally Restricted Neural–Crest–Derived Cells in Posterior Visceral Arches." *Developmental Biology* 156:191–200 (1993).

Voscori et al., *Soc. Neurosic. Abstr.* 20: (page number and Abstract number are not legible) (1994).

Voscori et al., *Soc. Neurosci. Abstr.* 19:971 (1993).

Silani, V., et al., "NGF–Response of EGF–Dependent Progenitor Cells Obtained from Human Sympathetic Ganglia." *Neuroreport* 5(16) :2085–2089 (1994).

Bannerman, P.G., et al., "Protein Growth Factor Requirements of Rat Neural Crest Cells." *J. Neurosci. Res.* 36:46–57 (1993).

GIBCO–BRL Catalog (1992) pp. 1 and 121.

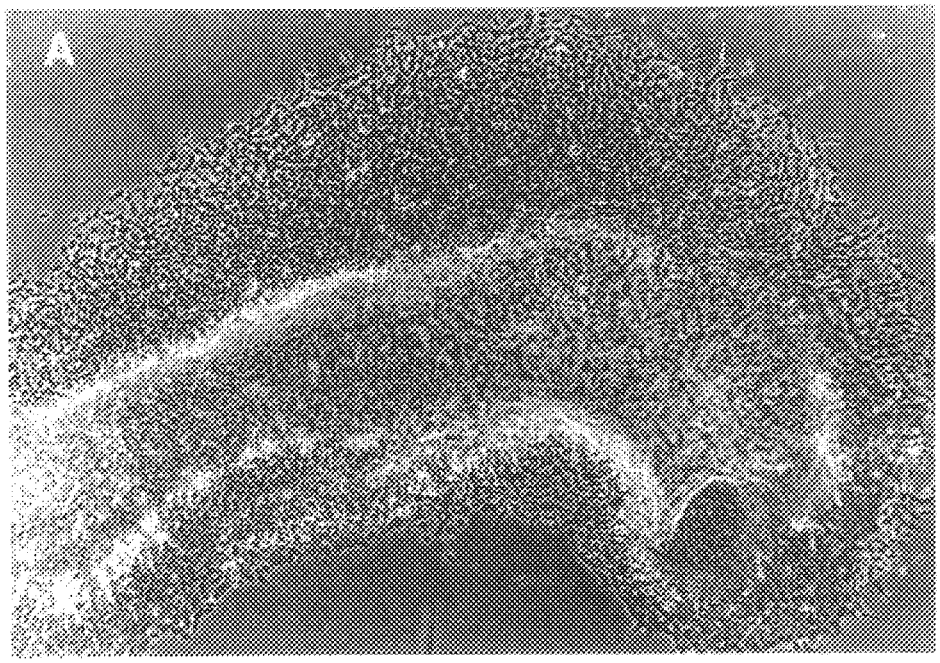
FIG._1A
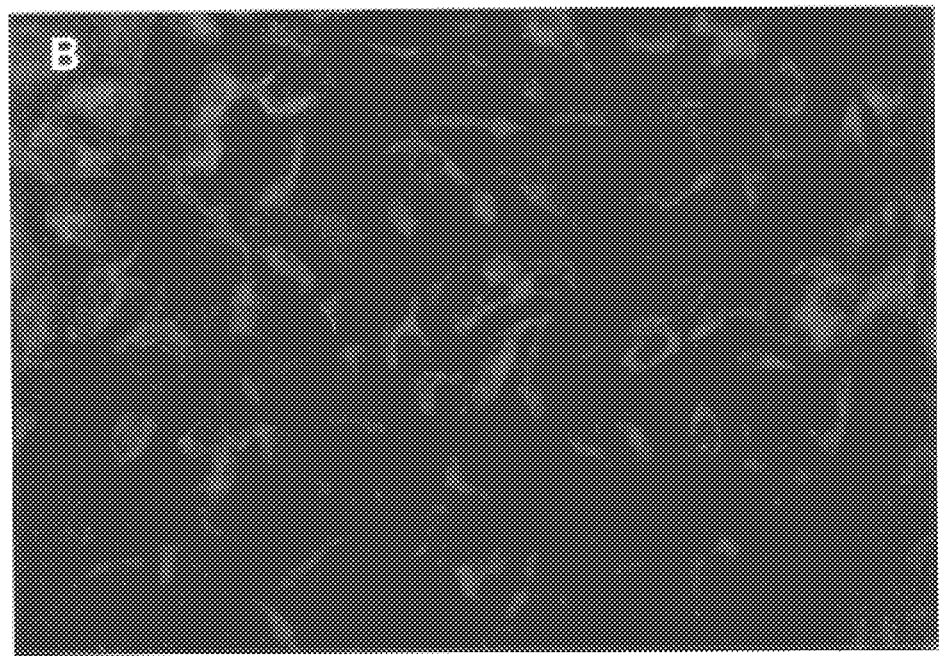
FIG._1B

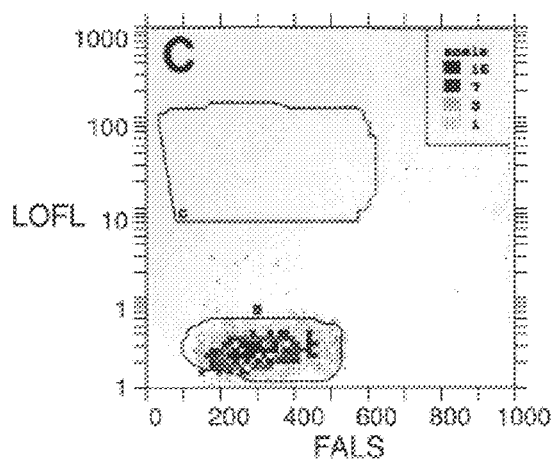 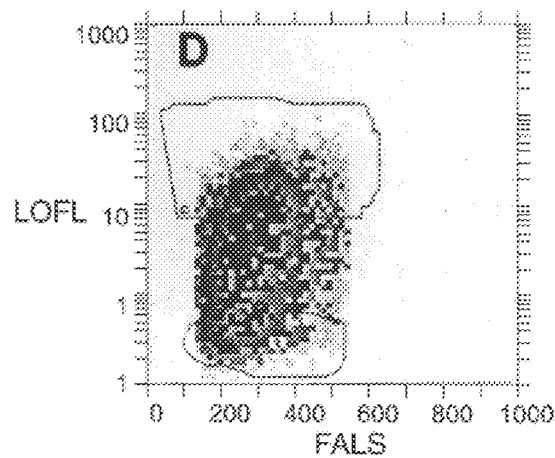
FIG._1C    FIG._1D

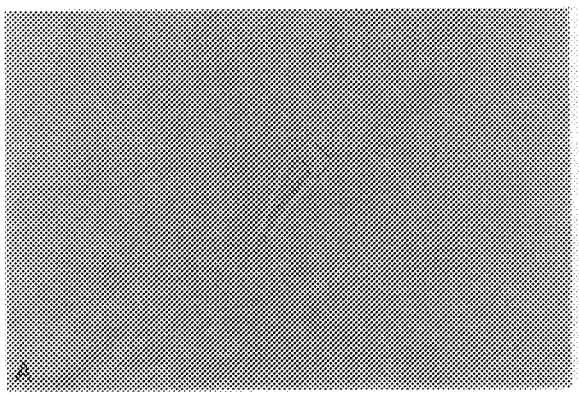
FIG._2A
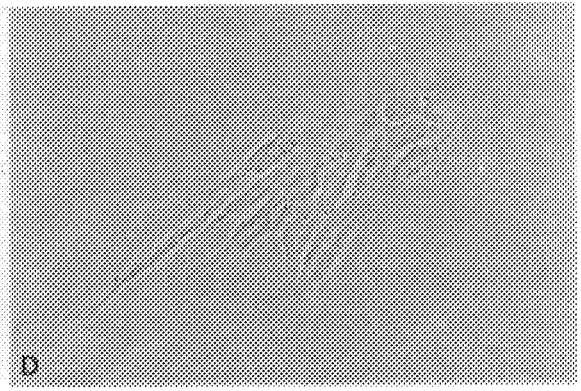
FIG._2D
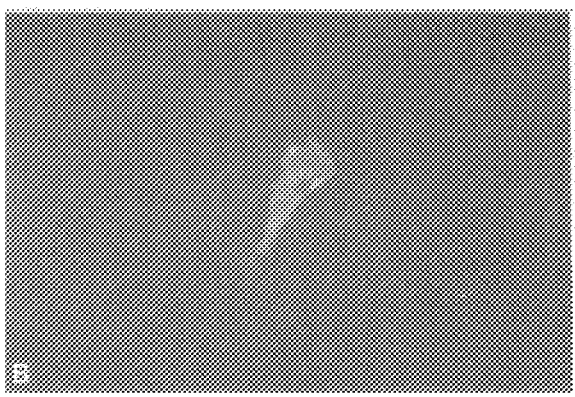
FIG._2B
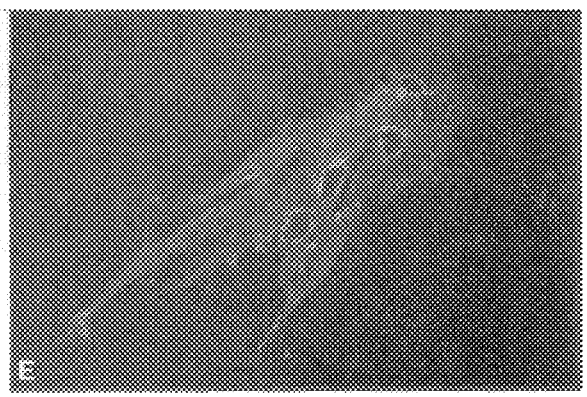
FIG._2E
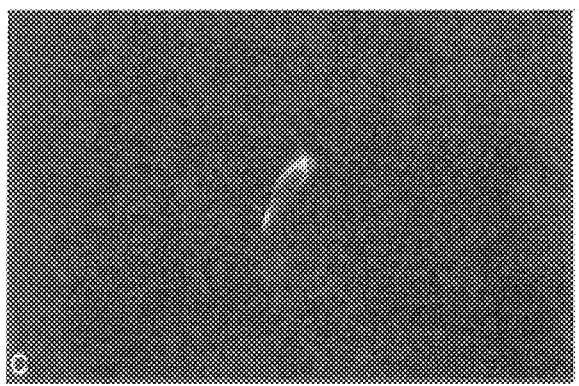
FIG._2C
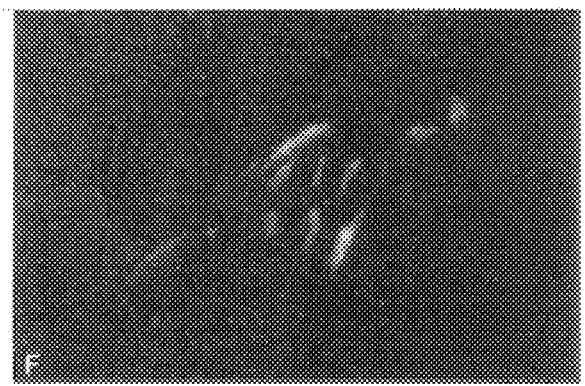
FIG._2F

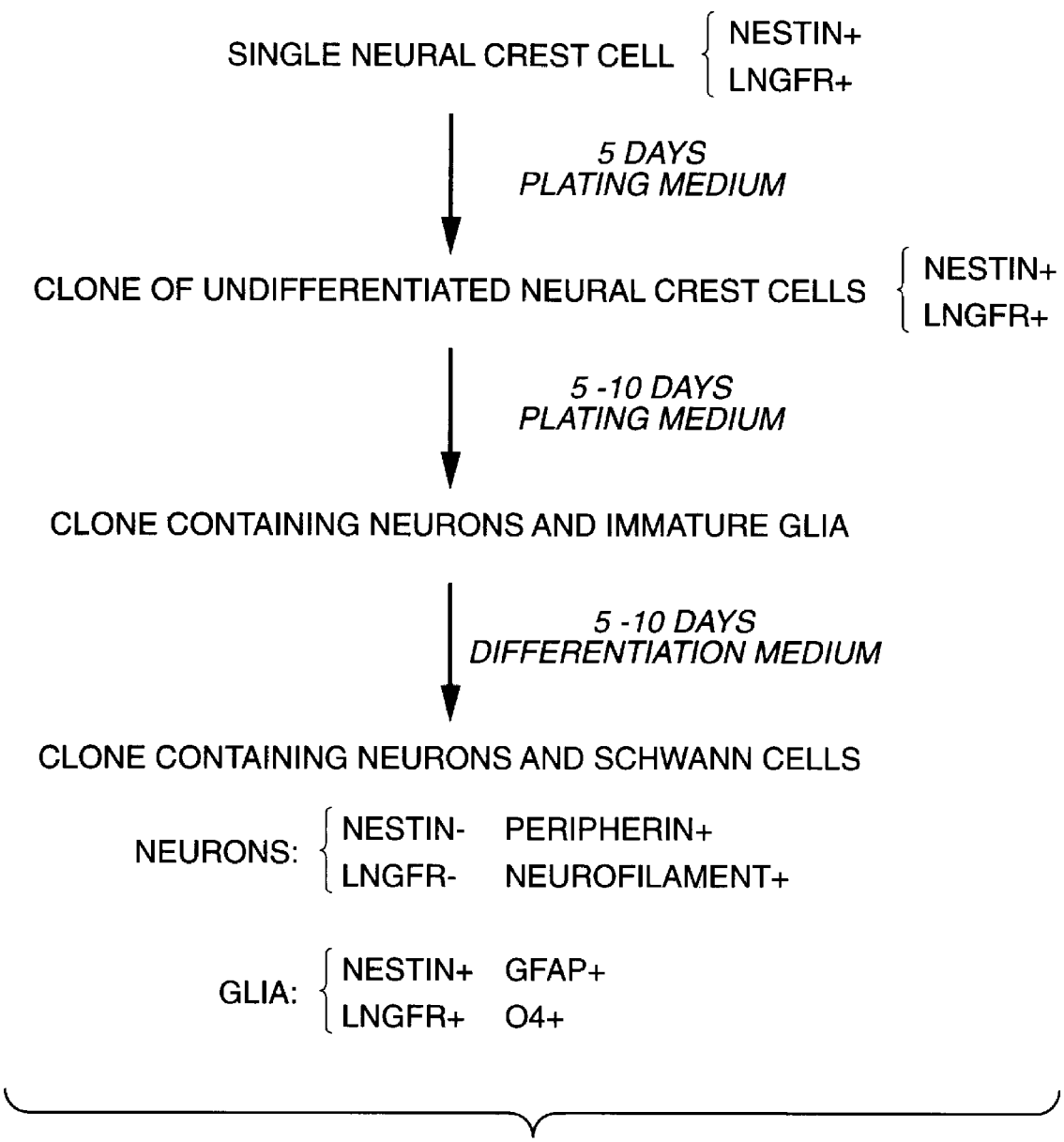
FIG._3

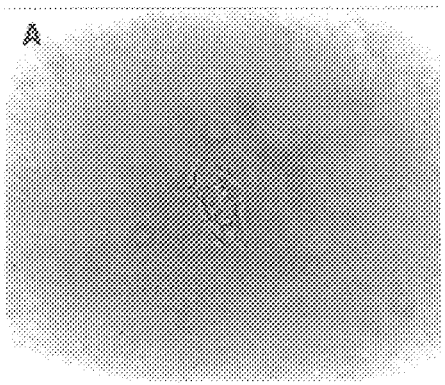
FIG._4A
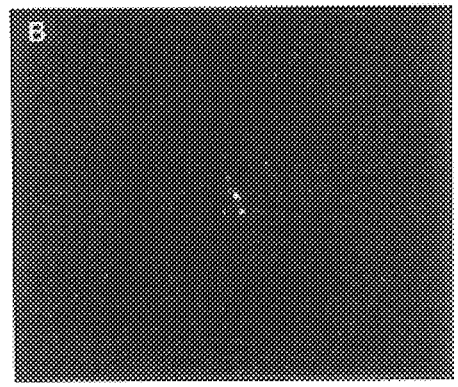
FIG._4B
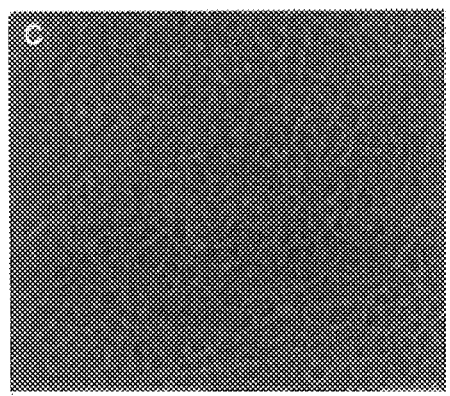
FIG._4C
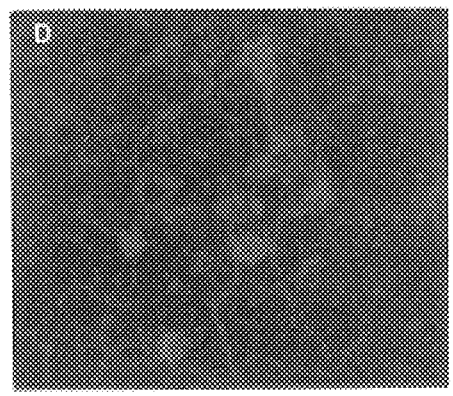
FIG._4D
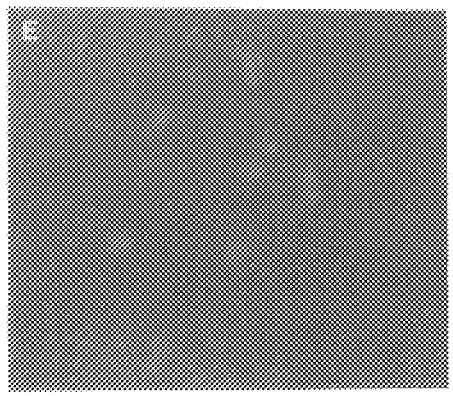
FIG._4E
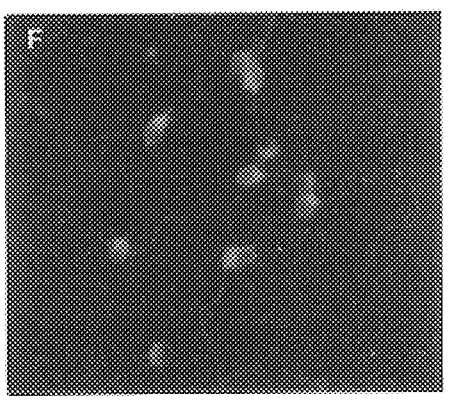
FIG._4F

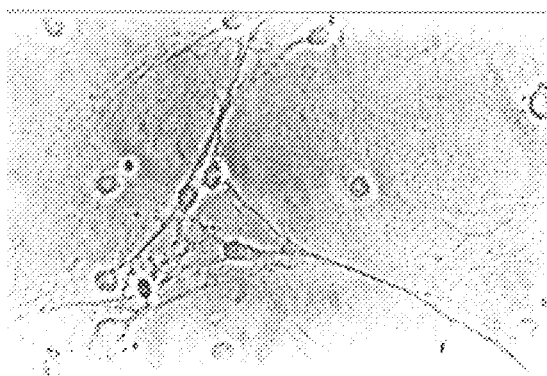
FIG._5A
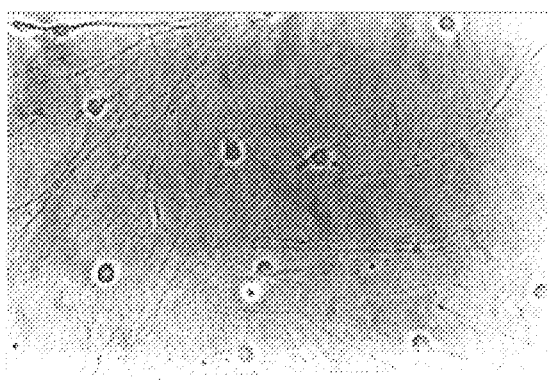
FIG._5D
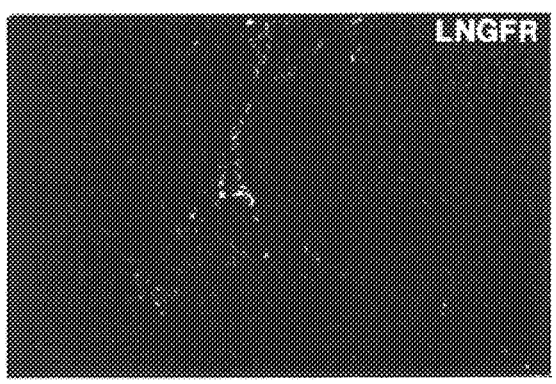
FIG._5B
FIG._5E
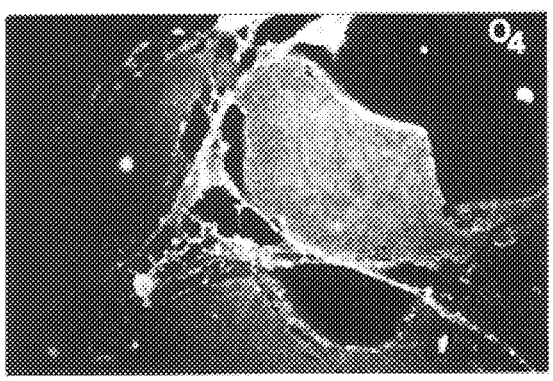
FIG._5C
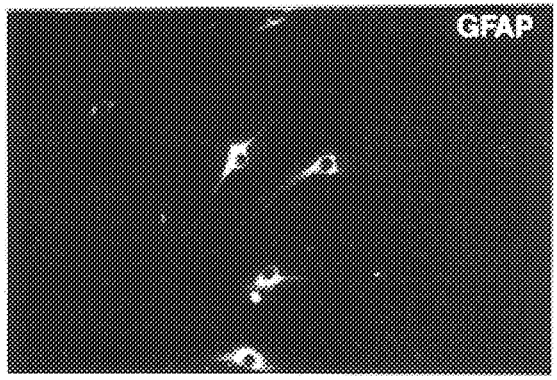
FIG._5F

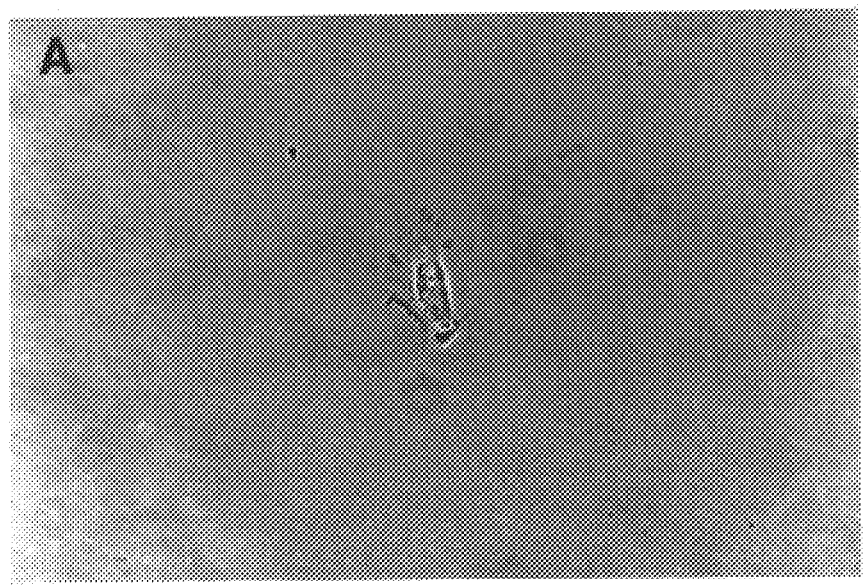
FIG._6A
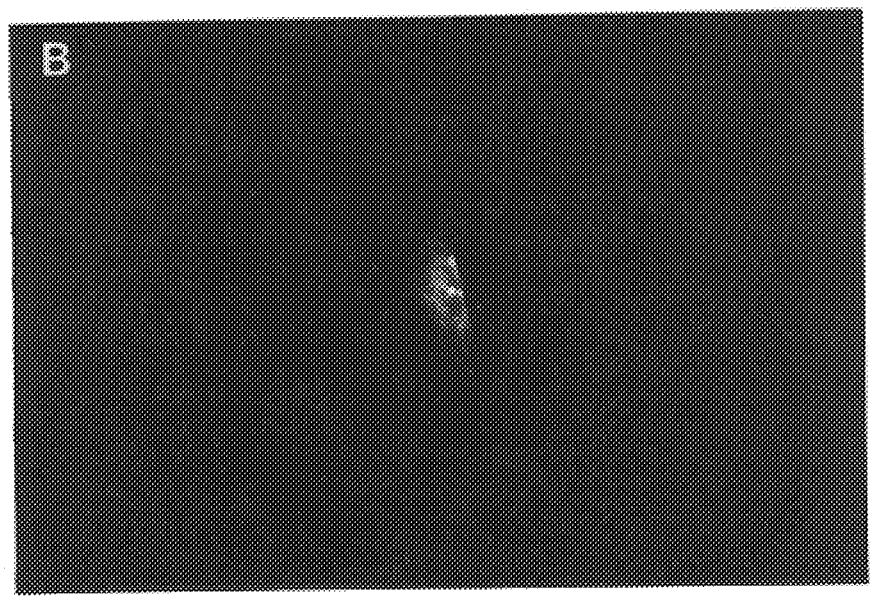
FIG._6B

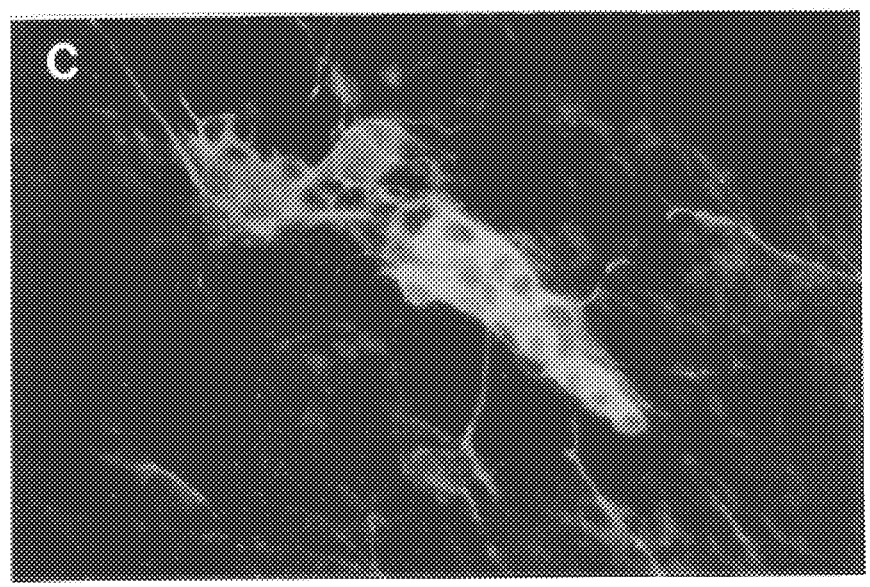
FIG._6C
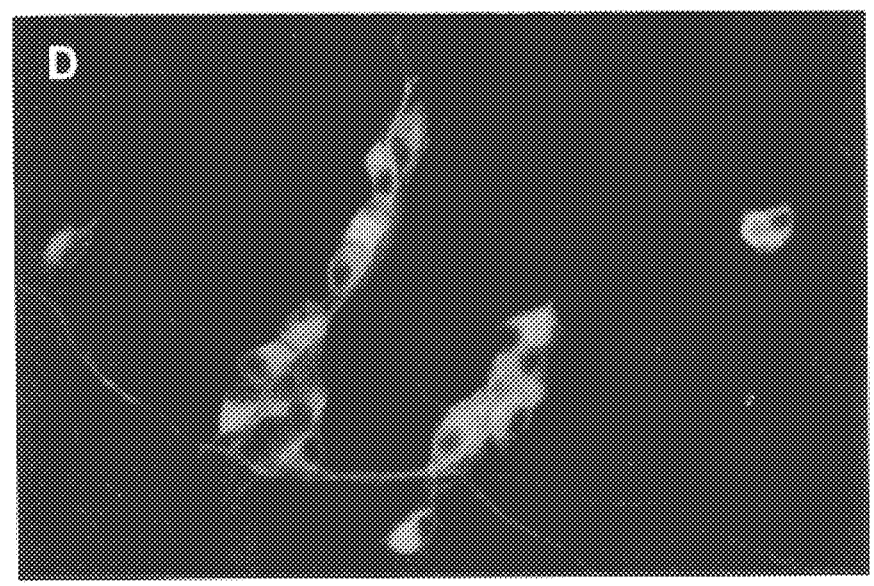
FIG._6D

SELF-RENEWAL OF MAMMALIAN NEURAL CREST CELLS

SINGLE NEURAL CREST FOUNDER CELL

↓ *5-7 DAYS PLATING MEDIUM*

CLONE OF UNDIFFERENTIATED NEURAL CREST CELLS

RECLONE AND IDENTIFY SECONDARY FOUNDER CELLS

↓ ↓ ↓ *10 DAYS DIFFERENTIATION MEDIUM*

SCORE CLONES AS MIXED, GLIAL OR OTHER

↓ ↓ ↓ *10 DAYS DIFFERENTIATION MEDIUM*

FIX AND STAIN FOR ANTIGENIC MARKERS

FIG._7

1° CLONE (DAY 7)
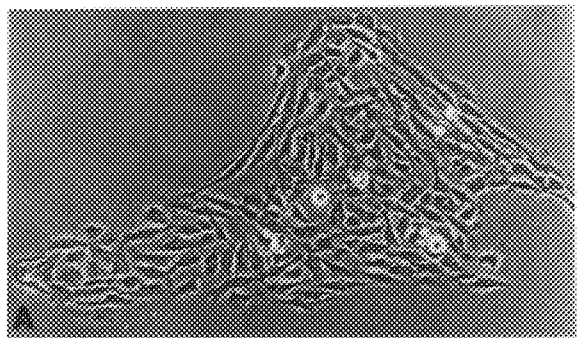
FIG._8A
2° FOUNDERS
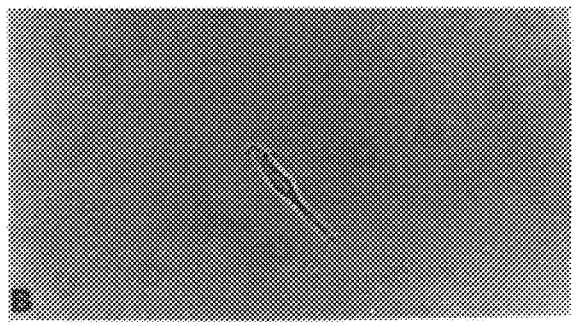
FIG._8B
2° FOUNDERS
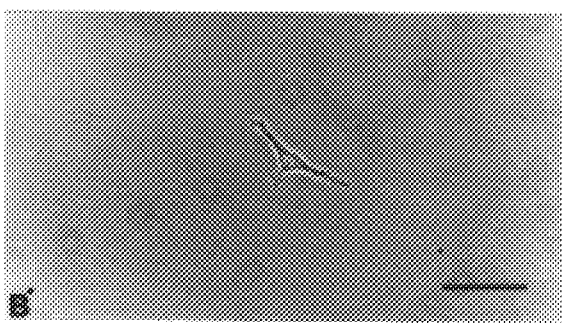
FIG._8B'
2° CLONES (DAY 17)
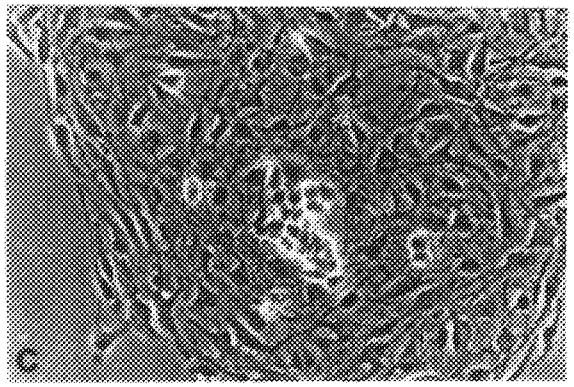
FIG._8C
2° CLONES (DAY 17)
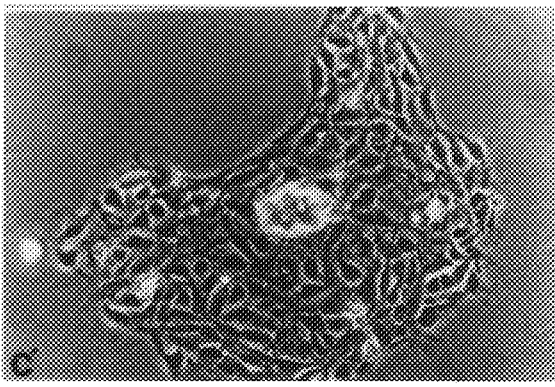
FIG._8C'

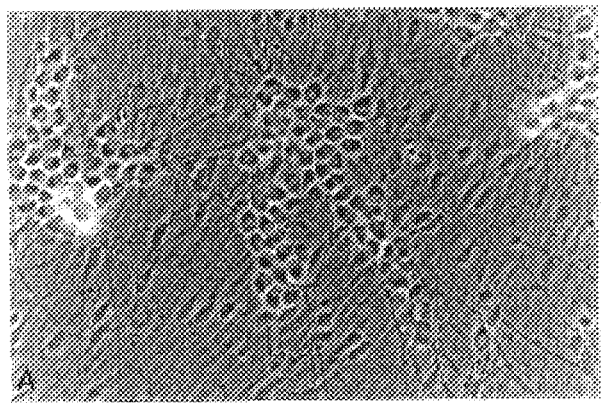
FIG._9A
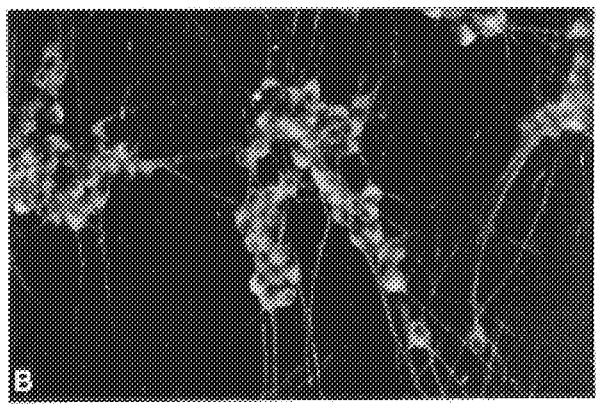
NF160
FIG._9B
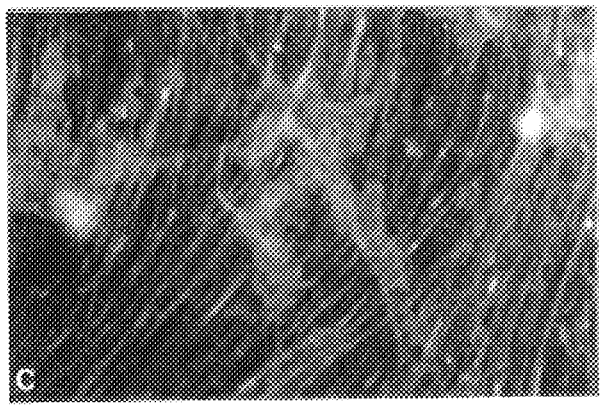
GFAP
FIG._9C

SUBSTRATE EFFECT ON FATE OF MAMMALIAN NEURAL CREST CELLS
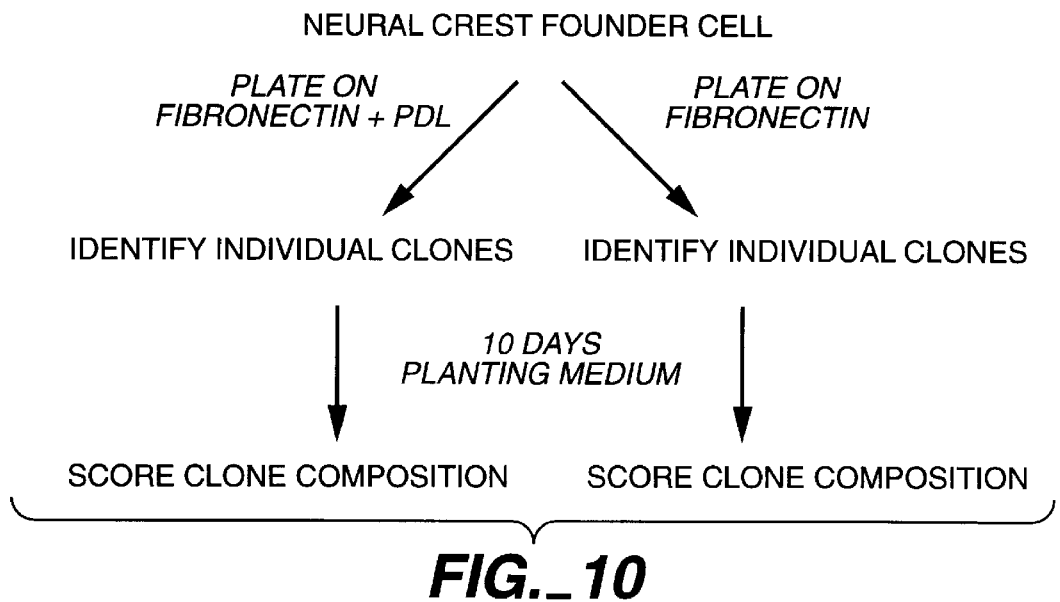
FIG._10
INSTRUCTIVE EFFECT OF SUBSTRATE ON CREST CELL FATE
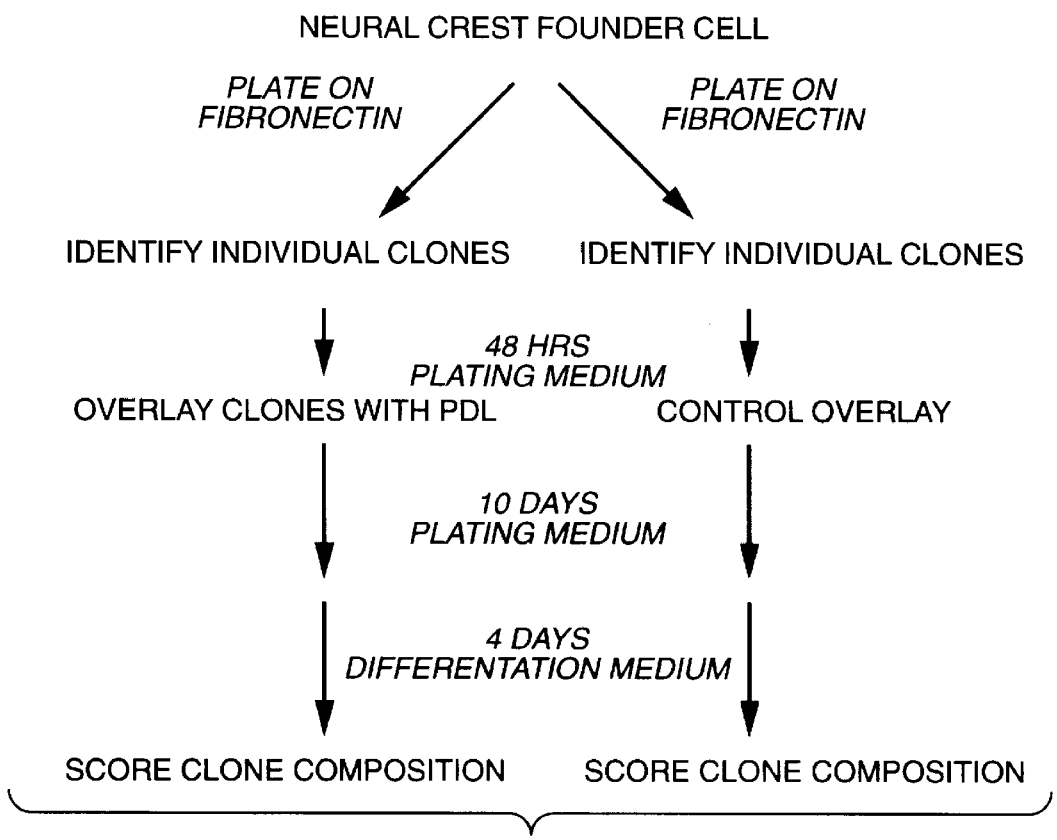
FIG._13

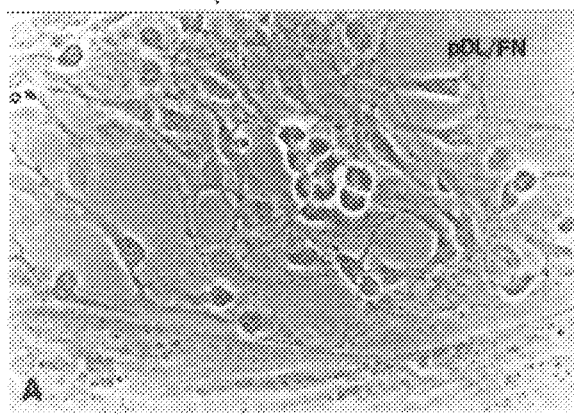
FIG._11A
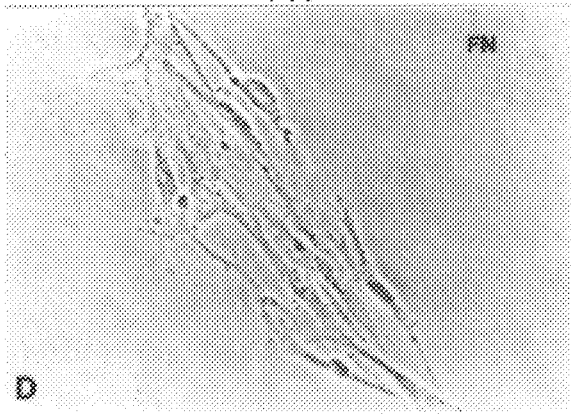
FIG._11D
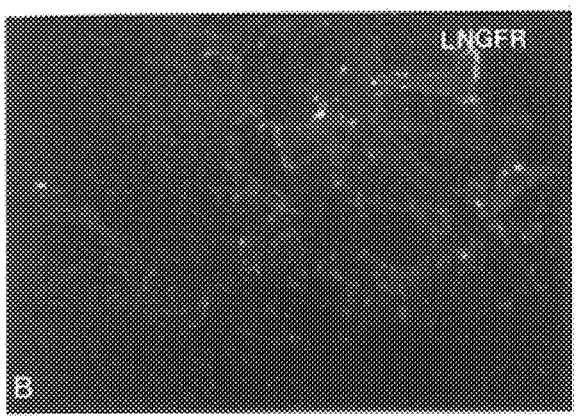
FIG._11B
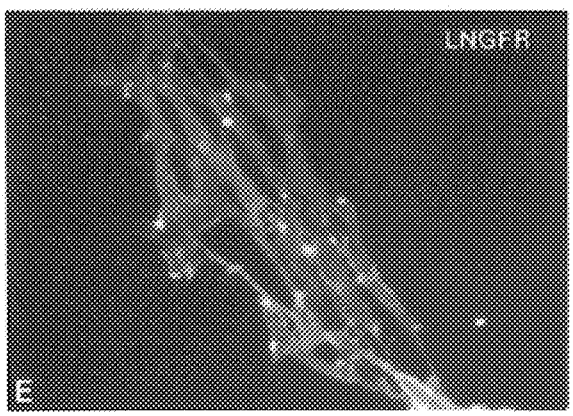
FIG._11E
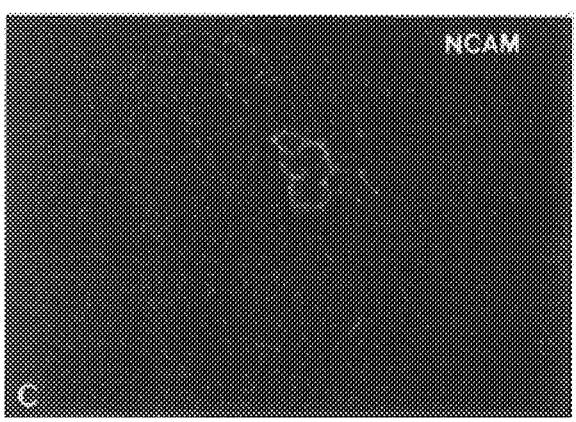
FIG._11C
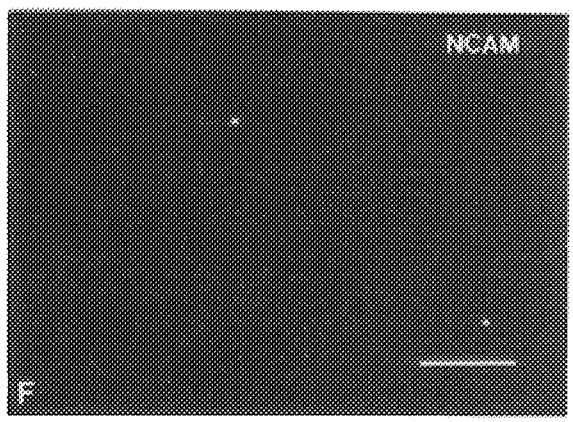
FIG._11F

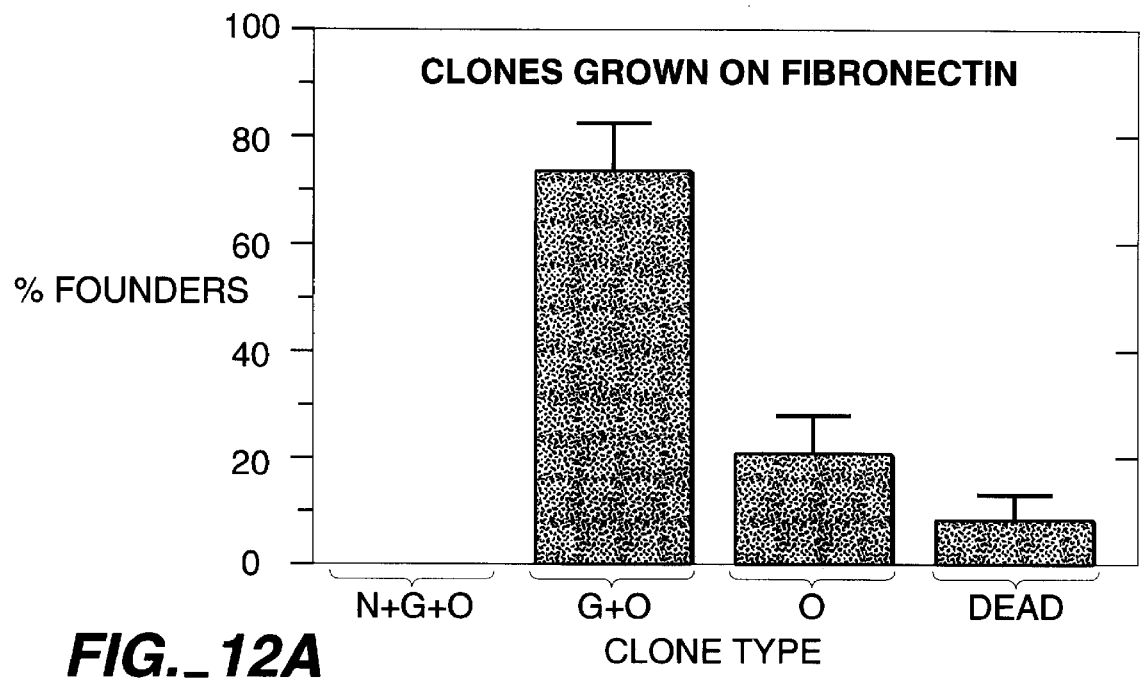
FIG._12A
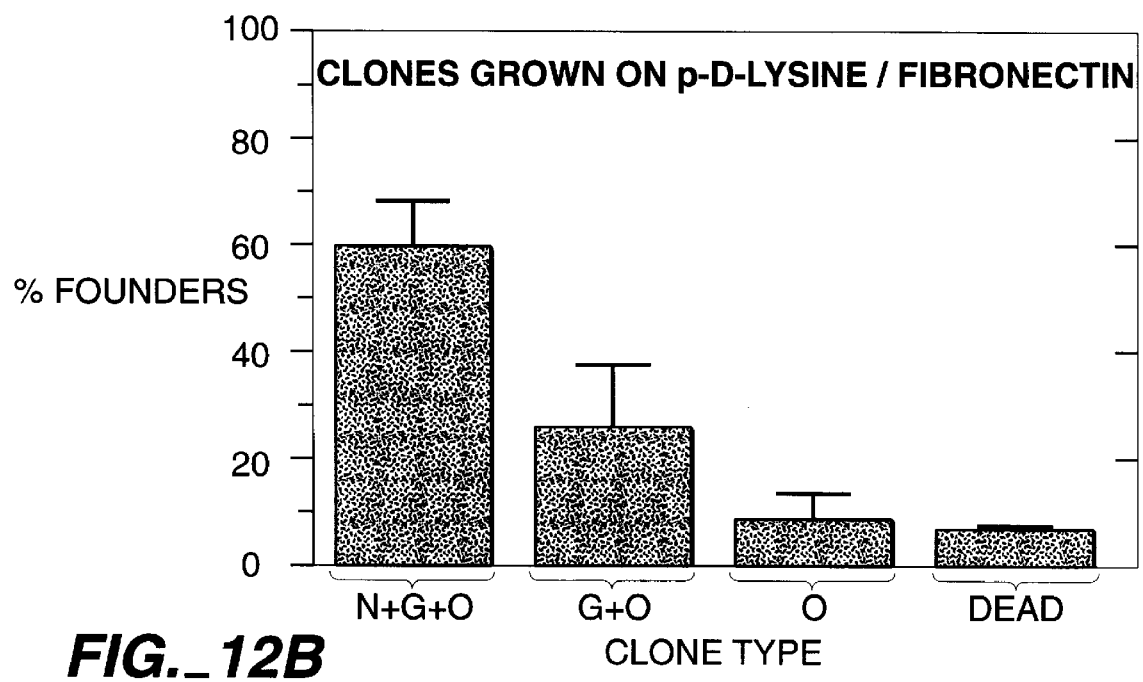
FIG._12B

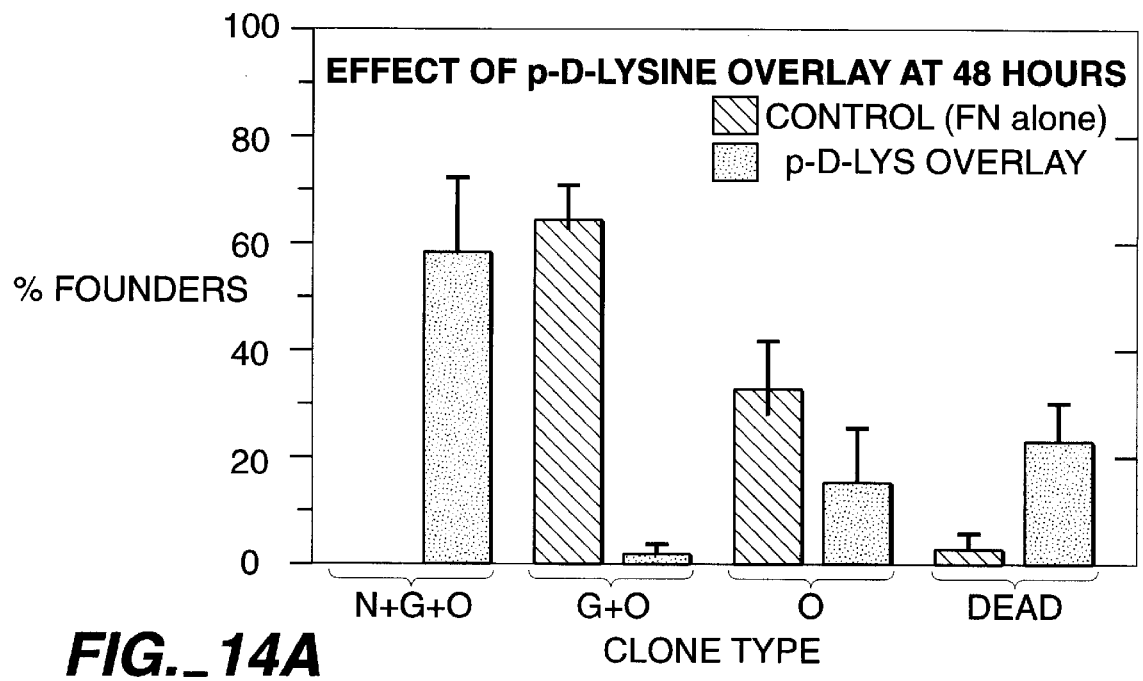
FIG._14A
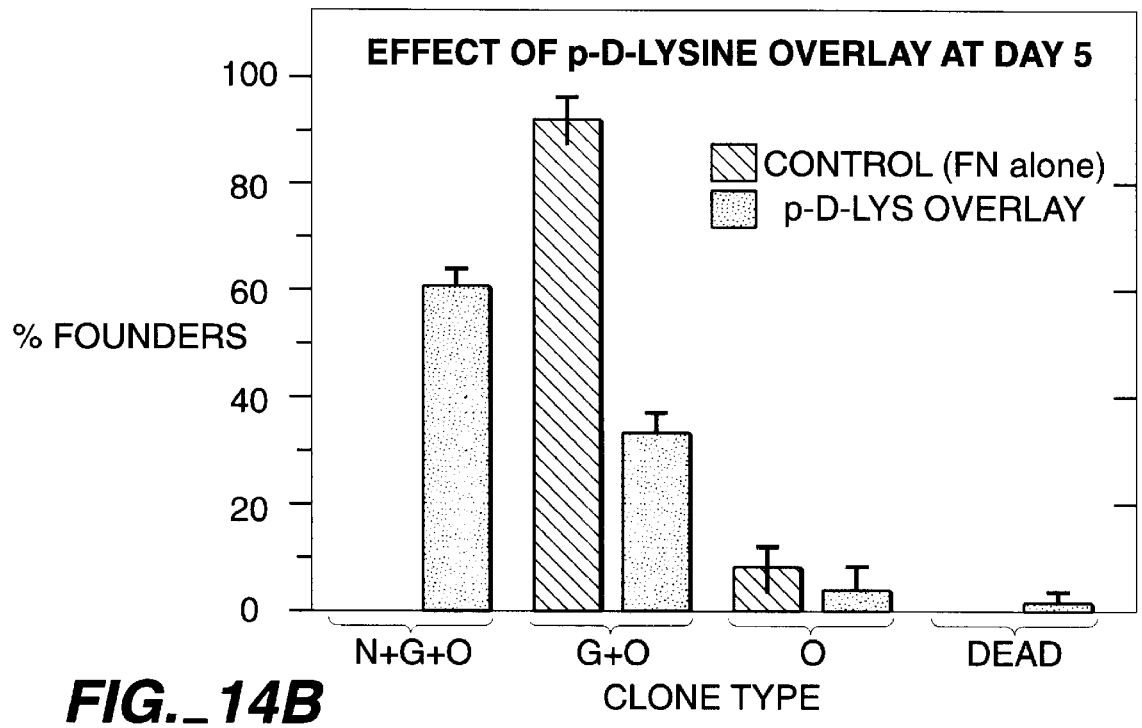
FIG._14B

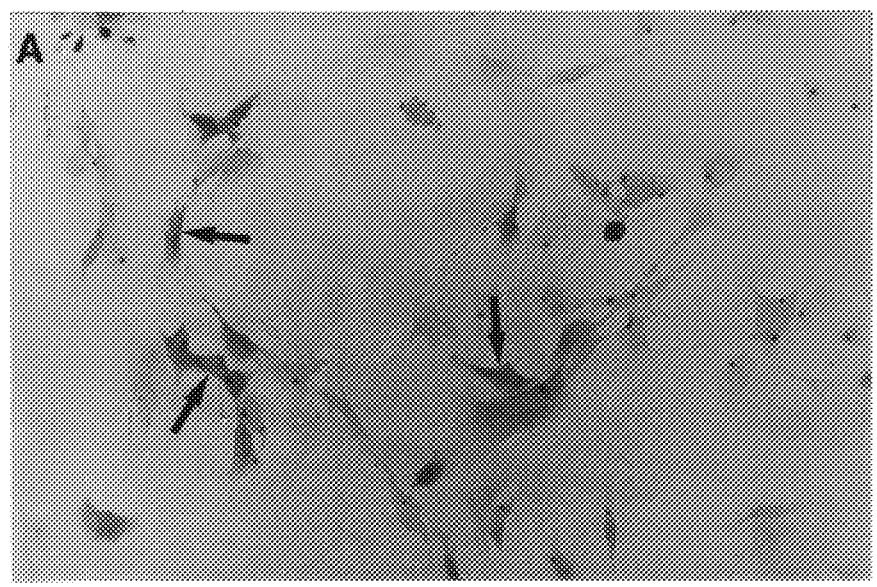
FIG._15A
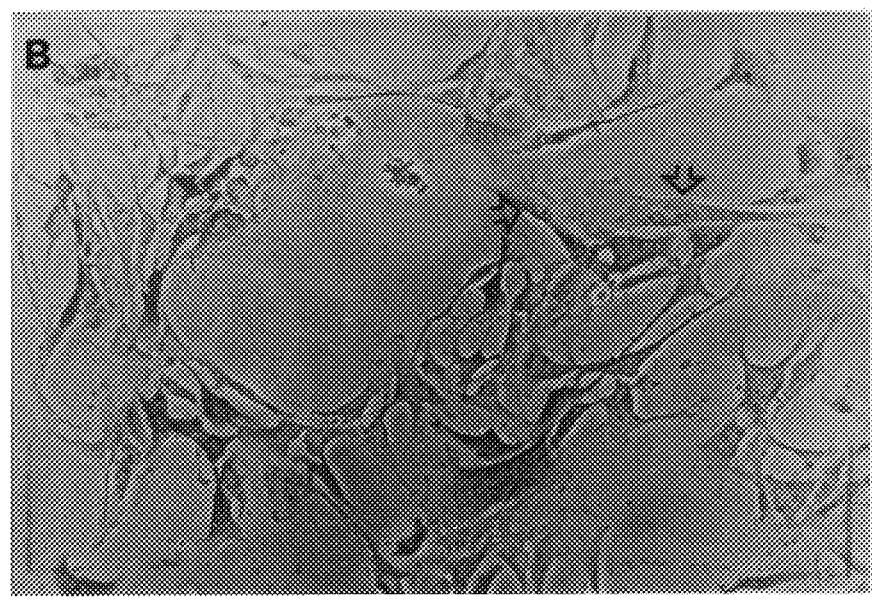
FIG._15B

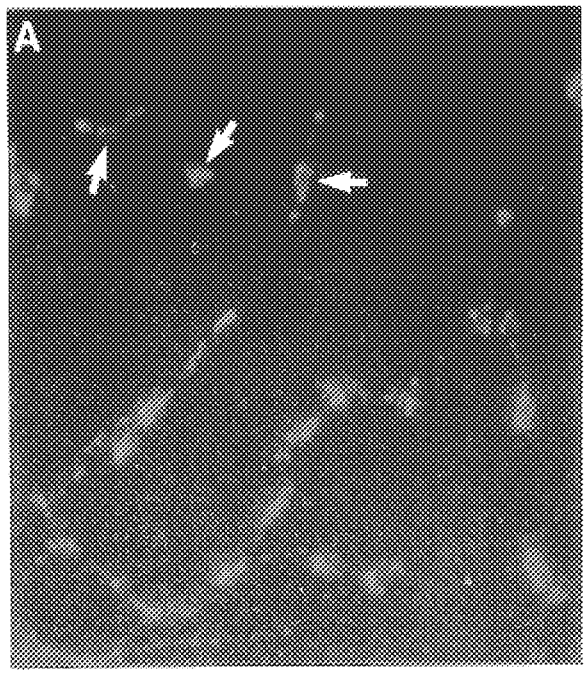
FIG._16A
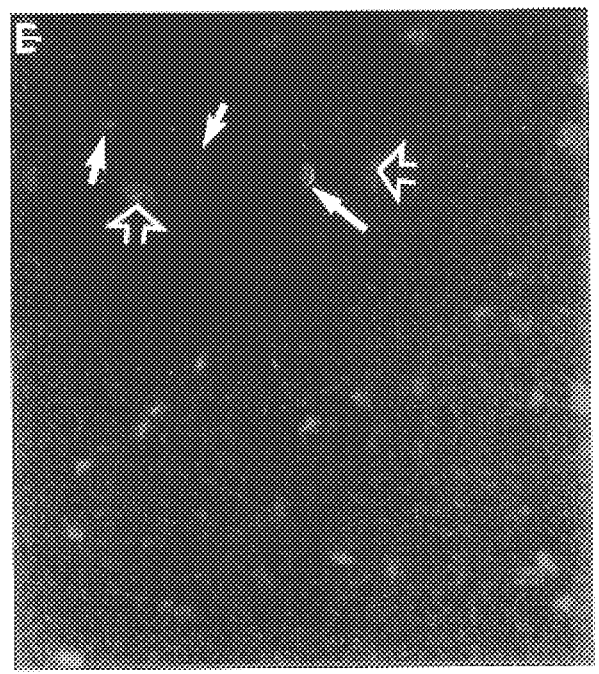
FIG._16B

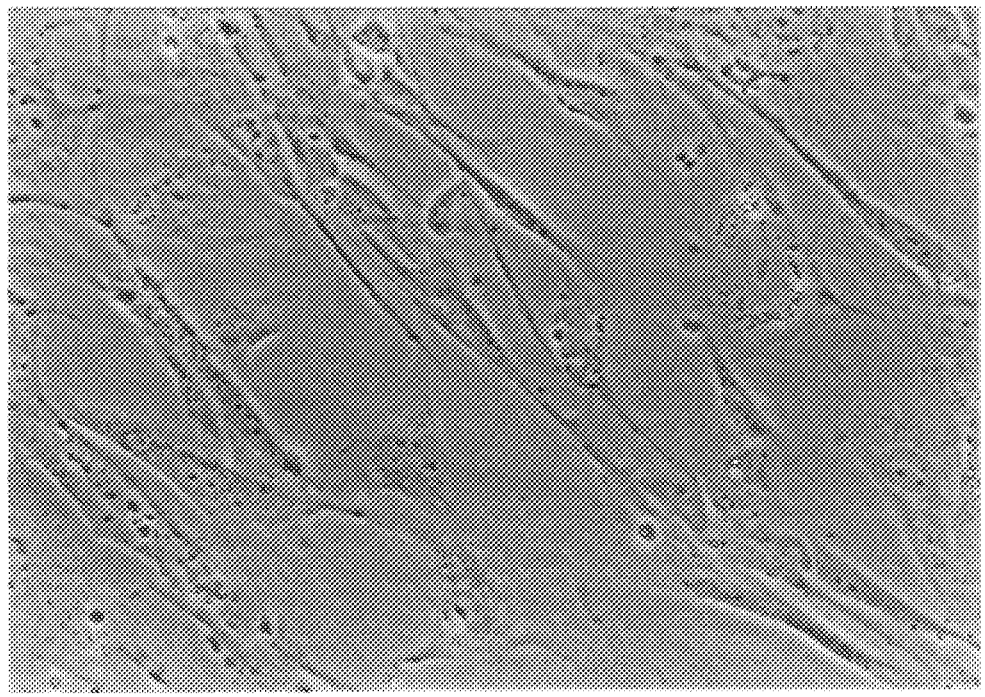
FIG._17A
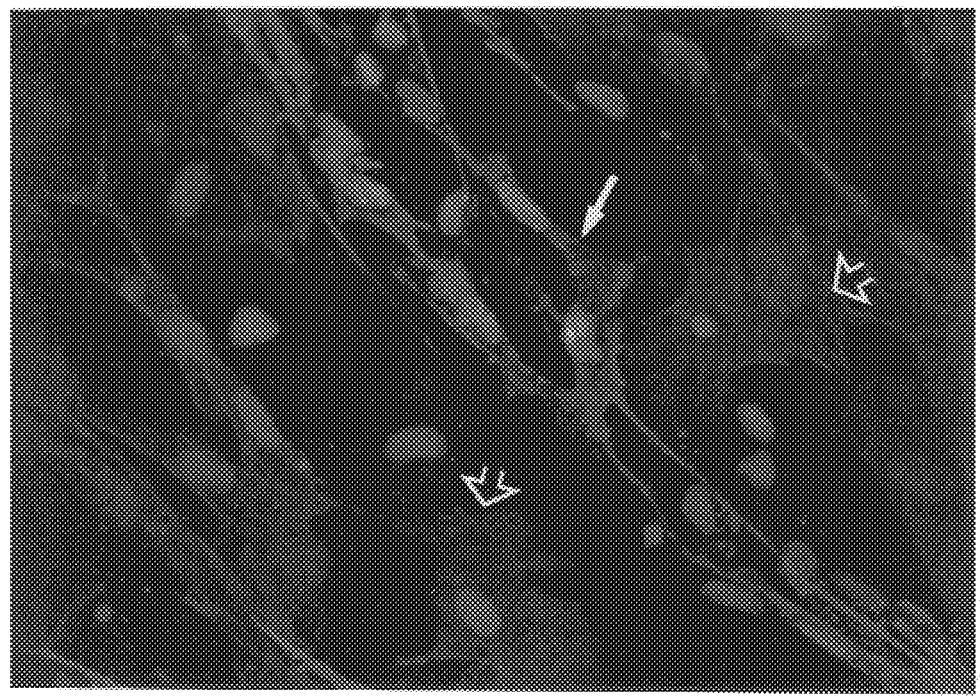
FIG._17B

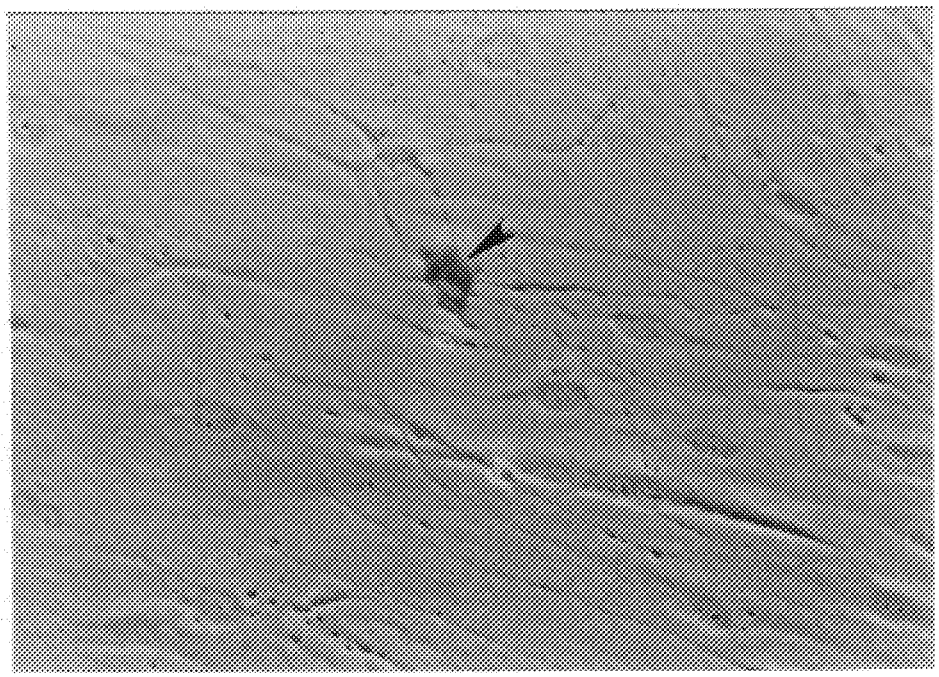
FIG._18A
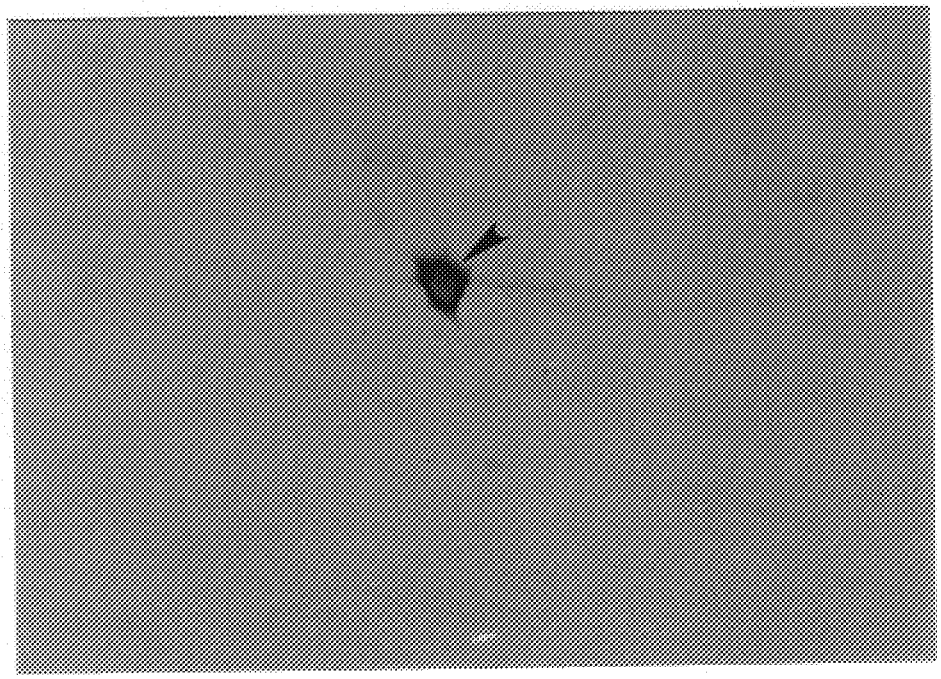
FIG._18B

FIG._18C
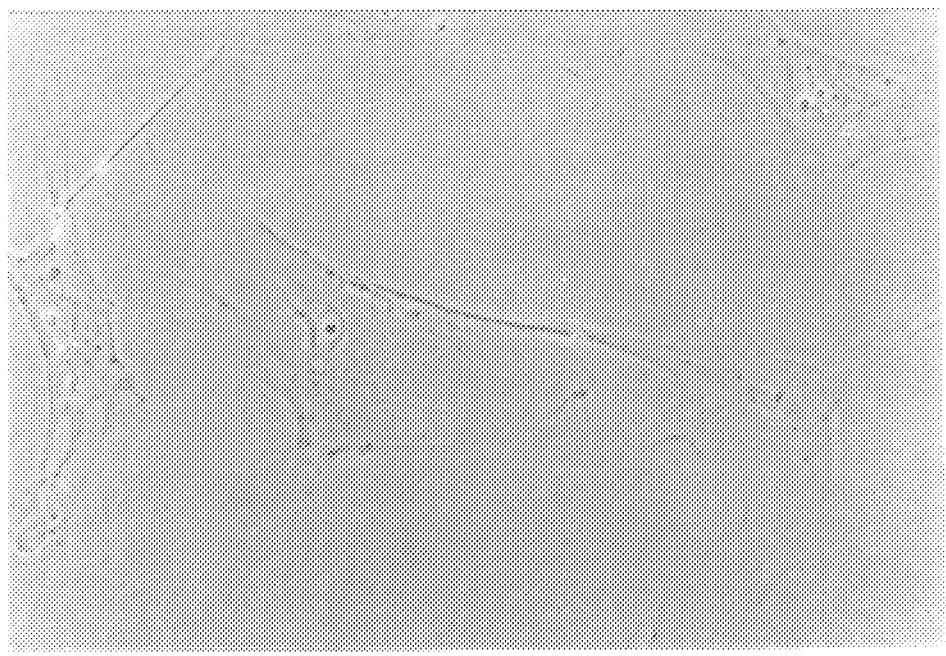
FIG._19A

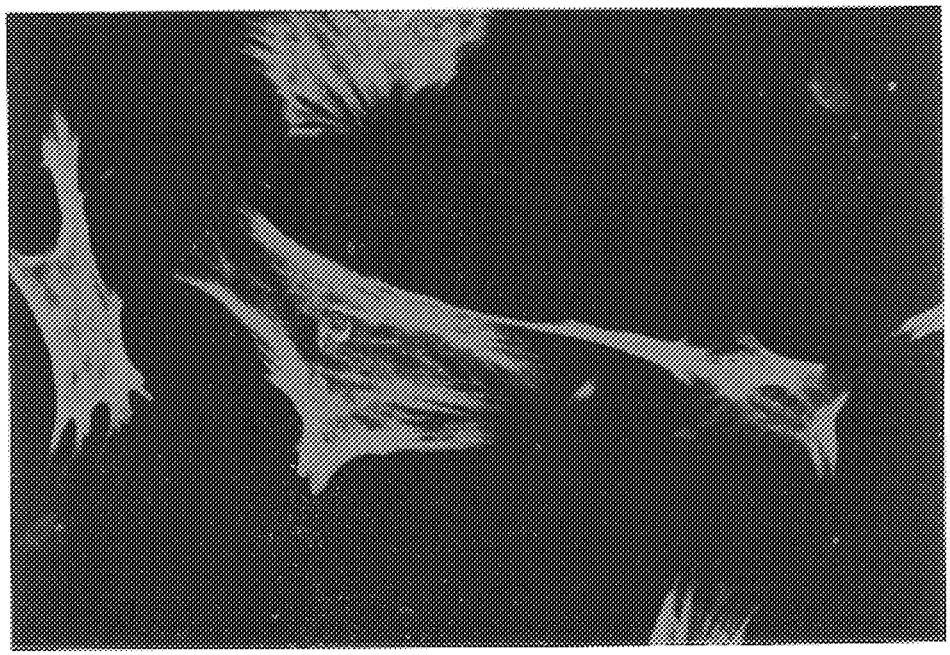
FIG._19B
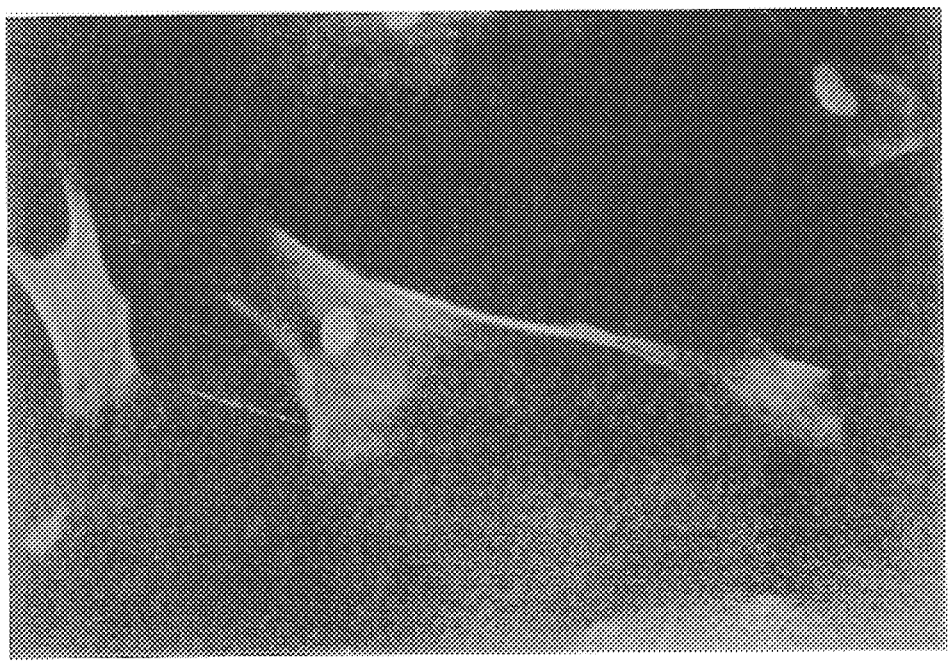
FIG._19C

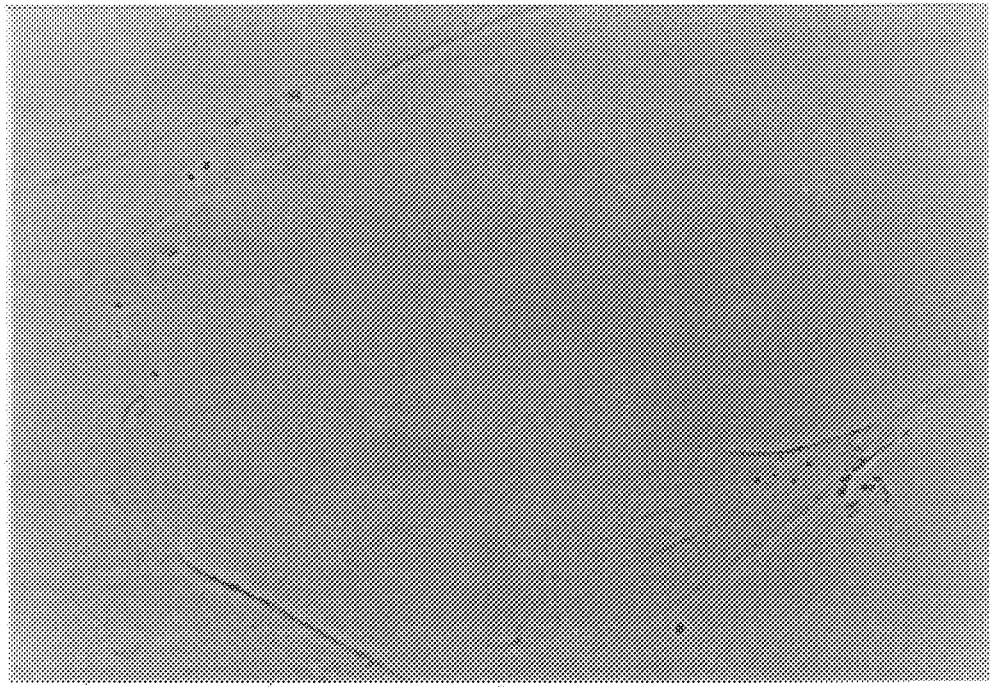
FIG._20A
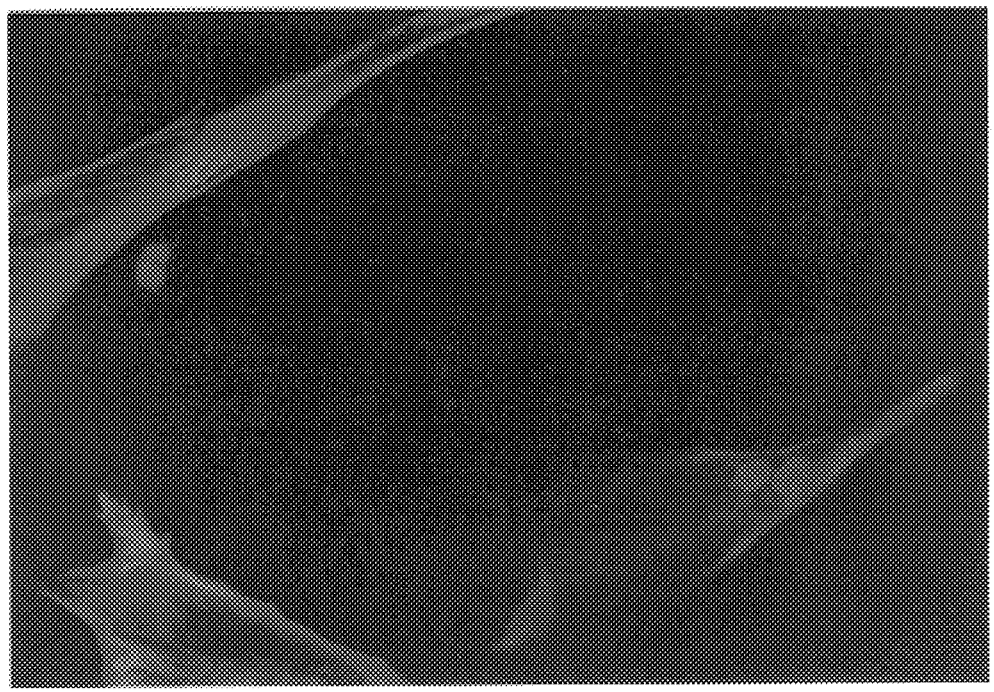
FIG._20B

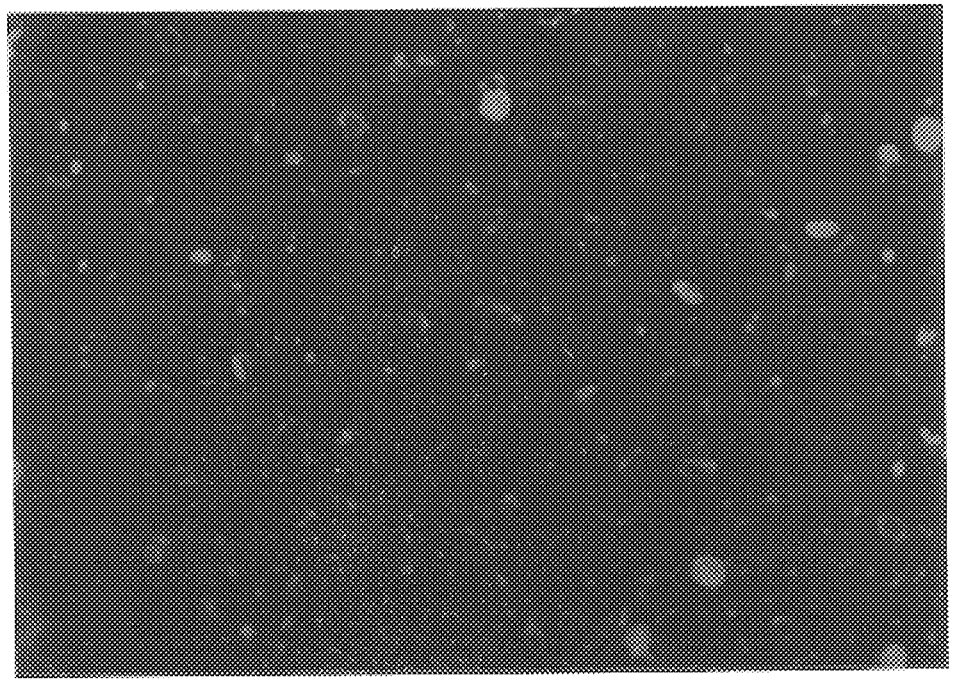
*FIG._21A*
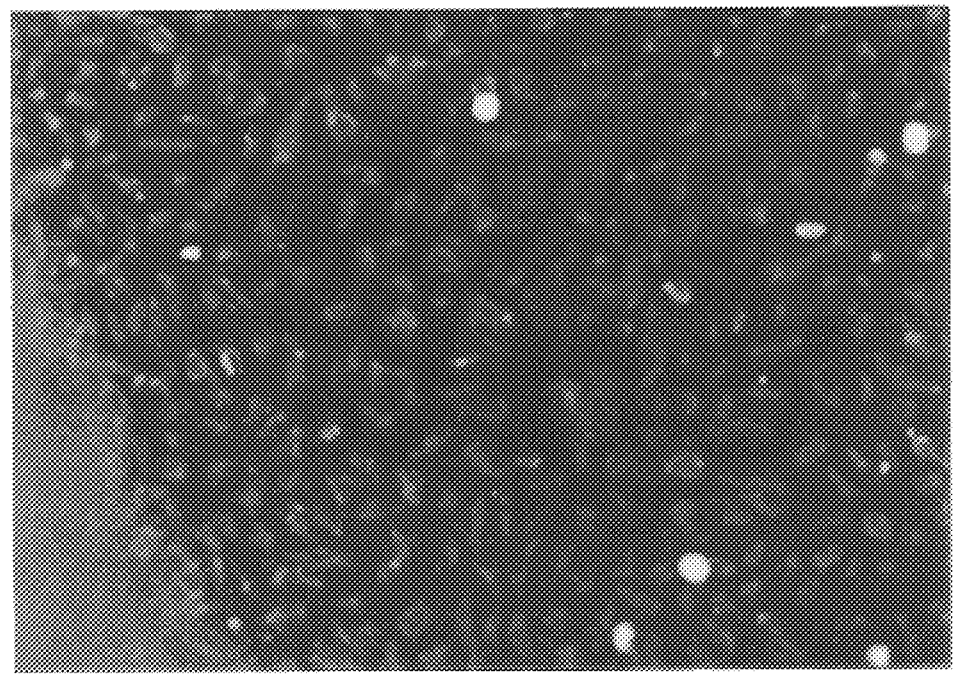
*FIG._21B*

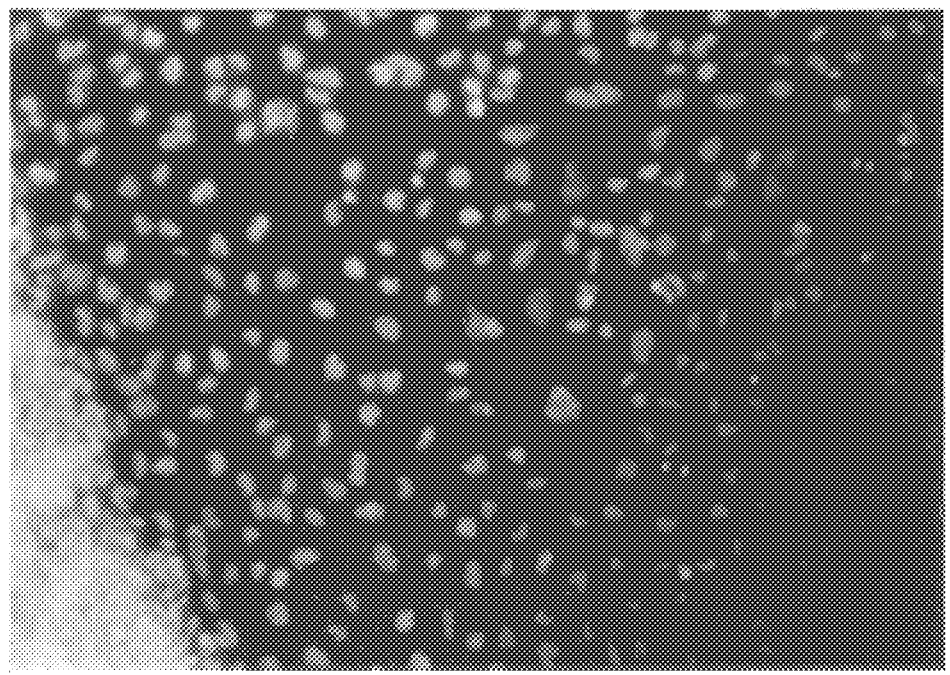
FIG._21C
FIG._22A
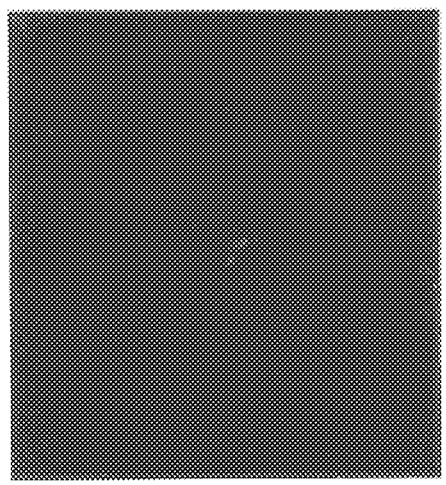
FIG._22B

*FIG._22C*
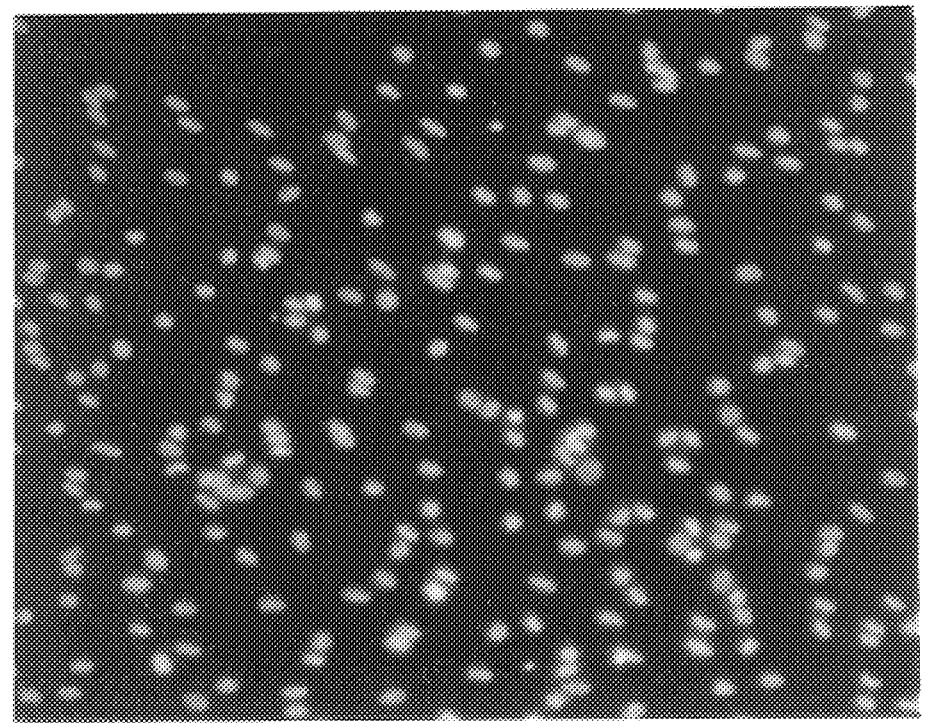
*FIG._22D*

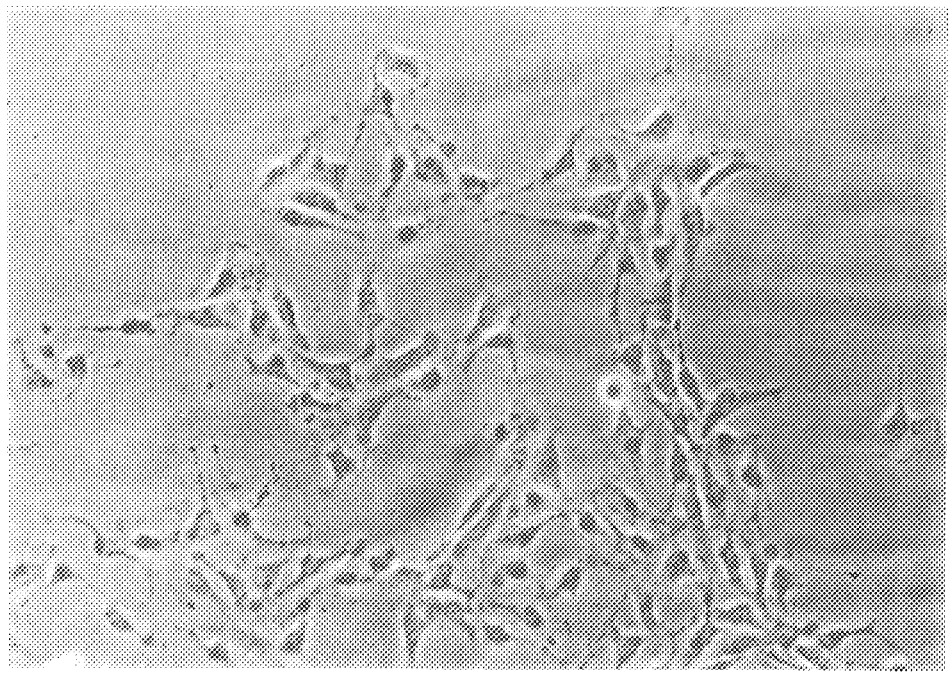
FIG._23A
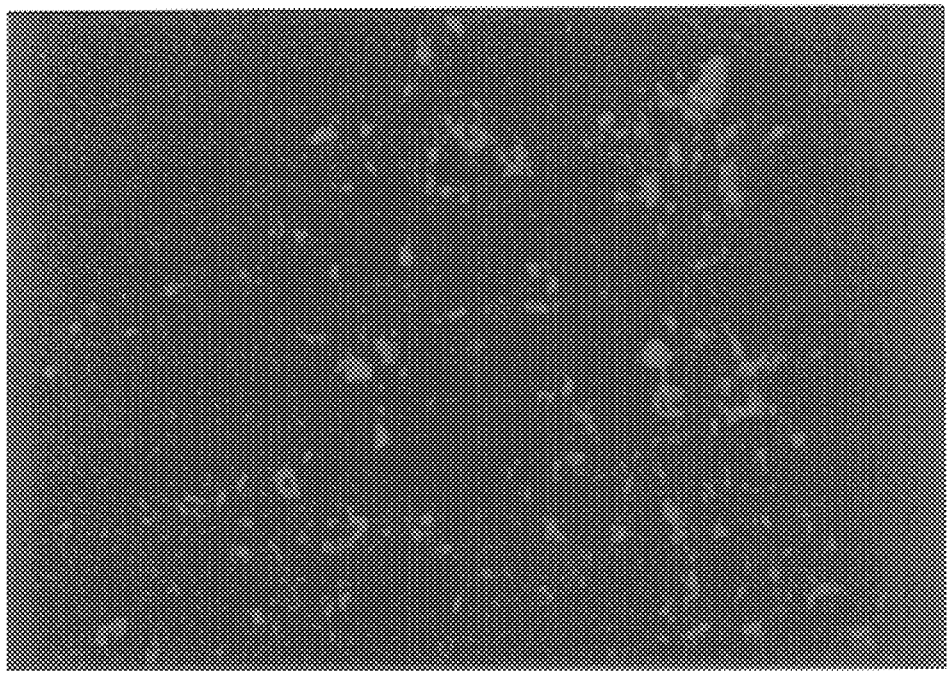
FIG._23B

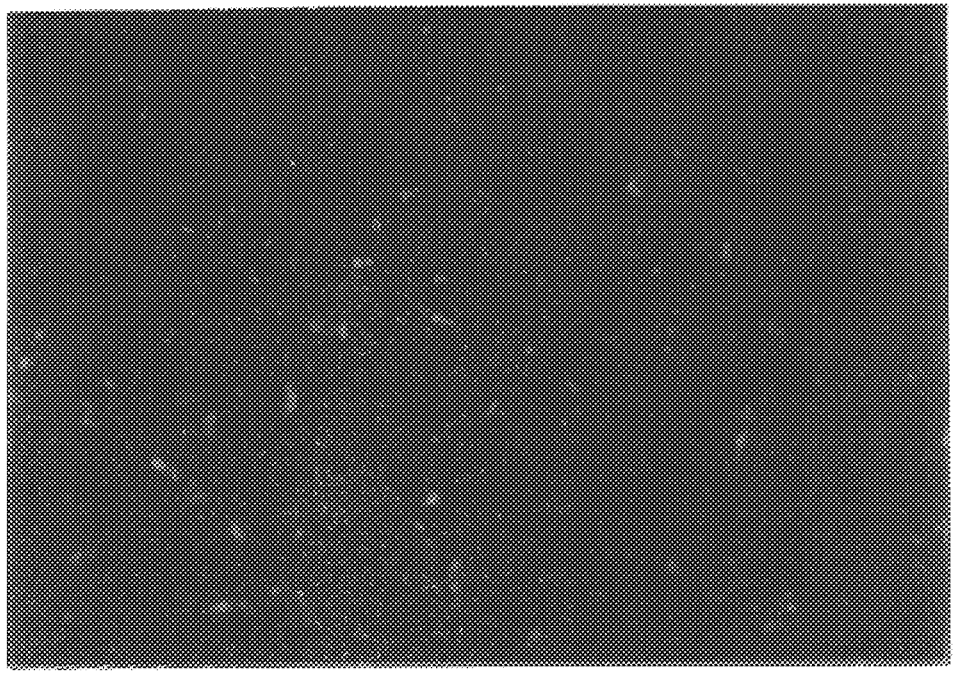
FIG._23C
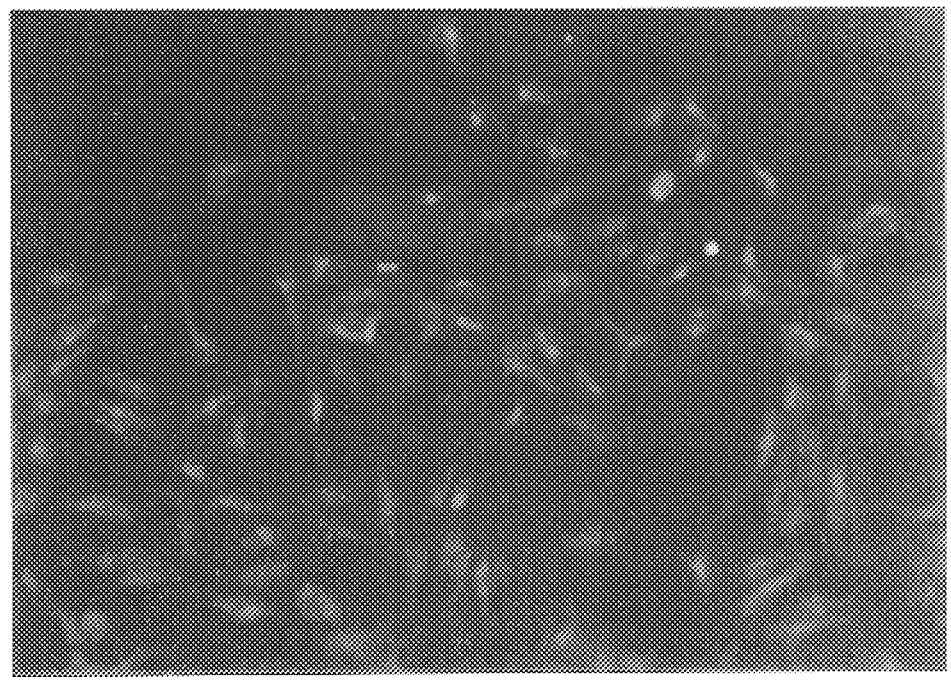
FIG._23D

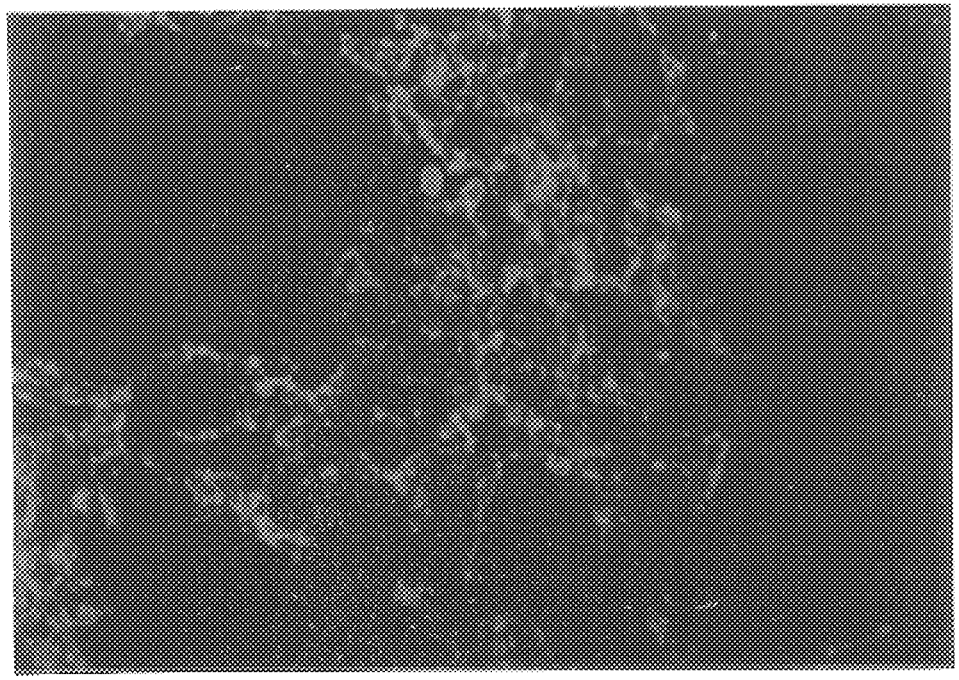
FIG._24A
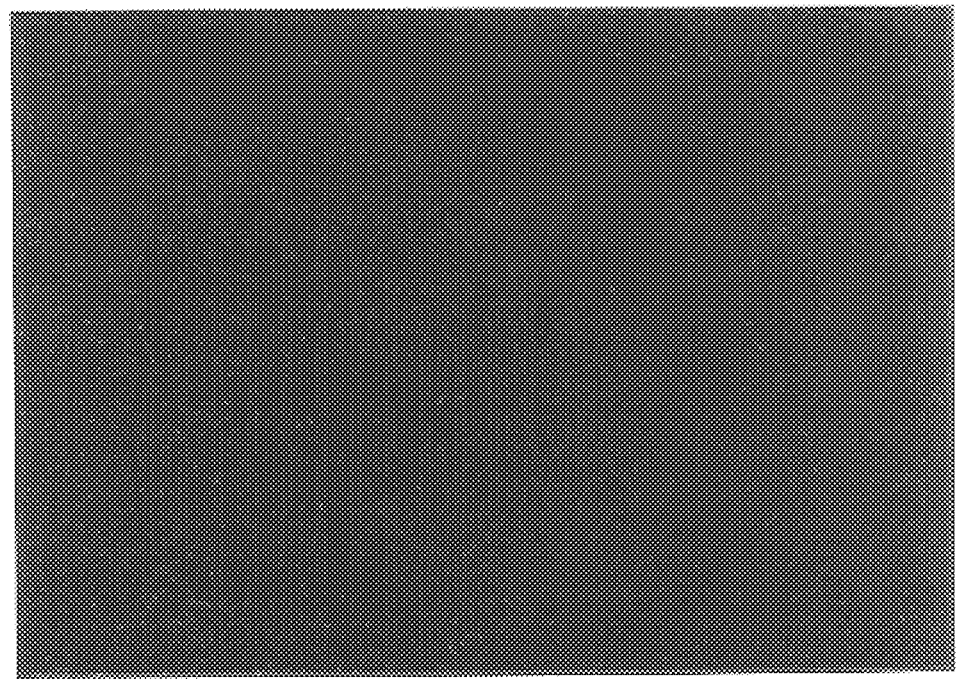
FIG._24B

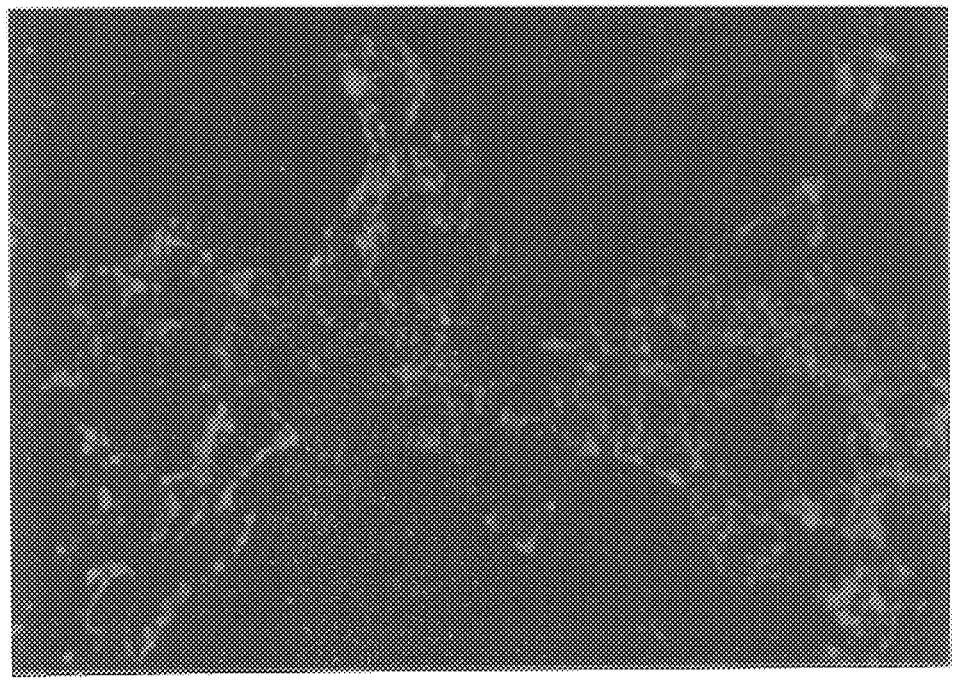
FIG._24C
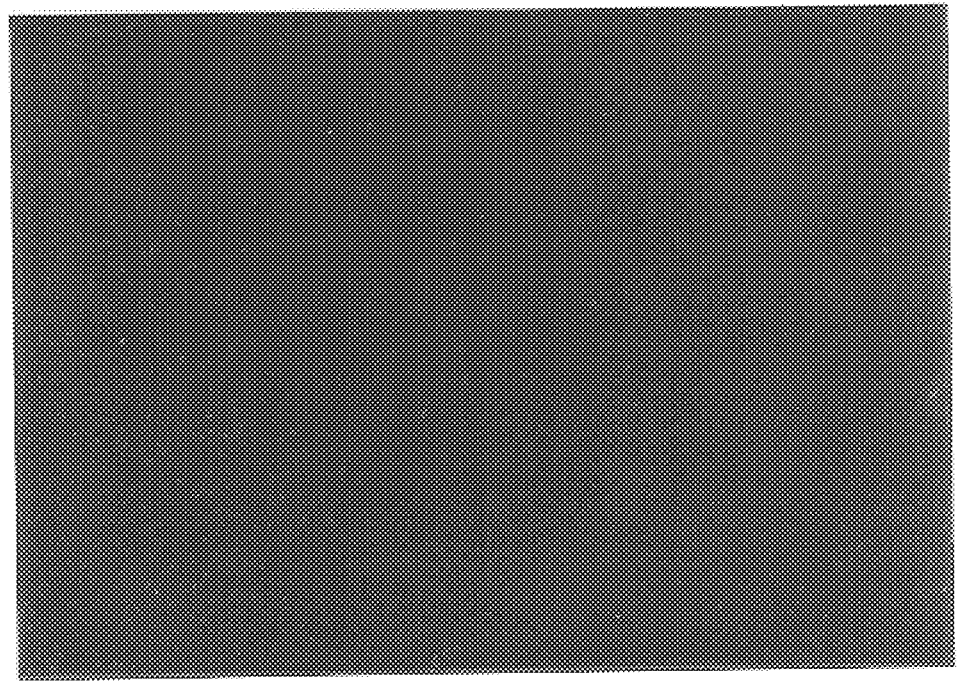
FIG._24D

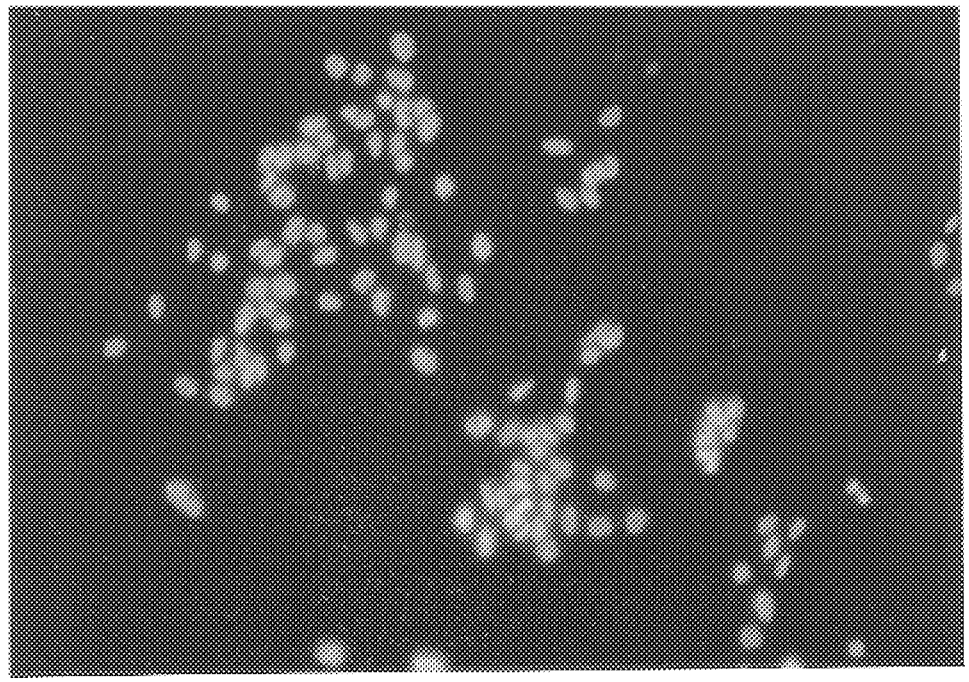
FIG._25A
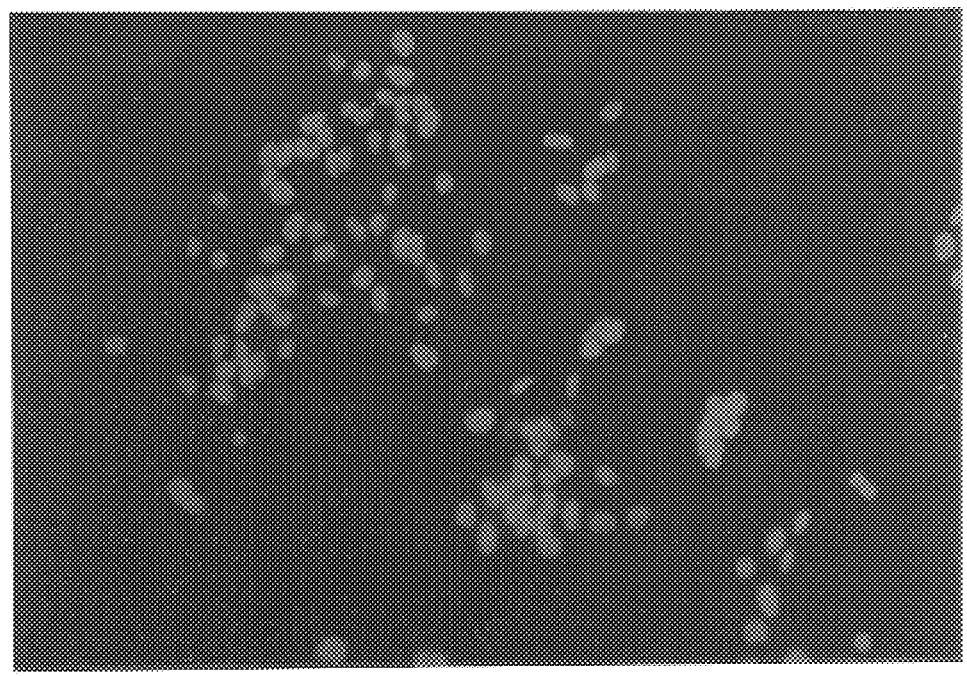
FIG._25B

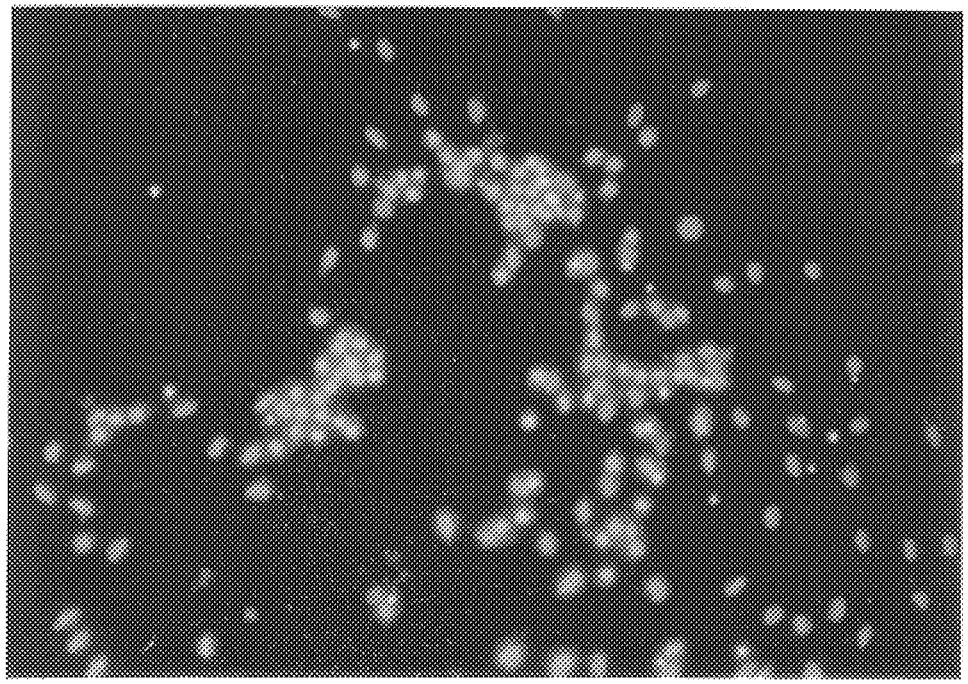
FIG._25C
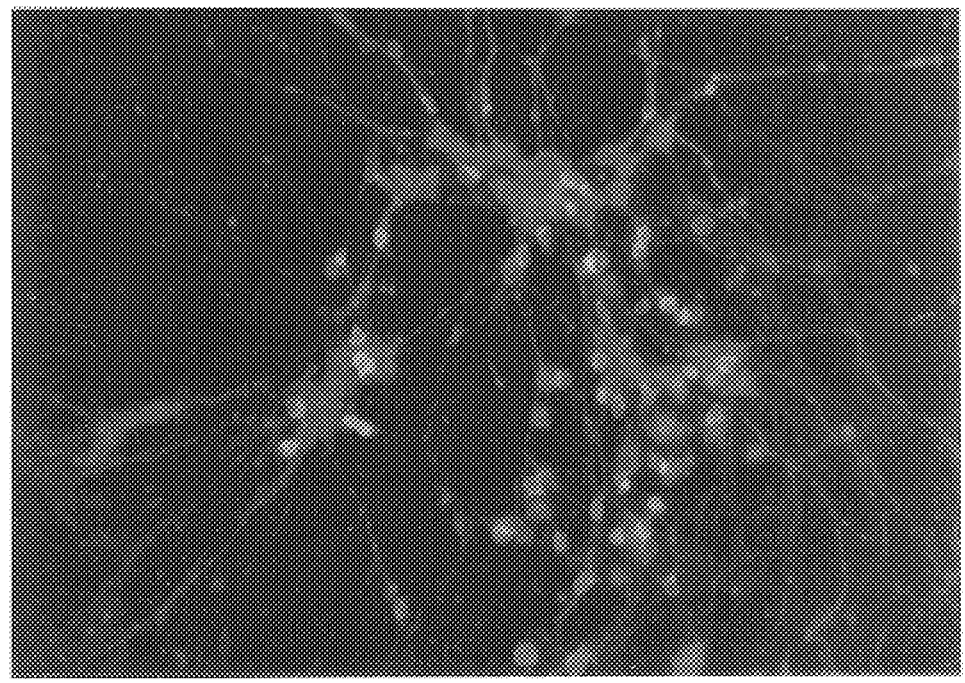
FIG._25D

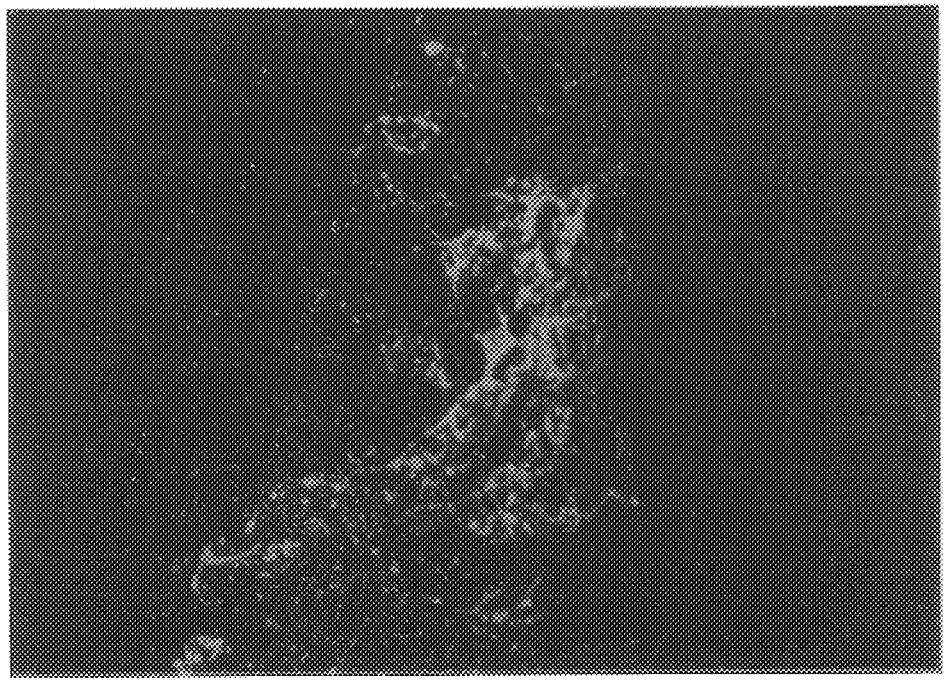
FIG._26A
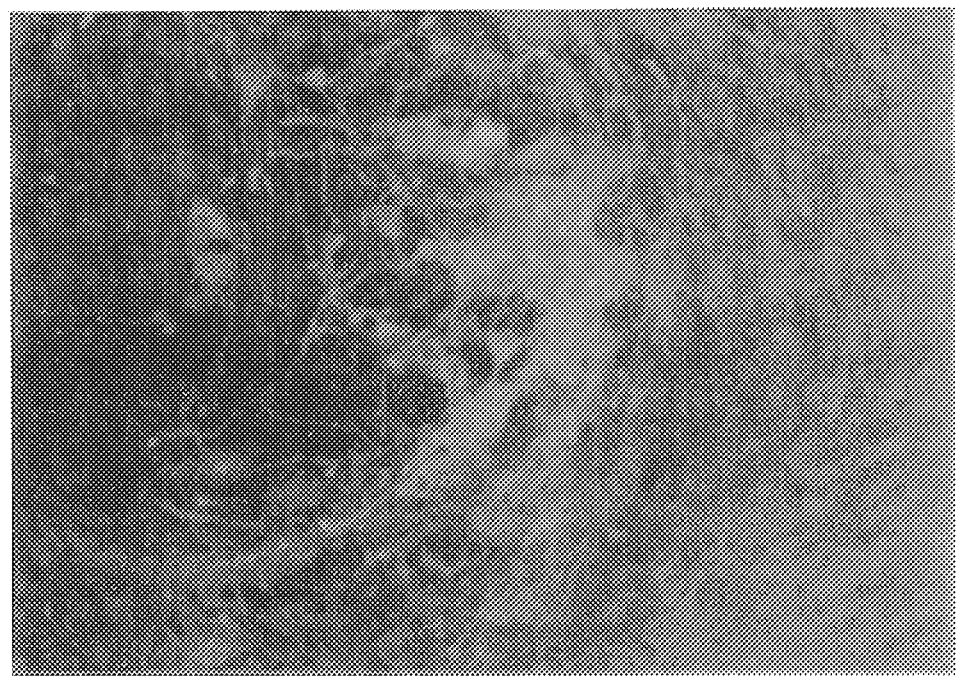
FIG._26B

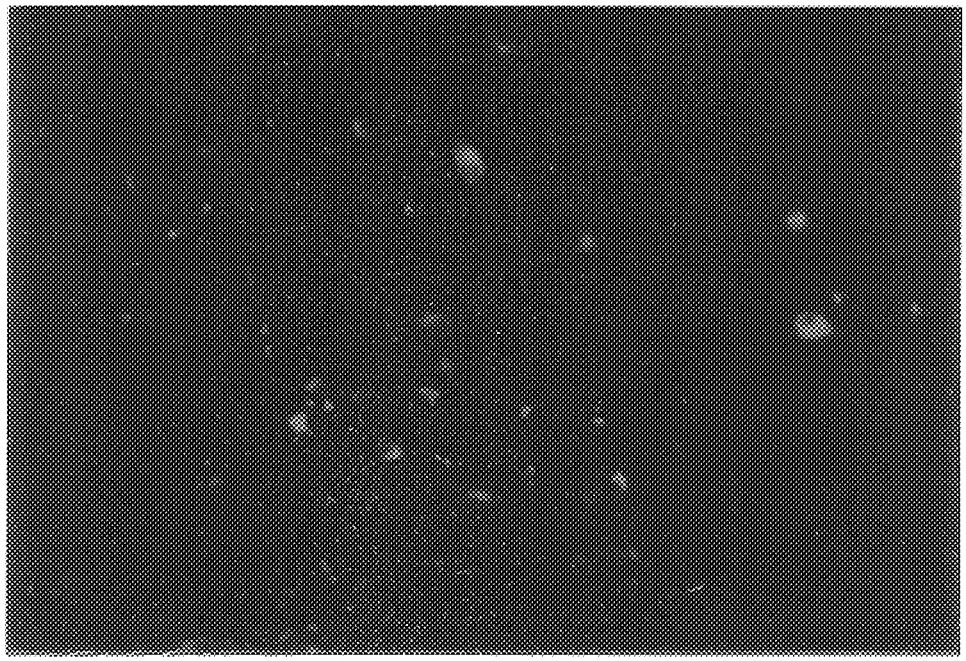
FIG._26C
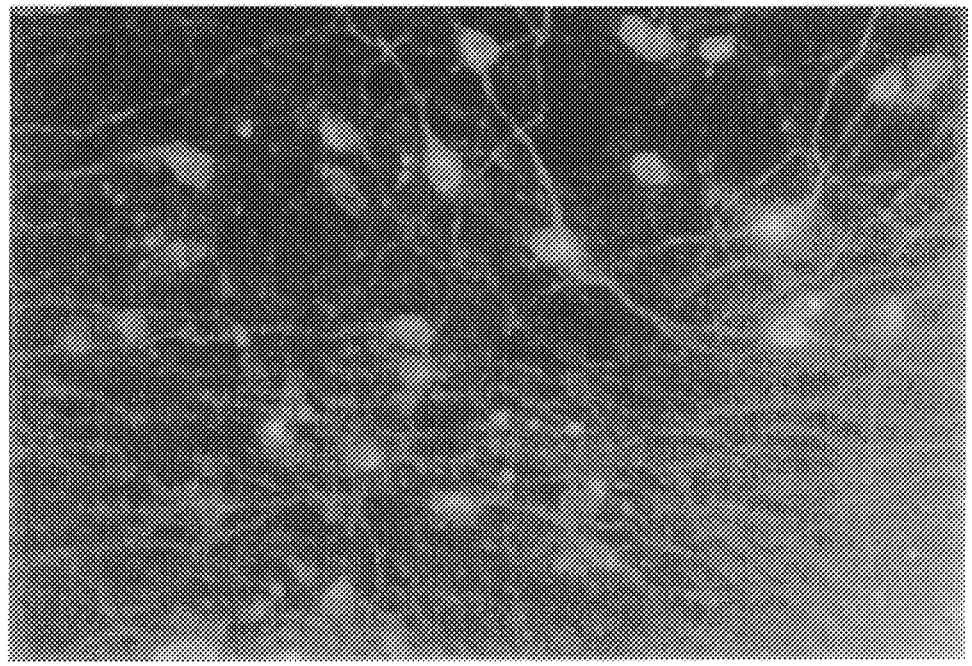
FIG._26D

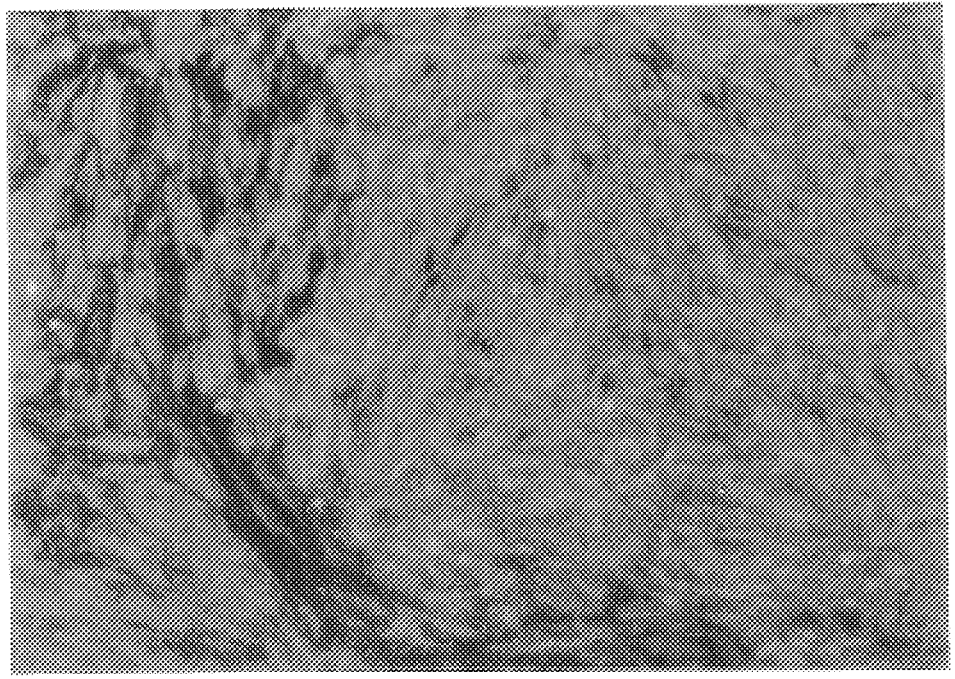
FIG._27A
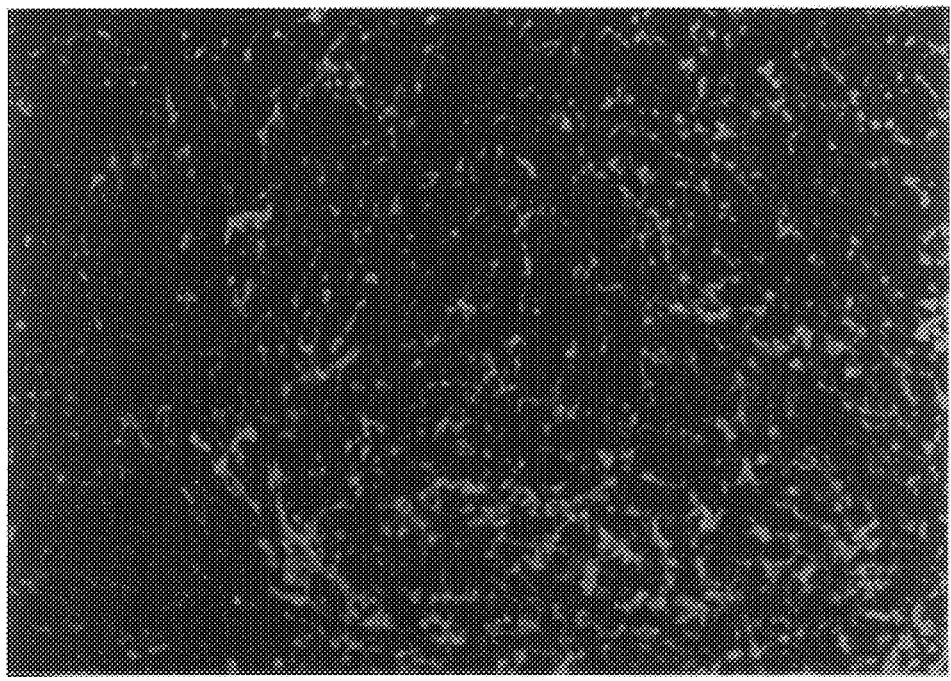
FIG._27B

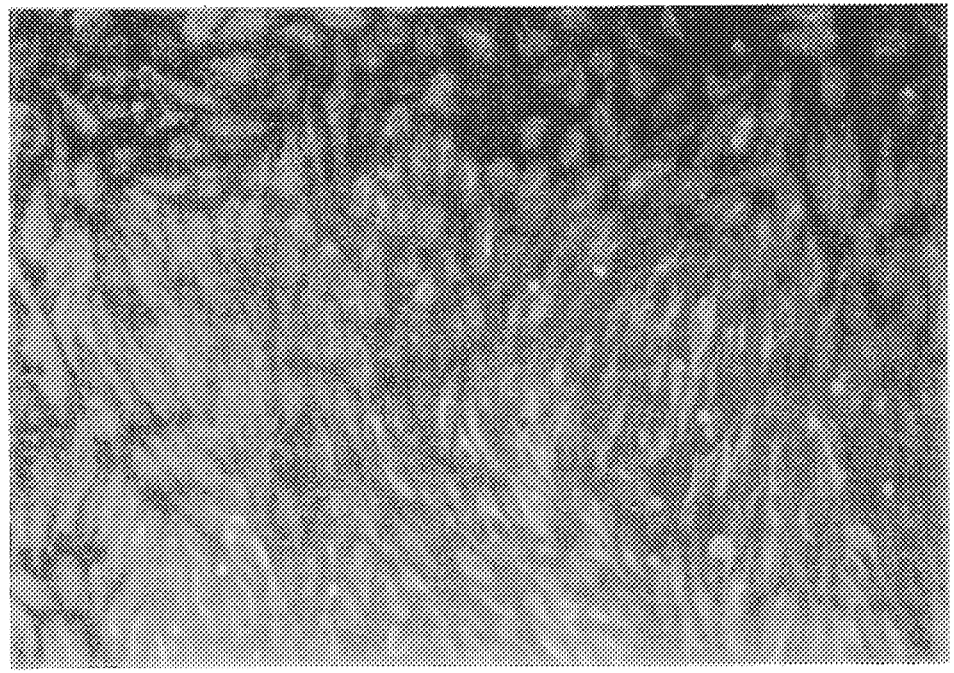
FIG._27C
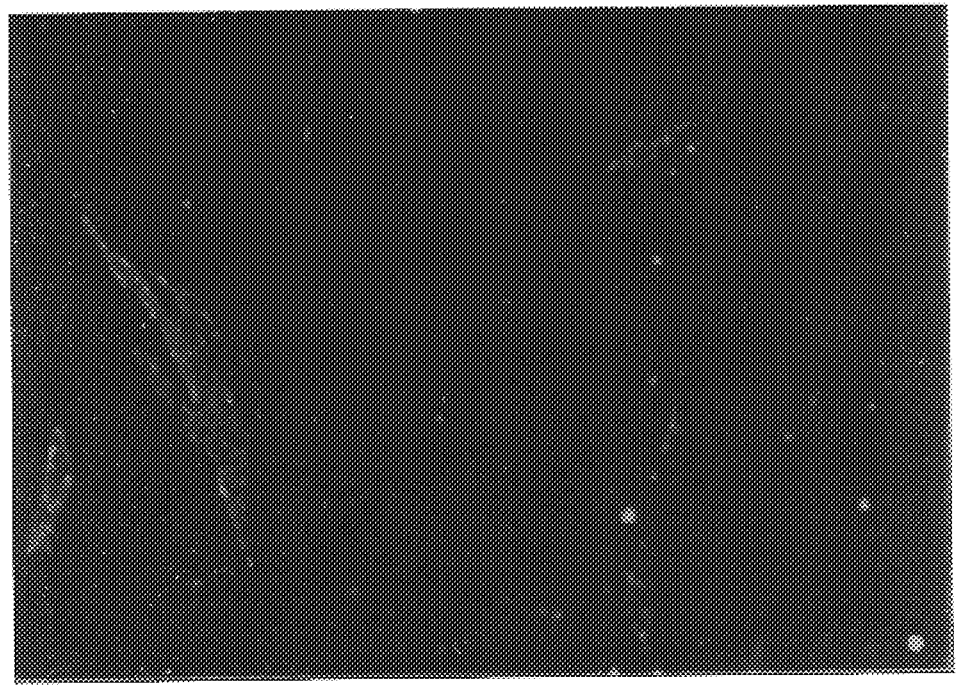
FIG._27D

FIG._28A
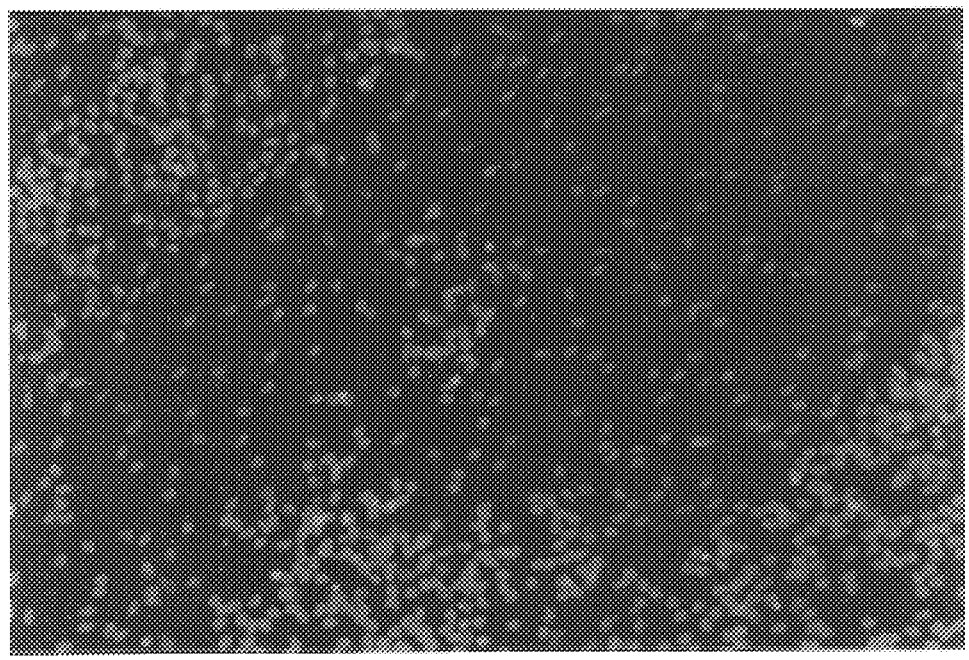
FIG._28B

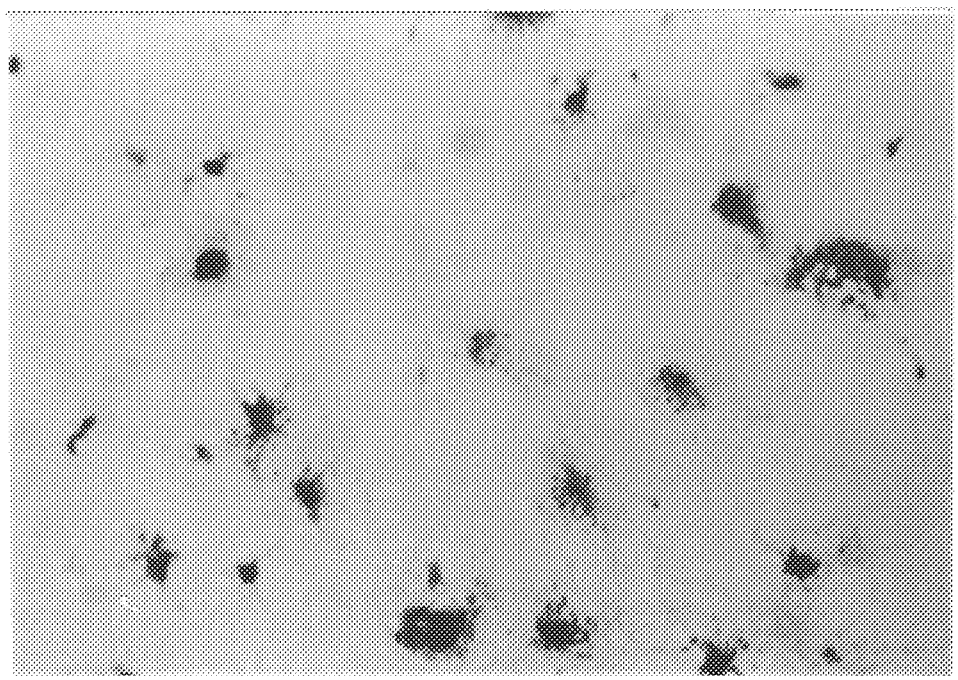
FIG._29A
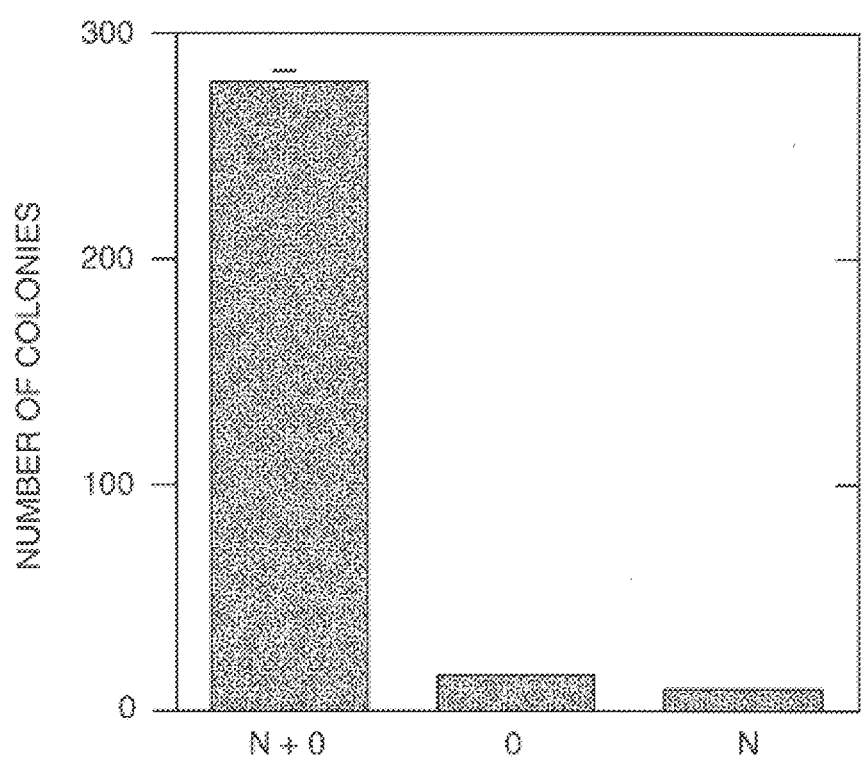
FIG._29B

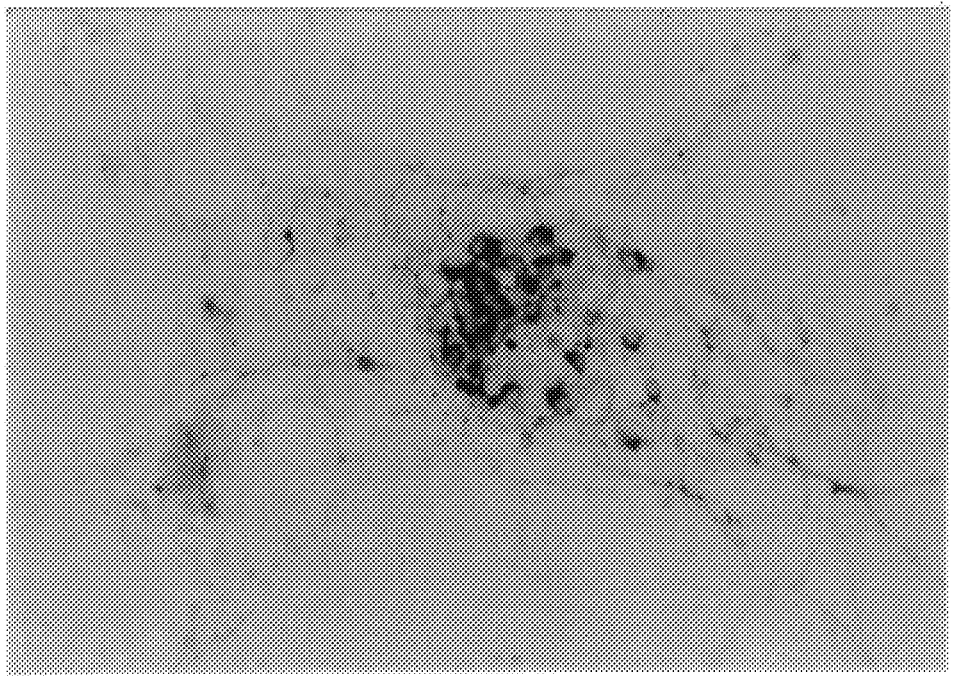
*FIG._29C*
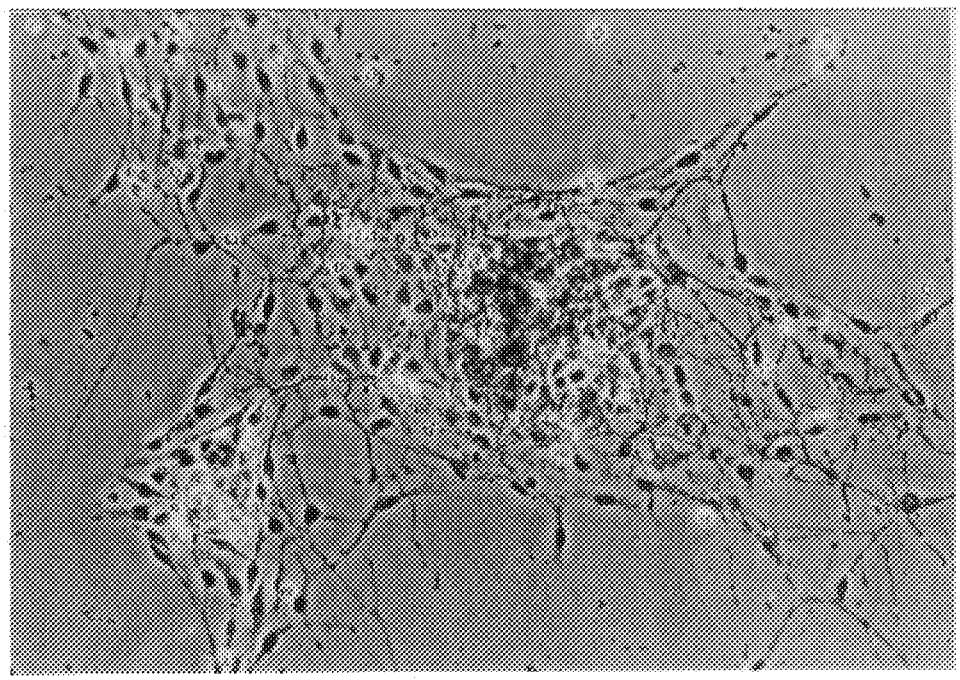
*FIG._29D*

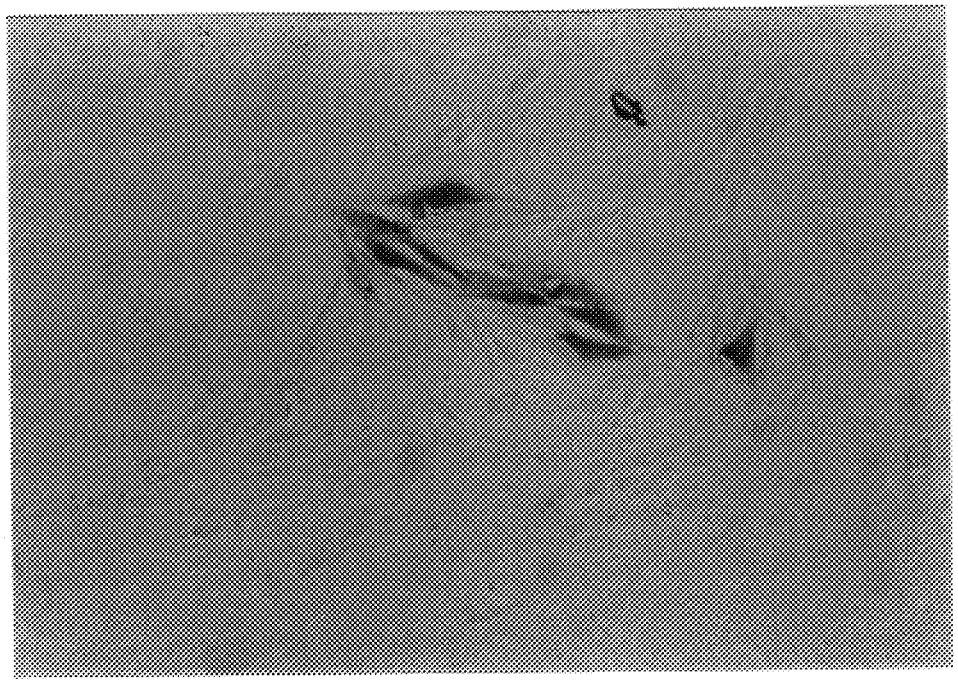
FIG._30A
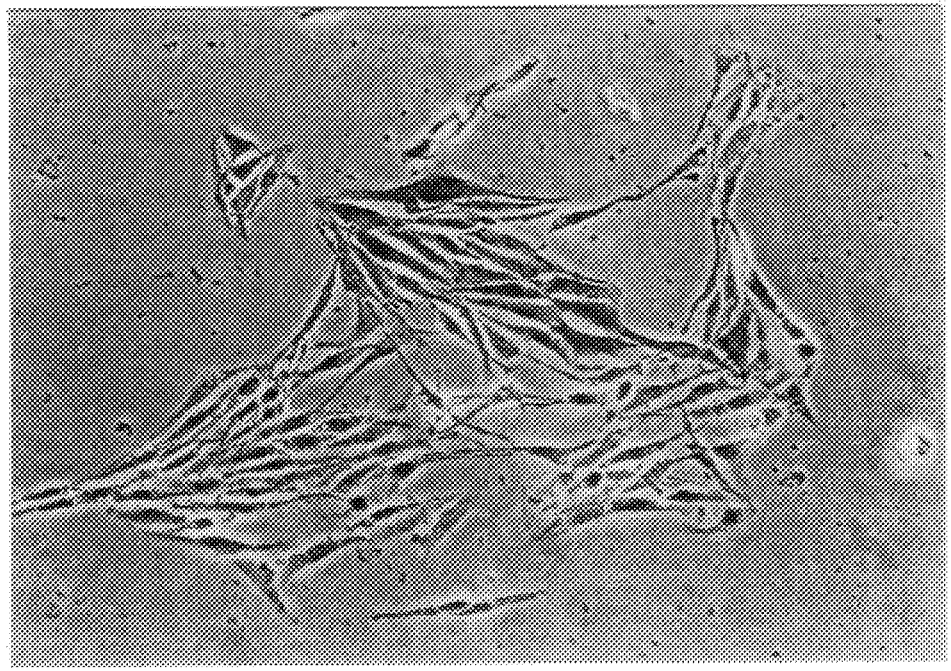
FIG._30B

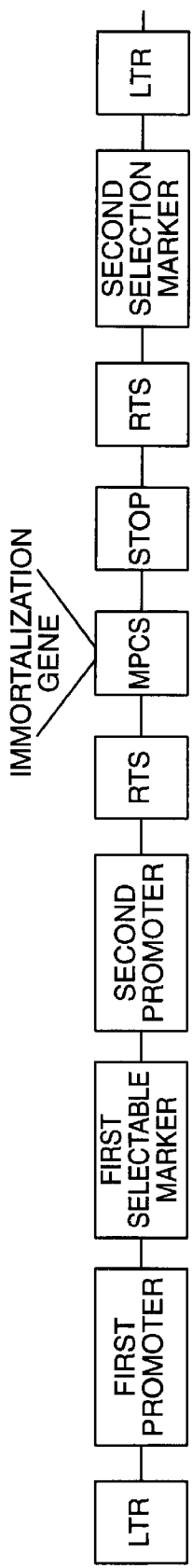
FIG._31A
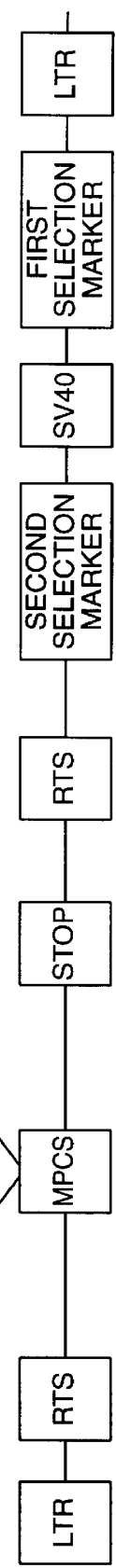
FIG._31B
FIG._31C
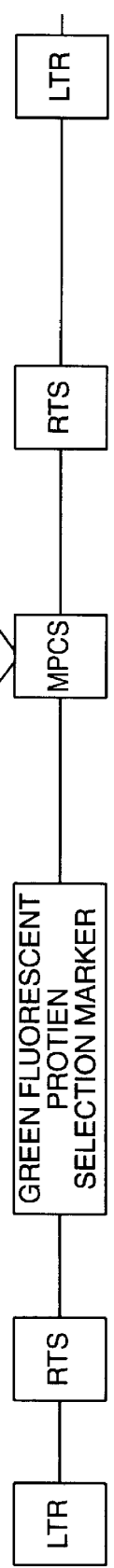
FIG._31D

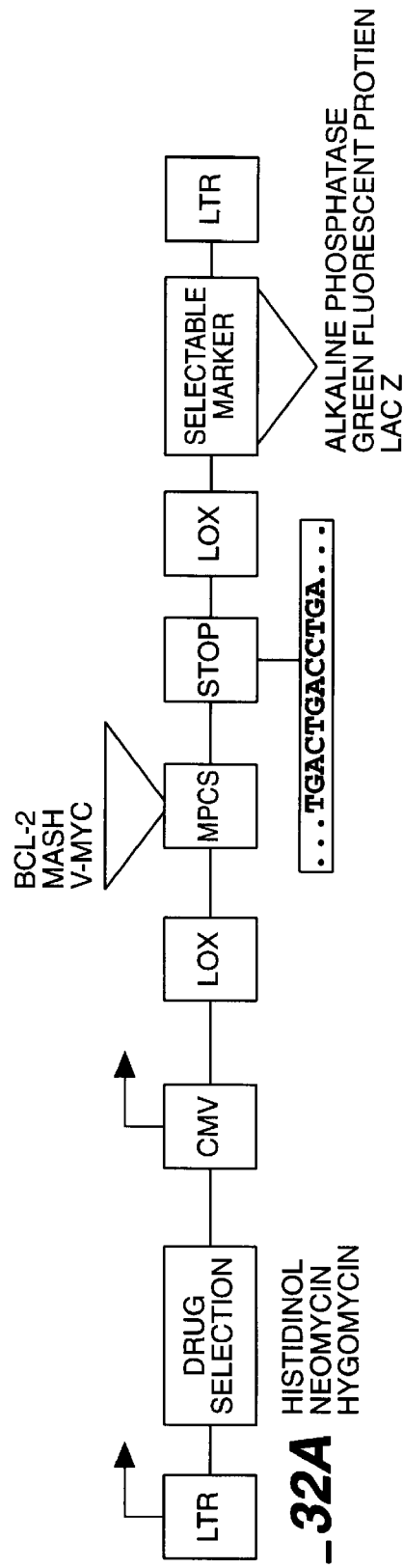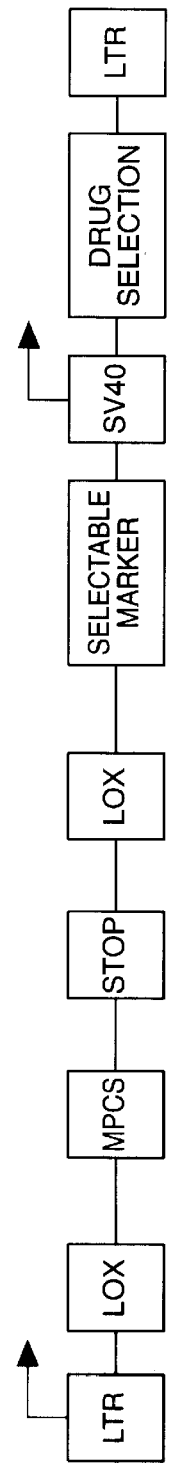
FIG._32A
FIG._32B

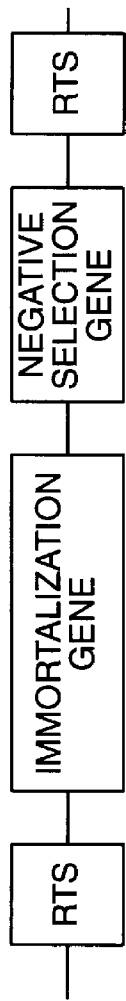
FIG._33A
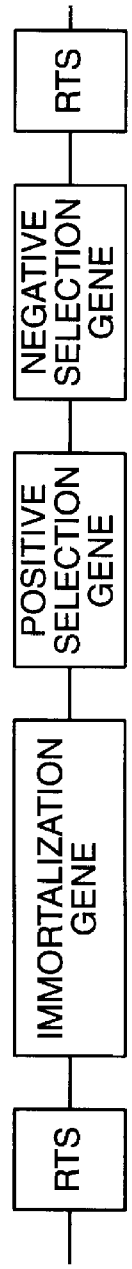
FIG._33B
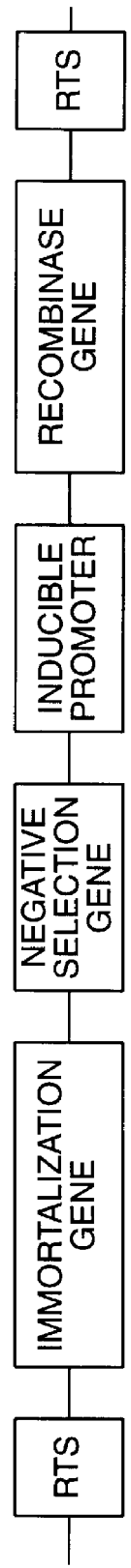
FIG._33C

FIG._34A
FIG._34B
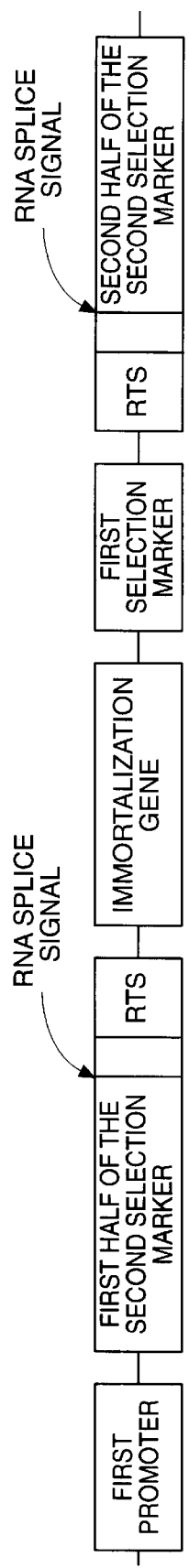
FIG._35

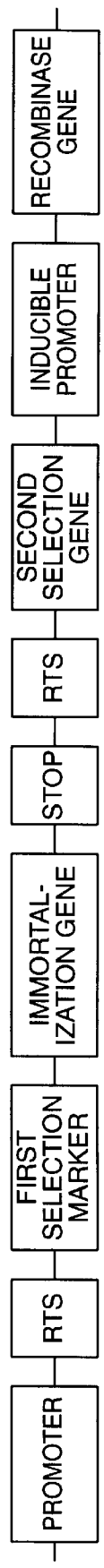
FIG._36A
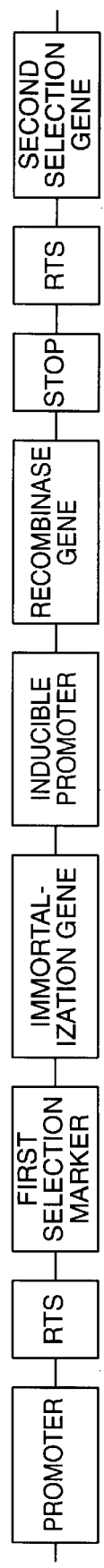
FIG._36B

MAMMALIAN MULTIPOTENT NEURAL STEM CELLS

This is a continuation-in-part of Ser. No. 08/188,286, filed Jan. 28, 1994, U.S. Pat. No. 5,654,183, which is a continuation-in-part of PCT application No. PCT/US93/07000, filed Jul. 26, 1993, which is a continuation-in-part of U.S. patent application Ser. No. 07/969,088, filed Oct. 29, 1992, now abandoned, which is a continuation-in-part of U.S. patent application Ser. No. 07/920,617, filed Jul. 27, 1992, now abandoned.

FIELD OF THE INVENTION

The invention relates to the isolation, regeneration, immortalization and use of mammalian multipotent neural stem cells and progeny thereof.

BACKGROUND

The neural crest is a transient embryonic precursor population, whose derivatives include cells having widely different morphologies, characteristics and functions. These derivatives include the neurons and glia of the entire peripheral nervous system, melanocytes, cartilage and connective tissue of the head and neck, stroma of various secretory glands and cells in the outflow tract of the heart (for review, see Anderson, D. J. (1989) Neuron 3:1–12). Much of the knowledge of the developmental potential and fate of neural crest cells comes from studies in avian systems. Fate maps have been established in aves and provide evidence that several different crest cell derivatives may originate from the same position along the neural tube (Le Dourain, N. M. (1980) Nature 286:663–669). Schwann cells, melanocytes and sensory and sympathetic neurons can all derive from the truncal region of the neural tube. On the other hand, some derivatives were found to originate from specific regions of the crest, e.g., enteric ganglia from the vagal and sacral regions. These studies also revealed that the developmental potential of the neural crest population at a given location along the neural tube is greater than its developmental fate. This suggests that the new environment encountered by the migrating crest cells influences their developmental fate.

Single-cell lineage analysis in vivo, as well as clonal analysis in vitro, have reportedly shown that early avian neural crest cells are multipotential during, or shortly after, their detachment and migration from the neural tube. In avian systems, certain clones derived from single neural crest cells in culture were reported to contain both catecholaminergic and pigmented cells (Sieber-Blum, M. et al. (1980) Dev. Biol. 80:96–106). Baroffio, A. et al. (1988) Proc. Natl. Acad. Sci. USA 85:5325–5329, reported that avian neural crest cells from the cephalic region could generate clones which gave rise to highly heterogeneous progeny when grown on growth-arrested fibroblast feeder cell layers.

In vivo demonstration of the multipotency of early neural crest cells was reported in chickens by Bronner-Fraser, M. et al. (1989) Neuron 3:755–766. Individual neural crest cells, prior to their migration from the neural tube, were injected with a fluorescent dye. After 48 hours, the clonal progeny of injected cells were found to reside in many or all of the locations to which neural crest cells migrate, including sensory and sympathetic ganglia, peripheral motor nerves and the skin. Phenotypic analysis of the labelled cells revealed that at least some neural crest cells are multipotent in vivo. Following migration from the neural tube, these early multipotent crest cells become segregated into different sublineages, which generate restricted subsets of differentiated derivatives. The mechanisms whereby neural crest cells become restricted to the various sublineages are poorly understood. The fate of neural crest derivatives is known to be controlled in some way by the embryonic location in which their precursors come to reside (Le Douarin, N. M. (1982) The Neural Crest., Cambridge University Press, Cambridge, UK). The mechanism of specification for neural crest cells derivatives is not known. In culture studies described above, investigators reported that clones derived from primary neural crest cells exhibited a mixture of phenotypes (Sieber-Blum, M. et al. (1980) ibid; Baroffio, A. et al. (1988) ibid; Cohen, A. M. et al. (1975) Dev. Biol. 46:262–280; Dupin, E. et al. (1990) Proc. Natl. Acad. Sci. USA 87:1119–1123). Some clones contained only one differentiated cell type whereas other clones contained many or all of the assayable crest phenotypes.

The observation that apparently committed progenitors and multipotent cells coexist in the neural crest may be interpreted to reflect a pre-existing heterogeneity in the population of primary crest cells or it may reflect asynchrony in a population of cells that undergoes a progressive restriction in developmental potential. Given the uncertainty in the art concerning the developmental potential of neural crest cells, it is apparent that a need exists for the isolation of neural crest cells in clonal cultures.

There have been several reports of the immortalization of nervous tissue (see Murphy et al., J. Neurobiol. 22(5):522–535 (1991); Bartlett et al., Proc. Natl. Acad. Sci. USA 85:3255–3259 (1988); Bernard et al., J. Neurosci. Res. 24:9–20 (1989); and WO 89/03872). However, none of these references show the creation of a peripherial-nervous system (PNS)-derived stem cell line which can be propagated in an undifferentiated form and then induced to differentiate in a controlled manner to both neurons and glia. Rather, the references show immortalization of partially or fully differentiated cells, or undifferentiated cells whose origin is either unclear or derived from the central-nervous system (CNS).

In addition, although culture systems have been established which allow the growth and differentiation of isolated avian neural crest cells thereby permitting phenotypic identification of their progeny, culture conditions which allow the self-renewal of multipotent mammalian neural crest cells have not been reported. Such culture conditions are essential for the isolation of mammalian neural crest stem cells. Such stem cells are necessary in order to understand how multipotent neural crest cells become restricted to the various neural crest derivatives. In particular, culture conditions which allow the growth and self-renewal of mammalian neural crest stem cells are desirable so that the particulars of the development of these mammalian stem cells may be ascertained. This is desirable because a number of tumors of neural crest derivatives exist in mammals, particularly humans. Knowledge of mammalian neural crest stem cell development is therefore needed to understand these disorders in humans. Additionally, the ability to isolate and grow mammalian neural crest stem cells in vitro allows for the possibility of using said stem cells to treat peripheral neurological disorders in mammals, particularly humans.

Accordingly, it is an object herein to provide clonal cultures of mammalian multipotent neural stem cells and their progeny in feeder cell-independent cultures. Another object of the invention is directed to the demonstration that multipotential stem cells exist in the neural crest. Another object of the invention is the demonstration that these multipotent neural crest stem cells have at least limited self regeneration capacity and undergo lineage restriction in a manner that is sensitive to the local environment.

A further object of the invention is to provide methods which allow the growth and regeneration of multipotent neural stem cells in feeder cell-independent cultures. Another object of the invention is to provide methods which allow the differentiation of multipotent neural crest stem cells into at least the progenitors for, as well as, more differentiated neurons and glia of the peripheral nervous system (PNS). A further object of the invention is to provide methods which allow for the identification of mammalian multipotent neural stem cells using transplantation assays. Still further, an object of the invention is to provide methods for transplanting neural crest stem cells or their progeny into a mammal.

A further object of the invention is to extend the above methods to provide clonal cultures of mammalian neural crest stem cells and their progeny, to the detection or purification of glial or neuronal progenitor cells, and to provide methods which allow the growth, regeneration and differentiation of such cells from tissues other than the embryonic neuronal crest. Still further, it is an object herein to provide methods for transplanting progenitors of such glial and neuronal cells and multipotent stem cell precursor thereof into a mammal.

A further object of the invention is to provide cultures of genetically-engineered multipotent neural stem cells and their progeny. Specifically, it is an object of the invention to provide for immortalized multipotent neural stem cells derived from the PNS and neural crest stem cells, derived from the PNS. Still further, an object of the invention is to provide methods for the generation of cultures of such genetically-engineered multipotent neural stem cells and their progeny including methods for immortalizing such cells.

An additional object of the invention is to provide immortalized neural crest stem cells which may be propagated in an undifferentiated state and then induced to differentiate in a controlled manner to both neurons and glia with high efficiency. Still further, an object of the invention is to provide culture conditions which allow the controlled differentiation of stem cells into either neurons or glia, or both.

Further, an object of the invention is to provide monoclonal antibodies capable of recognizing surface markers which characterize multipotent neural stem cells and/or their progeny. A further object is to provide a novel procedure for screening sera and hybridomas for such antibodies.

It is a further object of the invention to provide methods for assaying the effects of various substances on neural stem cells. Such effects include the differentiation of said cells into neurons, glia or smooth muscle cells.

In addition, it as an object of the invention to provide methods for producing mammalian smooth muscle cells including methods which result in the preferential differential to smooth muscle cells at the expense of other cell lineages.

SUMMARY OF THE INVENTION

In accordance with the forgoing objects, the invention includes the isolation, clonal expansion and differentiation of mammalian multipotent neural stem cells such as those derived from the neural crest. The methods employ novel separation and culturing regimens and bioassays for establishing the generation of multipotent neural stem cells and their derivatives. These methods result in the production of non-transformed neural stem cells and their progeny. The invention demonstrates, at the clonal level, the self regeneration and asymmetrical division of mammalian neural stem cells for the first time in feeder cell-independent cultures. Lineage restriction is demonstrated within a developing clone and is shown to be sensitive to the local environment. For example, neural crest stem cells cultured on a mixed substrate of poly-D-lysine and fibronectin generate PNS neurons and glia, but on fibronectin alone the stem cells generate PNS glia but not neurons. The neurogenic potential of the neural crest stem cells, while not expressed, is maintained over time on fibronectin. Therefore, both the overt differentiation and maintenance of a latent developmental potential of neural crest stem cells are shown to be sensitive to the environment. The invention further includes transplantation assays which allow for the identification of mammalian multipotent neural stem cells from various tissues. It also includes methods for transplanting mammalian neural stem cells and/or neural or glial progenitors into mammals.

The invention also provides methods for obtaining a cellular composition from mammalian tissue comprising one or more cells having at least one property characteristic of a glial or neural progenitor cell or a multipotent stem cell precursor of such cells. The method comprises preparing a suspension comprising a population of cells from a mammalian tissue; contacting the cell suspension with a culture medium and substrate which permits self-renewal of one or more of the glial or neural progenitor cells or multipotent stem cell precursor, if present, in the cell suspension; and identifying one or more such cells by its ability to self-renew and differentiate feeder-cell independent culture.

The invention also includes alternate methods for obtaining a cellular composition comprising one or more cells having at least one property characteristic of a glial or neural progenitor cell or a multipotent stem cell precursor thereof. The method comprises preparing a suspension comprising cells from a mammalian tissue; contacting the suspension with an antibody capable of forming a complex with a neural cell-specific surface marker on said glial or neural progenitor cells or multipotent stem cell precursor; and isolating the complex, if formed, to obtain said cellular composition.

The invention is also directed to cells made according to any of the foregoing methods.

The invention also includes cultures of genetically-engineered mammalian multipotent neural stem cells and their progeny. Nucleic acid sequences encoding genes of interest are introduced into multipotent neural stem cells where they are expressed. These genes can include neurotrophic or survival factors and immortalizing oncogenes. In addition, marker genes, such as the $E.$ $coli$ $\beta$-galactosidase gene, can be introduced to provide neural stem cells and their progeny which can be identified based on the expression of the marker gene. Selectable marker genes, such as the neomycin phosphoribosyltransferase (neomycin-resistance, neo$^r$) or hisD genes, may be introduced to provide for a population of genetically-engineered stem cells which are identified by the ability to grow in the presence of selective pressure (i.e., medium containing neomycin or L-histidinol). Neural stem cells may be transfected (genetically-engineered) with both a selectable marker and a non-selectable marker to provide neural stem cells which express both gene products.

The invention also includes methods for producing cultures of genetically-engineered mammalian multipotent neural stem cells and their progeny.

Still further, the invention includes methods for immortalizing such cell lines by transfecting a glial or neural progenitor cell or multipotent stem cell precursor thereof with a vector comprising at least one immortalizing gene.

Further, the invention includes monoclonal antibodies capable of recognizing surface markers characteristic of mammalian multipotent neural stem cells and their progeny. The invention also includes a method for screening hybridoma producing such monoclonal antibodies which comprises contacting live neural cells with monoclonal antibodies from a hybridoma and detecting whether the monoclonal antibody binds to the neural cell.

In addition to the foregoing, the invention includes methods for assaying the effects of substances on neural stem cells. Such methods comprise contacting a culture of at least one neural stem cell with a substance and determining the effect, if any, of the substance on the differentiation of the neural stem cell. Such differentiation can be to neurons, glial or smooth muscle cells or a combination thereof.

The invention also includes methods for producing mammalian smooth muscle cells comprising culturing at least one mammalian neural stem cell under conditions which permit differentiation to smooth muscle cells. Such conditions can result in a heterogeneous population which includes smooth muscle cells and neurons and/or glia. In alternate embodiments, factors instructive for smooth muscle differentiation are used which result in the preferential differentiation to smooth muscle at the expense of other cell lineages.

BRIEF DESCRIPTION OF THE DRAWINGS

The file of this patent contains at least one drawing executed in color. Copies of this patent with color drawing (s) will be provided by the Patent and Trademark Office upon request and payment of necessary fee.

FIG. 1A depicts the migration of rat neural crest cells from the neural tube.

FIG. 1B demonstrates the expression of LNGFR and nestin by neural crest cells.

FIGS. 1C and 1D show the FACS profile from neural crest cells stained with anti-LNGFR (1D) and a control showing the background staining of the secondary antibody (1C).

FIG. 2 demonstrates the clonal expansion of LNGFR$^+$, nestin$^+$ rat neural crest cells.

FIG. 3 is a flow chart summarizing experiments demonstrating the multipotency of mammalian neural crest cells.

FIG. 4 demonstrates the expression of neuronal traits in clones derived from LNGFR$^+$ founder cells.

FIG. 5 demonstrates the expression of Schwann cell phenotype by neural crest-derived glia.

FIG. 6 shows the expression of peripherin, GFAP, and $O_4$ in a clone derived from a LNGFR$^+$ founder cell.

FIG. 7 is a flow chart summarizing experiments demonstrating the self-renewal of mammalian neural crest cells.

FIG. 8 demonstrates the self-renewal of multipotent neural crest cells.

FIG. 9 demonstrates the multipotency of secondary founder cells.

FIG. 10 provides a flow chart summarizing experiments demonstrating the substrate effect on the fate of mammalian neural crest cells.

FIG. 11 demonstrates that the neuronal differentiation of multipotent neural crest cells is affected by their substrate.

FIG. 12 summarizes the percentage of different clone types which result when founder cells are grown on either FN or FN/PDL substrates.

FIG. 13 provides a flow chart summarizing experiments demonstrating the instructive effect of the substrate on neural crest cell fate.

FIG. 14 summarizes the percentage of the different clone types which result when founder cells are treated with a PDL lysine overlay at 48 hours (panel A) or day 5 (panel B).

FIG. 15 demonstrates the genetic-engineering of a multipotent neural stem cell. Panel A depicts the expression of $E.\ coli$ β-galactosidase (lacZ) in neural crest stem cells following infection with a lacZ-containing retrovirus. β-galactosidase$^+$ cells are indicated by the solid arrows. Panel B depicts neural crest stem cells in phase contrast, in the same microscopic field as shown in Panel A. Cells which do not express β-galactosidase are indicated by open arrows.

FIG. 16 demonstrates the specificity of a supernatant from a hybridoma culture producing monoclonal antibody specific to mouse LNGFR. Supernatants were screened using live Schwann cells isolated from mouse sciatic nerve. Panel A shows that most cells are stained with anti-LNGFR antibody (red staining; open arrows). Panel B shows Schwann cell nuclei counter stained with DAPI. Comparison with Panel A reveals a few cells not labeled by anti-LNGFR antibody (blue staining; open arrows).

FIGS. 17A and B depict the identification of smooth muscle cells in neural crest cultures. Cultures of neural crest stem cells were fixed and double-labeled with antibodies to p75-LNGFR (FIG. 17B, orange staining), and SMA (FIG. 17B, green staining). The cultures were also labeled with DAPI, a nuclear dye (FIG. 17B, blue ovals). A phase contrast image of the microscopic field is shown in FIG. 17A. Note that the p75+ cells (FIG. 17B, solid arrow) do not express SMA< whereas the SMA+ cells (FIG. 17B, open arrows) do not express p75.

FIGS. 18A and B demonstrate that individual neural cres cells can generate neurons, glia and smooth muscle cells. The figures illustrate three views of a clone derived from a single p75+ neural crest founder cell, grown for two weeks in standard medium. A neuron is identifiable in the clone by virtue of peripherin expression (FIG. 18B, arrowhead) and long neurites (FIG. 18A). Glia are identifiable by GFAP expression (FIG. 18C, orange staining, open arrows), and a smooth muscle cell is identified by staining with anti-SMA (FIG. 18C, green staining, closed arrow). Nuclei of all cells have been labeled blue with DAPI (FIG. 18C).

FIGS. 19A, B and C demonstrate that smooth muscle cell differentiation is promoted by fetal bovine serum. Shown are three views of a colony of neural crest cells grown in 5% fetal bovine serum. These cells do not express p75-LNGFR under these conditions. Cells visible by phase-contrast (FIG. 19A) express both SMA (FIG. 19B, red staining) and also desmin (FIG. 19C, green staining).

FIGS. 20A and B demonstrate that neural crest-derived smooth muscle cells express calponin. The culture is similar to that in FIG. 19, except the cells were doubly-labeled with anti-SMA (FIG. 20B, red staining) and calponin (FIG. 20B, green staining). Cells that co-express both markers stain orange due to blending of the two colors (FIG. 20B).

FIGS. 21A, B and C demonstrates that mouse neural crest cells in culture express LNGFR and nestin. A 24 hour explant of mouse neural crest was fixed and surface-laelled using a rat monoclonal anti-LNGFR antibody (A: upper panel), counter-stained with anit-nestin monoclonal antibody (B: middle panel) and labeled with DAPI to reveal all cell nuclei in the microscopic field (C: lower panel). The same field is shown with rhodamine (A: upper), fluorescein (B: middle) and ultraviolet (C: lower) filters. The dense mass of cells in the lower left (C: lower panel) is the neural tube, which does not express LNGFR (A: upper).

FIGS. 22A, B, C and D demonstrates that individual mouse neural crest cells can generate both neurons and glia.

A single mouse neural crest cell (A: upper, right panel) was identified and stained with anti-LNGFR (B: upper, left panel) shortly after plating. Following several days of growth in culture, the clone produced by this founder cell was fixed and doubly-labeled with antibody to peripherin (C: middle panel, orange staining) to detect neurons, and GFAP (C:middle panel, green staining) to detect glial cells. D: lower panel shows the same filed as the middle panel, stained with DAPI to reveal all cell nuclei.

FIGS. 23A, B, C and D demonstrate that myc-1 cells express LNGFR and nestin. A and B (upper): A:(upper left) phase-contrast and B: (upper right) fluorescent micrographs of a field of myc-1 cells stained with anti-LNGFR. All cells in the field are positive. C and D (lower): a field of myc-1 cells fixed and doubly-stained with anti-LNGFR (C: left) and nestin (D:right) antibodies. Note that all cells are stained by both antibodies.

FIGS. 24A, B, C and D demonstrate that myc-1 cells do not express neuronal and glial lineage markers. Myc-1 cells grown in standard medium on fibronectin were surface-labeled with anti-LNGFR (left panels, A and C), fixed and ocunter-stained with anti-peripherin (B: upper right) or anti-GFAP (D, lower right). Neither marker is expressed by the cells. Similar results were obtained with antibody to smooth muscle actin (not shown).

FIGS. 25A, B, C and D demonstrate that myc-1 cells can differentiate to postmitotic neurons. Myc-1 cells were grown either on fibronectin, to maintain them in an undifferentiated state (A and B, upper panels), or transferred to fibronectin/poly-D-lysine and seum/forskolin-containing medium to promote differentiation (C and D, lower panels). After several days of growth under the two conditions, the cells were pulsed with BrdU for 24 hours, then fixed and stained with anti-BrdU antibody. Left panels A and C show all nuclei labeled with DAPI. Under the undifferentiated conditions, all nuclei are labeled with BrdU (B, upper right). Under differentiation-promoting conditions, only some of the nuclei are labeled (D, lower right). In addition the cells exhibit a neuronal morphology and express peripherin, a neuron-specific marker (green staining, lower right).

FIG. 26A, B, C and D demonstrate that myc-1-derived neurons express NCAM and neurofilament. After growth under differentiation-promoting conditions (FIG. 25), myc-1 cells were fixed and doubly-labeled with anti-peripherin antibody (B and D, right panels) and either anti-NCAM (A, upper left) or neurofilament (C, lower left). Note that all neurons express both markers.

FIGS. 27A, B, C and D demonstrate that myc-1 cells also differentiate to glia. Cells grown under differentiation-promoting conditions were fixed and doubly-labeled with antibody to GFAP (A and C, left panels) and iether anti-LNGFR (B, upper right) or O4 (D, lower right). An LNGFR+, GFAP+ phenotype is characteristic of immature Schwann cells; more mature Schwann cells express O4 as well.

FIGS. 28A and B demonstrate that individual myc-1 cells can differentiate to both neurons and glia. Shown is a clone of cells derived from an individual, identified myc-1 founder cell grown under differentiation-promoting conditions for several days. The clone was fixed and triply labeled for peripherin (A, upper panel, orange staining), GFAP (A, upper panel, green staining), and DAPI (B: lower panel).

FIGS. 29A, B, C and D demonstrate a high proportion of myc-1 cells are multipotent. Myc-1 cells were plated at low density and grown under differentiation-promoting conditions for several days. The cultures were then fixed and stained with anti-peripherin and developed using an HRP-conjugated secondary antibody. The brown reaction product identifies the neurons (A, C and D: upper left and lower panels); the non-neuronal cells (glial cells) can be seen in phase contrast illumination (D, lower right). The graph (B, upper right) indicates that the majority of colonies in a field contain both neurons and other ("O") non-neuronal cells.

FIGS. 30A and B demonstrate that myc-1 cells can be further genetically modified. Myc-1 cells were grown under standard conditions and infected with a replication incompetent, recombinant retroviral vector ("BAG") harboring the lacZ gene. After several days the cells were fixed and stained for lacZ expression using the Xgal reagent. Blue cells express the introduced lacZ gene.

FIGS. 31A, 31B, 31C and 31D depict the design of four vectors for conditional immortalization. RTS is a recombinase target site. MPCS is a multiple polylinker cloning site, into which an immortalization gene is inserted. STOP is a translation or transcription stop sequence. LTR is a viral long terminal repeat. SV40 is the promoter from SV40.

FIGS. 32A and 32B depict preferred embodiments. FIG. 32(A) and 32(B) are two alternative designs for the same basic vector. In both vectors, the oncogene coding sequences (v-myc, BCI-2, or MASH-1) are inserted into a multiple polylinker cloning site (MPCS) flanked by RTSs, i.e. loxP sites. Downstream of the MPCS there is a "STOP" sequence designed to prevent translation of a downstream selectable marker (alkaline phosphatase, green fluorescent protein, lacZ, etc.). There is also a drug selection maker to select for initial immortalization of the cells. The drug-selection maker is driven by the viral LTR and the oncogene by an internal promoter-enhancer (32A) or vice-versa (32B).

FIGS. 33A, 33B and 33C depict immortalization/disimmortalization constructs using negative selection markers to insure that all cells have been disimmortalized. FIG. 33A utilizes the immortalization gene as the selection marker for transformation; alternatively, clonal analysis using exposure to a negative selection agent can serve as the marker for transformation. FIG. 33B uses a positive selection marker as the marker for transformation. The positive and negative selection marker genes may be located in any order. FIG. 33C adds a recombinase under the control of an inducible promoter; a positive selection gene may also be added. Again, these genes may be located in any order. The promoters for transcription of genes other than the recombinase are not depicted, as they may be located at a variety of locations.

FIGS. 34A and 34B depict the use of two different recombinases and RTSs. FIG. 34A allows the expression of the immortalization gene and first selection marker gene, with the second selection marker gene not expressed until excision between the two RTSls. Upon RTS 1 excision, the second selection marker gene is expressed, allowing selection for disimmortalized cells. Prior to transplantation, exposure to the recombinase recognizing RTS 2 excises the second selection marker, thus minimizing the exogeneous nucleic acid. FIG. 34B is similar, except that an exogeneous gene is included, for example, encoding a therapeutic agent. Thus, cells may be transplanted with the exogeneous gene expressed, and at some later time the patient is exposed to the second recombinase to remove the exogeneous gene.

FIG. 35 depicts a conditional immortalization construct which avoids the use of a STOP site by putting the RTSs in the middle of a selection marker gene. Upon transformation of cells with this construct, the immortalization gene and first selection marker gene are transcribed, using a second promoter. Immortalized cells are then selected for on the basis of the first selection marker. Upon exposure to a recombinase that recognizes the RTSs, the immortalization gene and first selection marker are excised, along with the one of the RTS sites The second selection marker is transcribed, with the second RTS being removed as a result of RNA splice signals which are recognized by the cellular machinery of the host cells. This allows the second selection marker gene to be transcribed.

FIGS. 36A and 36B depict the use of an inducible promoter with the recombinase gene. FIGS. 36A and 36B correspond to the construct depicted in FIG. 31C, but with a recombinase gene under the control of an inducible promoter. FIG. 36A depicts a construct which will leave the recombinase gene in the genome after excision, and FIG. 36B depicts a construct which eliminates the recombinase gene.

DETAILED DESCRIPTION OF THE INVENTION

The invention is directed, in part, to the isolation and clonal propagation of non-transformed mammalian neural crest stem cells and to multipotent neural stem cells from other embryonic and adult tissue. The invention also includes the production of neural crest stem cell and multipotent neural stem cell derivatives including progenitor and more differentiated cells of the neuronal and glial lineages. The invention is illustrated using neural crest stem cells isolated from the rat and mouse. The invention, however, encompasses all mammalian neural crest stem cells and multipotent neural stem cells and their derivatives and is not limited to neural crest stem cells from the rat or mouse. Mammalian neural crest stem cells and multipotent neural stem cells and their progeny can be isolated from tissues from human and non-human primates, equines, canines, felines, bovines, porcines, lagomorphs, etc.

The invention encompasses several important methodological innovations: 1) the use of monoclonal antibodies to the low-affinity Nerve Growth Factor Receptor (LNGFR) as a cell surface marker to isolate and identify neural crest stem cells, a method extensible to other neural stem cell populations as well; 2) the development of cell culture substrates and medium compositions which permit the clonal expansion of undifferentiated neural crest cells; 3) the development of culture substrates and medium compositions which permit the differentiation of mammalian neural crest cells into their differentiated derivatives (including but not restricted to peripheral neurons and glia) in clonal culture; 4) the immortalization of undifferentiated neural crest cells; and 5) the conditional immortalization of undifferentiated neural crest cells such that the cells may be disimmortalized prior to or after differentiation.

The invention also provides neural crest stem cells and other multipotent neural stem cells. It is important to understand that such cells could not be identified as stem cells without the development of the isolation and cell culture methodologies summarized above. The identification of a neural stem cell requires that several criteria be met: 1) that the cell be an undifferentiated cell capable of generating one or more kinds of differentiated derivatives; 2) that the cell have extensive proliferative capacity; 3) that the cell be capable of self-renewal or self-maintenance (Hall et al. (1989) *Development* 106:619; Potten et al. (1990) *Crypt. Development* 110:1001). The concept of a stem cell as obligatorily capable of "unlimited" self-renewal is applicable only to regenerating tissues such as skin or intestine.

In the case of a developing embryo stem cells may have limited self-renewal capacity but be stem cells nevertheless (Potten et al. (1990) supra). The development of clonal culture methods permitted the demonstration of criteria 1 and 2 herein. The development of sub-clonal culture methods (i.e., the ability to clone single neural stem cells, and then re-clone progeny cells derived from the original founder cell) further permitted the demonstration herein of criterion 3.

To appreciate the significance of this demonstration, consider an alternative hypothesis for cells from the neural crest: individual undifferentiated neural crest cells divide to generate both neurons and glia (i.e., meet criteria 1 and 2 above), but the daughter cells produced by these initial cell divisions are committed to producing either neurons or glia, but not both. In this case, the neural crest cell is a progenitor cell but not a stem cell, because it does not have self-renewal capacity. If this were the case, then upon sub-cloning of neural crest cell clones, the resulting "secondary" clones could contain either neurons or glia, but not both. This is not observed. Rather, most or all of the secondary clones contain both neurons and glia, like their parent clones. This experiment thus provides the first definitive evidence that neural progenitor cells from any region of the nervous system have stem cell properties. In no other set of published experiments have these stringent criteria for stem cell properties been met, despite claims that "stem cells" have been isolated or identified (Cattaneo et al. (1991) *Trends Neurosci.* 14:338; Reynolds et al. (1992) *Science* 255:1707) from the mammalian central nervous system. This in part reflects imprecise use of the term "stem cell" and in part the failure to perform adequate experimental tests to support the existence of such cells.

As used herein, the term "non-transformed cells" means cells which are able to grow in vitro without the need to immortalize the cells by introduction of a virus or portions of a viral genome containing an oncogene(s) which confers altered growth properties upon cells by virtue of the expression of viral genes within the transformed cells. These viral genes typically have been introduced into cells by means of viral infection or by means of transfection with DNA vectors containing isolated viral genes.

As used herein, the term "genetically-engineered cell" refers to a cell into which a foreign (i.e., non-naturally occurring) nucleic acid, e.g., DNA, has been introduced. The foreign nucleic acid may be introduced by a variety of techniques, including, but not limited to, calcium-phosphate-mediated transfection, DEAE-mediated transfection, microinjection, retroviral transformation, protoplast fusion and lipofection. The genetically-engineered cell may express the foreign nucleic acid in either a transient or long-term manner. In general, transient expression occurs when foreign DNA does not stably integrate into the chromosomal DNA of the transfected cell. In contrast, long-term expression of foreign DNA occurs when the foreign DNA has been stably integrated into the chromosomal DNA of the transfected cell. In addition, stably integrated DNA may be transiently expressed in the sense that it may be later excised using the recombinase system disclosed herein, which can result in all or part of the foreign DNA being excised.

As used herein, an "immortalized cell" means a cell which is capable of growing indefinitely in culture due to the introduction of an "immortalizing gene(s)" which confers altered growth properties upon the cell by virtue of expression of the immortalizing gene(s) within the genetically engineered cell. Immortalizing genes can be introduced into cells by means of viral infection or by means of transfection with vectors containing isolated viral nucleic acid encoding one or more oncogenes. Viruses or viral oncogenes are selected which allow for the immortalization but preferably not the transformation of cells. Immortalized cells preferably grow indefinitely in culture but do not cause tumors when introduced into animals. An immortalized cell may be immortalized in several ways. In one embodiment, the cell is transiently or stably transformed with a foreign gene, such as an oncogene, which results in immortalization. In the preferred embodiment, the cell is transformed with an oncogene in such a manner that the cell may later be disimmortalized, for example by using the recombinase system disclosed herein. Thus, a cell may be immortalized for cloning and maintenance, but disimmortalized prior to introduction into an animal or patient.

As used herein, the term "transformed cell" refers to a cell having the properties of 1) the ability to grow indefinitely in culture and 2) causing tumors upon introduction into animals. In some embodiments, "transformed cell" refers to a cell which has been conditionally immortalized, i.e. one which is capable of being subsequently disimmortalized. "Transformation" generally refers to the process of introducing DNA into a cell; however, as one skilled in the art will recognize, transformation may also refer to the generation of a transformed cell.

As used herein, the term "feeder-cell independent culture" or grammatical equivalents means the growth of cells in vitro in the absence of a layer of different cells which generally are first plated upon a culture dish to which cells from the tissue of interest are added. The "feeder" cells provide a substratum for the attachment of the cells from the tissue of interest and additionally serve as a source of mitogens and survival factors. The feeder-cell independent cultures herein utilize a chemically defined substratum, for example fibronectin (FN) or poly-D-lysine (PDL) and mitogens or survival factors are provided by supplementation of the liquid culture medium with either purified factors or crude extracts from other cells or tissues. Therefore, in feeder-cell independent cultures, the cells in the culture dish are primarily cells derived from the tissue of interest and do not contain other cell types required to support the growth of the cells derived from the tissue of interest.

As used herein, the term "clonal density" means a density sufficiently low enough to result in the isolation of single, non-impinging cells when plated in a culture dish, generally about 225 cells/100 mm culture dish.

As used herein, the term "neural crest stem cell" means a cell derived from the neural crest which is characterized by having the properties (1) of self-renewal and (2) asymmetrical division; that is, one cell divides to produce two different daughter cells with one being self (renewal) and the other being a cell having a more restricted developmental potential, as compared to the parental neural crest stem cell. The foregoing, however, is not to be construed to mean that each cell division of a neural crest stem cell gives rise to an asymmetrical division. It is possible that a division of a neural crest stem cell can result only in self-renewal, in the production of more developmentally restricted progeny only, or in the production of a self-renewed stem cell and a cell having restricted developmental potential. The neural crest gives rise to the peripheral nervous system (PNS).

As used herein, the term "multipotent neural stem cell" refers to a cell having properties similar to that of a neural crest stem cell but which is not necessarily derived from the neural crest. Rather, as described hereinafter, such multipotent neural stem cells can be derived from various other tissues including neural epithelial tissue from the brain and/or spinal cord of the adult or embryonic central nervous system or neural epithelial tissue which may be present in tissues comprising the peripheral nervous system. In addition, such multipotent neural stem cells may be derived from other tissues such as lung, bone and the like utilizing the methods disclosed herein. In a preferred embodiment, multipotent neural stem cells are derived from the PNS, such as from the neural crest, and not from the CNS. It is to be understood that such cells are not limited to multipotent cells but may comprise a pluripotent cell capable of regeneration and differentiation to different types of neurons and glia, e.g., PNS and CNS neurons and glia or progenitors thereof. In this regard, it should be noted that the neural crest stem cells described herein are at least multipotent in that they are capable, under the conditions described, of self-regeneration and differentiation to some but not all types of neurons and glia in vitro. Thus, a neural crest stem cell is a multipotent neural stem cell derived from a specific tissue, i.e., the embryonic neural tube.

In most embodiments, neural crest stem cells are further characterized by a neural cell-specific surface marker. Such surface markers in addition to being found on neural chest stem cells may also be found on other multipotent neural stems derived therefrom, e.g., glial and neuronal progenitor cells of the peripheral nervous system (PNS) and central nervous system (CNS). An example is the cell surface expression of a nerve growth factor receptor on neural crest stem cells. In rat, humans and monkeys this nerve growth factor receptor is the low-affinity nerve growth factor receptor (LNGFR). Such stem cells may also be characterized by the expression of nestin, an intracellular intermediate filament protein. Neural crest stem cells may be further characterized by the absence of markers associated with mature PNS neuronal or glial cells. In the rat, such markers include sulfatide, glial fibrillary acidic protein (GFAP) and myelin protein $P_o$ in PNS glial cells and peripherin and neurofilament in PNS neuronal cells.

LNGFR is a receptor for nerve growth factor, a neurotrophic factor shown to be responsible for neuronal survival in vivo. LNGFR is found on several mammalian cell types including neural crest cells and Schwann cells (glial cells of the PNS) as well as on the surface of cells in the ventricular zone throughout the embryonic central nervous systems. (See, e.g., Yan et al. (1988) *J. Neurosci.* 8:3481–3496 and Heuer, J. G et al. (1980) *Neuron* 5:283–296 which studied such cells in the rat and chick systems, respectively.) Antibodies specific for LNGFR have been identified for LNGFR from rat monoclonal antibodies 217c (Peng, W. W. et al. (1982) *Science* 215:1102–1104) and 192-Ig (Brockes, J. P. et al. (1977) *Nature* 266:364–366 and Chandler, C. E. et al. (1984) *J. Biol. Chem.* 259:6882–6889) and human (Ross, A. H. et al. (1984) *Proc. Natl. Acad. Sci. USA* 81:6681–6685; Johnson, et al. (1986) *Cell* 47:545–554; Loy et al. (1990) *J. Neurosci Res.* 27:651–644). The monoclonal antibody against human LNGFR has been reported to cross-react with LNGFR from monkeys (Mufson, E. G. et al. (1991) *J. Comp. Neurol.* 308:555–575). The DNA sequence has been determined for rat and human LNGFR (Radeke, M. J. et al. (1987) *Nature* 325:593–597 and Chao, M. V. et al. (1986) *Science* 232:518–521, respectively) and is highly conserved between rat and human.

Using the following techniques, monoclonal antibodies specific for LNGFR from any desired mammalian species are generated by first isolating the nucleic acid encoding the LNGFR protein. One protocol for obtaining such nucleic acid sequences uses one or more nucleic acid sequences from a region of the LNGFR gene which is highly conserved between mammalian species, e.g., rat and human, as a hybridization probe to screen a genomic library or a cDNA library derived from mammalian tissue from the desired species (Sambrook, J. et al. (1989) Cold Spring Harbor Laboratory Press. *Molecular Cloning: A Laboratory Manual,* 2nd Ed., pp. 8.3–8.80, 9.47–9.58 and 11.45–11.55). The cloned LNGFR sequences are then used to express the LNGFR protein or its extracellular (ligand binding) domain in an expression host from which the LNGFR protein is purified. Purification is performed using standard techniques such as chromatography on gel filtration, ion exchange or affinity resins. The purified LNGFR is then used to immunize an appropriate animal (e.g., mouse, rat, rabbit, hamster) to produce polyclonal antisera and to provide spleen cells for the generation of hybridoma cell lines secreting monoclonal antibodies specific for LNGFR of the desired species (Harlow, E. et al. (1988) Cold Spring Harbor Laboratory Press, *Antibodies: A Laboratory Manual, pp.* 139–242).

A novel screening method can be used to detect the production of antibody against LNGFR or any other surface marker which characterizes a multipotent neural stem cell or progeny thereof. The method can be practiced to detect animals producing polyclonal antibodies against a particular antigen or to identify and select hybridomas producing monoclonal antibodies against such antigens. In this method, serum from an immunized animal or supernatant from a hybridoma culture is contacted with a live neural cell which displays a surface marker characteristic of a particular neural cell line. Detection of whether binding has occurred or not is readily determined by any number of known methods. A particularly preferred method is to use labeled antibody which is specific for the immunoglobulins produced by the species which is immunized with the particular antigen and which is a source for polyclonal serum and spleen cells for hybridoma formation.

The live neural cell used in the foregoing antibody assay is dependent upon the particular surface marker for which an antibody is desired. In the examples, a monoclonal antibody for mouse LNGFR was identified using a dissociated primary culture of Schwann cells. In conjunction with the assay disclosed in the examples, mouse fibroblasts acted as a negative control. However, primary cultures of other cell lines can be used to detect monoclonal antibodies to LNGFR. For example, forebrain cholinergic neurons or sensory neurons can be used. In addition, a primary culture of epithelial cells can be used as a negative control.

Other markers found on neural cells include Platelet Derived Growth Factor Receptor (PDGFR), Fibroblast Growth Factor (FGF) and Stem Cell Factor Receptor (SCFR). Cells useful for detecting monoclonal antibodies to PDGFR and FGF include primary cultures of glial cells or fibroblasts. Negative controls include cultures of epithileal cells and neuroblastomas. SCFR is expressed on a subset of neuronal cells. Primary cultures of melanocytes or melanoma cells can be used to detect monoclonal antibodies to this receptor. Negative controls include primary cultures of fibroblasts and glial cells.

It is not always necessary to generate polyclonal or monoclonal antibodies that are species specific. Monoclonal antibodies against an antigenic determinant from one species may react against that antigen from more than one species. For example, as stated above, the antibody directed against the human LNGFR molecule also recognizes LNGFR on monkey cells. When cross-reactive antibodies are available, there is no need to generate antibodies which are species specific using the methods described above.

Nestin, a second marker in the neural crest stem cell, is an intermediate filament protein primarily located intracellularly, which has been shown to be present in CNS neuroepithelial cells and Schwann cells in the peripheral nervous system of rats (Friedman et al. (1990) *J. Comp. Neurol.* 295:43–51). Monoclonal antibodies specific for rat nestin have been isolated: Rat 401, (Hockfield, S. et al. (1985) *J. Neurosci.* 5(12):3310–3328). A polyclonal rabbit anti-nestin antisera has been reported which recognizes mouse nestin (Reynolds, D. A. et al. (1992) *Science* 255:1707–1710). The DNA sequences encoding the rat nestin gene have been cloned (Lendahl, U. et al. (1990) *Cell* 60:585–595). These DNA sequences are used to isolate nestin clones from other mammalian species. These DNA sequences are then used to express the nestin protein and monoclonal antibodies directed against various mammalian nestins are generated as described above for LNGFR.

As used herein, the term "glial progenitor cell" refers to a cell which is intermediate between the fully differentiated glial cell and a precursor multipotent neural stem cell from which the fully differentiated glial cell develops. In general, such glial progenitor cells are derived according to the methods described herein for isolating such cells from various tissues including adult and embryonic CNS and PNS tissue as well as other tissues which may potentially contain such progenitors.

As used herein, the term "PNS glial progenitor cell" means a cell which has differentiated from a mammalian neural crest stem cell which is committed to the PNS glial lineage and is a dividing cell but does not yet express surface or intracellular markers found on more differentiated, non-dividing PNS glial cells. Such progenitor cells are preferably obtained from neural crest stem cells isolated from the embryonic neural crest which have undergone further differentiation. However, equivalent cells may be derived from other tissue. When PNS glial progenitor cells are placed in appropriate culture conditions they differentiate into PNS glia expressing the appropriate differentiation markers, for example, sulfatide and GFAP.

Sulfatide is a glycolipid molecule found on the surface of Schwann cells and oligodendricytes in rats, mice, chickens and humans. The expression of sulfatide on Schwann cells is dependent upon either axonal contact or exposure to cyclic AMP or analogs thereof, such as forskolin (Mirsky, R. et al. (1990) *Development* 109:105–116). Monoclonal antibodies specific for sulfatide have been reported (Sommer, I. et al. (1981) *Dev. Biol.* 83:311–327).

Glial fibrillary acidic protein (GFAP) is an intermediate filament protein specifically expressed by astrocytes and glial cells of the CNS and by Schwann cells, the glial cells of the PNS (Jessen, K. R. et al. (1984) *J. Neurocytology* 13:923–934 and Fields, K. L. et al. (1989) *J. Neuroimmuno.* 8:311–330). Monoclonal antibodies specific for GFAP have been reported (Debus et al. (1983) *Differentiation* 25:193–203). Mouse and human GFAP genes have been cloned (Cowan, N. J. et al. (1985) *N.Y. Acad. Sci.* 455:575–582 and Bongcamrudlowss, D. et al. (1991) *Cancer Res.* 51:1553–1560, respectively). These DNA sequences are used to isolate GFAP clones from other mammalian species. These DNA sequences are then used to express the GFAP protein and monoclonal antibodies directed against various mammalian GFAPs are generated as described above for LNGFR.

As used herein, the term "factors permissive for PNS glial cell differentiation" means compounds, such as, but not limited to, protein or steroid molecules or substrates such as FN or PDL, which permit at least neural crest stem cells to become restricted to the PNS glial lineage. Such lineage-restricted progeny of neural crest stem cells include glial progenitor cells, which are at least bipotential, in that they can divide to give rise to self, as well as, more mature non-dividing PNS glial cells.

As used herein, the term "neuronal progenitor cell" refers to a cell which is intermediate between the fully differentiated neuronal cell and a precursor multipotent neural stem cell from which the fully differentiated neuronal cell develops. In general, such neuronal progenitor cells are derived according to the methods described herein for isolating such cells from various tissues including adult and embryonic CNS and PNS tissue as well as other tissues which may potentially contain such progenitors.

As used herein, the term "PNS neuronal progenitor cell" means a cell which has differentiated from a mammalian neural crest stem cell which is committed to one or more PNS neuronal lineages and is a dividing cell but does not yet express surface or intracellular markers found on more differentiated, non-dividing PNS neuronal cells. Such progenitor cells are preferably obtained from neural crest stem cells isolated from the embryonic neural crest which have undergone further differentiation. However, equivalent cells may be derived from other tissue. When PNS neuronal progenitor cells are placed in appropriate culture conditions they differentiate into mature PNS neurons expressing the appropriate differentiation markers, for example, peripherin, neurofilament and high-polysialic acid neural cell adhesion molecule (high PSA-NCAM).

Peripherin, a 57 kDa intermediate filament protein, is expressed in adult rodents primarily in peripheral neurons. More limited expression of peripherin is found in some motoneurons of the spinal cord and brain stem and a limited group of CNS neurons. Peripherin is expressed in rat embryos primarily in neurons of peripheral ganglia and in a subset of ventral and lateral motoneurons in the spinal cord (Gorham, J. D. et al. (1990) *Dev. Brain Res.* 57:235–248). Antibodies specific for this marker have been identified in the rat (Portier, M. et al. (1983/84) *Dev. Neurosci.* 6:335–344). The DNA sequences encoding the rat peripherin gene have been cloned (Thompson, M. A. et al. (1989) *Neuron* 2:1043–1053). These DNA sequences are used to isolate DNA sequences for the peripherin gene in other mammals that are used to express the protein and generate antibodies directed against other mammalian peripherin proteins, as described above for LNGFR.

Neurofilaments are neuron-specific intermediate filament proteins. Three neurofilament (NF) proteins have been reported: NF68, a 68 kD protein also called NF-L (Light); NF160, a 160 kD protein also called NF-M (Medium); NF200, a 200 kD protein also called NF-H (Heavy). In general, there is coordinate expression of all three NF proteins in neurons. The DNA sequences encoding the rat NF200 and NF160 proteins have been cloned (Dautigny, A. et al. (1988) *Biochem. Biophys. Res. Commun.* 154:1099–1106 and Napolitano, E. W. et al. (1987) *J. Neurosci.* 7:2590–2599, respectively). All three NF protein genes have been cloned in mice and humans. Mouse NF68 nucleic acid sequences were reported in Lewis, S. A. et al. (1985) *J. Cell Biol.* 100:843–850. Mouse NF160 nucleic acid sequences were reported in Levy, E. et al. (1987) *Eur. J. Biochem.* 166:71–77. Mouse NF200 nucleic acid sequences were reported in Shneidman, P. S. et al. (1988) *Mol. Brain Res.* 4:217–231. In humans, nucleic acid sequences were reported for: NF68, Julien, J.-P. et al. (1987) *Biochem. Biophys. Acta.* 909:10–20; NF160, Myers, M. W. et al. (1987) *EMBO J.* 6:1617–1626; NF200, Lee, J. F. et al. (1988) *EMBO J.* 7:1947–1955. These DNA sequences are used to produce the protein for the production of antibodies or to isolate other mammalian NF genes and the proteins expressed and antibodies generated for any desired species, as described above for LNGFR. As used herein, the term "NF+" means expression of one or more of the three NF proteins.

As used herein, the term "factors permissive for PNS neuronal cell differentiation" means compounds, such as, but not limited to, protein or steroid molecules or substrates such as FN or PDL, which permit at least a neural crest stem cell to become restricted to the PNS neuronal lineage. Such lineage-restricted progeny of neural crest stem cells include PNS neuronal progenitor cells, which are at least bipotential, in that they can divide to give rise to self, as well as, more mature, non-dividing PNS neurons.

As indicated in the examples, when neural stem cells are contacted with certain factors permissive for neuronal and glial cell differentiation, such cells differentiated into neurons, glia and a subpopulation referred to as "O" cells. As disclosed in Example 10, these O cells are, in fact, smooth muscle cells. Thus, at least some of the factors which are permissive for differentiation to neuronal and/or glial cells are also permissive for the differentiation of neural stem cells to smooth muscle cells. However, as also indicated in Example 10, there are factors which are instructive for smooth muscle cell differentiation. In this regard, the term "instructive factor" or grammatical equivalents refers to one or more factors which are capable of causing the differentiation of neural stem cells primarily to a single lineage, e.g., glial, neuronal or smooth muscle cell. Thus, a factor which is instructive for smooth muscle cell differentiation is one which causes differentiation of neural stem cells to smooth muscle cells at the expense of the differentiation of such stem cells into other lineages such as glial or neuronal cells. As indicated in Example 10, mammalian serum contains one or more factors which are instructive factors for the production of smooth muscle cells.

Generally, a differentiated cell, for example a neuron or glial cell, exhibits most or all of the phenotypic properties of a neuron or glial cell, including cell-specific markers, functional characteristics, and structural characteristics. For example, neurons generally contain peripherin and neurofilament protein, and exhibit physical neurites, while glial cells are identified with sulfatide, glial fibrillary acidic protein (GFAP), S100 and myelin protein $P_o$, among other things.

Having identified that mammalian serum contains one or more instructive factors for smooth muscle cell differentiation, such instructive factors can be identified by fractionating mammalian serum and adding back one or more such fractions to a neural stem cell culture to identify one or more fractions containing instructive factors for smooth muscle cell differentiation. Positive fractions can then be further fractionated and reassayed until the one or more components required for instructive differentiation to smooth muscle cells are identified.

Mammalian neural crest stem cell compositions are provided which serve as a source for neural crest cell derivatives such as neuronal and glial progenitors of the PNS which in turn are a source of PNS neurons and glia. Methods are provided for the isolation and clonal culture of neural crest stem cells, in the absence of feeder cells. In the examples provided, these methods utilize a chemically defined medium which is supplemented with chick embryo extract as a source of mitogens and survival factors. Factors present in the extract of chicken embryos allow the growth and self renewal of rat and mouse neural crest stem cells. However, media used to isolate and propagate rat and mouse neural crest stem cells can be used to isolate and propagate neural crest stem cells from other mammalian species, such as human and non-human primates, equines, felines, canines, bovines, porcines, lagomorphs, etc.

Culture conditions provided herein allow the isolation self-renewal and differentiation of mammalian neural crest stem cells and their progeny. These culture conditions may be used on either immortalized or non-immortalized stem cells and progenitor cells. These culture conditions may be modified to provide a means of detecting and evaluating growth factors relevant to mammalian neural crest stem cell self-renewal and the differentiation of the stem cell and its progeny. These modifications include, but are not limited to, changes in the composition of the culture medium and/or the substrate and in the specific markers used to identify either the neural crest stem cell or their differentiated derivatives.

Culture conditions are provided which allow the differentiation of mammalian neural crest stem cells into the PNS neuronal and glial lineages in the absence of feeder cell layers. These culture conditions may be used on either immortalized or non-immortalized stem cells and progenitor cells. In addition to liquid culture media, these culture conditions utilize a substratum comprising fibronectin alone or in combination with poly-D-lysine. In the examples provided, human fibronectin is utilized for the culturing of rat and mouse neural crest stem cells and their progeny. Human fibronectin can be used for the culturing of neural crest stem cells isolated from avian species as well as from any mammal, as the function of the fibronectin protein is highly conserved among different species. Cells of many species have fibronectin receptors which recognize and bind to human fibronectin.

In order to isolate the subject neural crest stem cells, it is necessary to separate the stem cell from other cells in the embryo. Initially, neural crest cells are obtained from mammalian embryos.

For isolation of neural crest cells from mammalian embryos, the region containing the caudal-most 10 somites are dissected from early embryos (equivalent to gestational day 10.5 day in the rat or 8.5 days in the mouse). These trunk sections are transferred in a balanced salt solution to chilled depression slides, typically at 4° C., and treated with collagenase in an appropriate buffer solution such as Howard's Ringer's solution. After the neural tubes are free of somites and notochords, they are plated onto fibronectin (FN)-coated culture dishes to allow the neural crest cells to migrate from the neural tube. Twenty-four hours later, following removal of the tubes with a sharpened tungsten needle, the crest cells are removed from the FN-coated plate by treatment with a Trypsin solution, typically at 0.05%. The suspension of detached cells is then collected by centrifugation and plated at an appropriate density, generally 225 cells/100 mm dish in an appropriate chemically defined medium. This medium is preferentially free of serum and contains components which permit the growth and self-renewal of neural crest stem cells. The culture dishes are coated with an appropriate substratum, typically a combination of FN and poly-D-lysine (PDL).

Procedures for the identification of neural crest stem cells include incubating cultures of crest cells for a short period of time, generally 20 minutes, at room temperature, generally about 25° C., with saturating levels of antibodies specific for a particular marker, e.g., LNGFR. Excess antibody is removed by rinsing the plate with an appropriate medium, typically L15 medium (Gibco) supplemented with fresh vitamin mix and bovine serum albumin (L-15 Air). The cultures are then incubated at room temperature with a fluorochrome labelled secondary antibody, typically Phycoerythrin R-conjugated secondary antibody (TAGO) at an appropriate dilution for about 20 minutes. Excess secondary antibodies are then removed using an appropriate medium, such as L-15 Air. The plates are then covered with the chemically defined growth medium and examined with a fluorescence microscope. Individual LNGFR$^+$ clones are isolated by fluorescence activated cell sorting (FACS) or, more typically, by marking the plate under the identified clone. The markings are typically made to a diameter of 3–4 mm, which generally allows for the unambiguous identification of the progeny of the founder cell at any time during an experiment. If desired, individual LNGFR$^+$ clones are removed from the original plate by trypsinization with the use of cloning cylinders.

Procedures for permitting the differentiation of stem cells include the culturing of isolated stem cells in a medium permissive for differentiation to a desired lineage, such as Schwann cell differentiation (SCD) medium. Other procedures include growth of isolated stem cells on substrates capable of permitting differentiation, such as FN or FN and PDL.

Procedures for the serial subcloning of stem cells and their derivatives include the trypsinization of individual clones, as described above, followed by replating the clone on a desired substrate and culturing in a desired medium, such as a chemically defined medium suitable for maintenance of stem cells or SCD medium permissive for the differentiation of said neural crest stem cells. Crest cells may be identified following serial subcloning by live-cell labeling with an antibody directed against LNGFR, as described above.

The methods described herein provide the basis of functional assays which allow for the identification and production of cellular compositions of mammalian cells which have properties characteristic of neural crest stem cells, glial or neuronal progenitor cells or multipotent stem cell precursor of such progenitor cells. In order to isolate such cells from tissues other than embryonic neural tubes, it is necessary to separate the progenitor and/or multipotent stem cells from other cells in the tissue. The methods presented in the examples for the isolation of neural crest stem cells from neural tubes can be readily adapted for other tissues by one skilled in the art. First, a single cell suspension is made from the tissue; the method used to make this suspension will vary depending on the tissue utilized. For example, some tissues require mechanical disruption of the tissue while other tissues require digestion with proteolytic enzymes alone or in combination with mechanical disruption in order to create the single cell suspension. Tissues such as blood already exists as a single cell suspension and no further treatment is required to generate a suspension, although hypotonic lysis of red blood cells may be desirable. Once the single cell suspension is generated it may be enriched for cells expressing LNGFR or other neural cell-specific markers on their surface. One protocol for the enrichment for LNGFR$^+$ cells is by incubating the cell suspension with antibodies specific for LNGFR and isolating the LNGFR$^+$ cells. Enrichment for cells expressing a neural cell-specific surface marker is particularly desirable when these cells represent a small percentage (less than 5%) of the starting population. The isolation of cells which have complexed with an antibody for a neural cell-specific surface marker such as is carried out using any physical method for isolating antibody-labeled cells. Such methods include fluorescent-activated cell sorting in which case the cells, in general, are further labeled with a fluorescent secondary antibody that binds the anti-LNGFR antibody, e.g., mouse anti-LNGFR and fluorescein label goat anti-mouse IgG; panning in which case the antibody-labeled cells are incubated on a tissue-culture plate coated with a secondary antibody; Avidin-sepharose chromatography in which the anti-LNGFR antibody is biotinylated prior to incubation with the cell suspension so that the complexed cells can be recovered on an affinity matrix containing avidin (i.e., where the antibody is an antibody conjugate with one of the members of a binding pair); or by use of magnetic beads coated with an appropriate anti-antibody so that the labeled LNGFR-expressing cells can be separated from the unlabeled cells with the use of a magnet. All of the foregoing cell isolation procedures are standard published procedures that have been used previously with other antibodies and other cells.

The use of antibodies specific for neural stem cell-specific surface markers results in the isolation of multipotent neural stem cells from tissues other than embryonic neural tubes. For example, as previously indicated, LNGFR is expressed in cells of the ventricular zone throughout the embryonic central nervous system of the rat and chick. This implies that other mammalian species have a similar pattern of LNGFR expression and studies in human with monoclonal antibodies against the human LNGFR (Loy, et al. (1990) *J. Neurosci. Res.* 27:651–654) are consistent with this expectation. Since cells from the ventricular zone (Cattaneo et al. (1991) *Trends Neurosci.* 14:338–340; Reynolds et al. (1992) *Science* 255:1707–1710) are likely to be stem cells (Hall et al. (1989) Development 106:619–633; Potter et al. (1990) *Development* 110:1001–1020) antibodies to neural cell-specific surface markers should prove useful in isolating multipotent neural stem cells from the central and peripheral nervous systems and from other tissue sources.

Alternatively, or in conjunction with the above immuno-isolation step, the cells are plated at clonal density, generally 225 cells/100 mm dish, in an appropriate chemically defined medium on a suitable substrate as described in the examples for isolation of rat or mouse neural crest stem cells. The presence of neural crest-like stem cells (e.g., a multipotent neural stem cell) is confirmed by demonstrating that a single cell can both self-renew and differentiate to members of at least the PNS neuronal and glial lineages utilizing the culture conditions described herein. Other types of multipotent neural stem cells are identified by differentiation to other cell type such as CNS neural or glial cells or their progenitors. Depending upon the source of the tissue used in the foregoing methods, multipotent neural stem cells may not be obtained. Rather, further differentiated cell types such as glial and neuronal progenitor cells may be obtained.

Transplantation assay systems described herein provide the basis of functional assays which allow for the identification of mammalian cells which have properties characteristic of neural crest stem cells, multipotent neural stem cells and/or neuronal or glial progenitor cells. Cells of interest, identified by either the in vivo or in vitro assays described above, are transplanted into mammalian hosts using standard surgical procedures. The transplanted cells and their progeny are distinguished from the host cells by the presence of species specific antigens or by the expression of an introduced marker gene. The transplanted cells and their progeny are also stained for markers of mature neurons and glia in order to examine the developmental potential of the transplanted cells. This transplantation assay provides a means to identify neural crest stem cells by their functional properties in addition to the in vitro culture assays described above.

Additionally, the transplantation of cells having characteristics of multipotent neural stem cells, neural crest stem cells or progenitors of neuronal or glial cells provides a means to investigate the therapeutic potential of these cells for neurological disorders of the PNS and CNS in animal models. Examples of PNS disorders in mice include the trembler and shiverer strains. The trembler mutation is thought to involve a defect in the structural gene for myelin basic protein (MBP). This mutation maps to the same region of chromosome 11 as does the MBP gene. This mutation results in the defective myelination of axons in the PNS. An analogous disorder is seen in humans, Charcot-Marie-Tooth syndrome, which results in progressive neuropathic muscular atrophy.

The shiverer mutation in mice results in a severe myelin deficiency throughout the CNS and a moderate hypomyelination in the PNS. Severe shivering episodes are seen 12 days after birth. An analogous disorder is seen in humans, Guillaum-Barre' disease, which is characterized by an acute febrile polyneuritis.

Cells having characteristics of multipotent neural stem cells, neural crest stem cells or neuronal or glial progenitors of the PNS or CNS (identified by either in vitro or in vivo assays) are introduced into a mammal exhibiting a neurological disorder to examine the therapeutic potential of these cells. These cells are preferably isolated from a mammal having similar MHC genotypes or the host mammal is immunosuppressed using drugs such as cyclosporin A. The cells are injected into an area containing various peripheral nerves known to be effected in a particular mammal or into the spinal cord or brain for mammals which show involvement of the CNS. The cells are injected at a range of concentrations to determine the optimal concentration into the desired site. Alternatively, the cells are introduced in a plasma clot or collagen gel to prevent rapid dispersal of cells from the site of injection. The effect of this treatment on the neurological status of the model animal is noted. Desired therapeutic effects in the above mutant mice include the reduction or cessation of seizures or improved movement of lower motor extremities.

In an alternative embodiment, the cells are transplanted to alleviate or treat a neurological disorder of the host animal. For example, demyelination disorders such as multiple sclerosis or Guillamme Barré Syndrome may be treated with these cells.

There is strong interest in identifying the multipotent neural stem cells such as the neural crest stem cell and defining culture conditions which allow the clonal propagation and differentiation of said stem cells. Having possession of a multipotent neural stem cell or a neural crest stem cell allows for identification of growth factors associated with self regeneration. In addition, there may be as yet undiscovered growth factors associated with (1) with the early steps of restriction of the stem cell to a particular lineage; (2) the prevention of such restriction; and (3) the negative control of the proliferation of the stem cell or its derivatives.

The multipotent neural stem cell, neural crest stem cell, progeny thereof or immortalized cell lines derived therefrom are useful to: (1) detect and evaluate growth factors relevant to stem cell regeneration; (2) detect and isolate ligands, such as growth factors or drugs, which bind to receptors expressed on the surface of such cells or their differentiated progeny (e.g., Glial Growth Factor (GGF), Heregulin and Neu Differentiation Factor (NDF)); (3) provide a source of cells which express or secrete growth factors specific to multipotent neural stem cells; (4) detect and evaluate other growth factors relevant to differentiation of stem cell derivatives, such as neurons and glia; (5) produce various neural stem cell derivatives, including both the progenitors and mature cells of a given lineage and (6) provide a source of cells useful for treating neurological diseases of the PNS and CNS in model animal systems and in humans. The culture conditions used herein allow for the growth and differentiation of stem cells in vitro and provide a functional assay whereby mammalian tissues can be assayed for the presence of cells having the characteristics of neural stem cells. The transplantation assay described herein also provides a functional assay whereby mammalian neural stem cells may be identified.

As indicated in the examples, neural crest stem cells have been passaged for at least six-ten generations in culture. Although it may be unnecessary to immortalize those or other multipotent neural stem cell lines or progenitor cell lines obtained by the methods described herein, once a cell line has been obtained it may be immortalized to yield a continuously growing cell line useful for screening trophic or differentiation factors or for developing experimental transplantation therapies in animals. Such immortalization can be obtained in multipotent neural stem cells or progenitors of glial and neuronal cells by genetic modification of such cells to introduce an immortalizing gene. Thus, an immortalized multipotent neural stem cell retains its ability to grow in an undifferentiated state under defined conditions, but can be induced to differentiate by altering the growth conditions. It should be understood that an immortalized stem cell does not spontaneously differentiate, but is induced to differentiate by modifying the growth conditions.

By "immortalizing gene" herein is meant a gene which confers the ability to grow indefinitely in culture and which does not significantly alter the multipotency of the stem cells, or the progenicity of glial or neuronal cells.

Examples of immortalizing genes include: (1) nuclear oncogenes such as v-myc, N-myc, T antigen and Ewing's sarcoma oncogene (Fredericksen et al. (1988) *Neuron* 1:439–448; Bartlett, P. et al. (1988) *Proc. Natl. Acad. Sci. USA* 85:3255–3259, and Snyder, E. Y. et al. (1992) *Cell* 68:33–51), (2) cytoplasmic oncogenes such as bcr-abl and neurofibromin (Solomon, E. et al. (1991) *Science* 254:1153–1160), (3) membrane oncogenes such as neu and ret (Aaronson, A. S. A (1991) *Science* 254:1153–1161), (4) tumor suppressor genes such as mutant p53 and mutant Rb (retinoblastoma) (Weinberg, R. A. (1991) *Science* 254:1138–1146), and (5) other immortalizing genes such as Notch dominant negative (Coffman, C. R. et al. (1993) *Cell* 23:659–671). Particularly preferred oncogenes include v-myc and the SV40 T antigen.

Immortalized cells such as immortalized multipotent neural stem cells and neural crest stem cells are particularly useful. Generally, neural crest stem cells are obtained in small numbers from very early embryos. Since transplantation experiments generally require large number of cells, the availability of an immortalized cell line provides virtually unlimited quantities of stem cells. In addition, the fact that the immortalized cells may be further transformed with other genes allows the use of the immortalized stem cells as models for gene therapy.

Thus, methods for introducing or transplanting immortalized stem cells into a host animal or mammal are provided. Transplantation techniques are well known in the art, and may be done with immortalized cells. The immortalized cells may be immortalized glial or neuronal progenitor cells, or immortalized multipotent neural stem cells, or immortalized mammalian neural crest stem cells. Thus, for example, the immortalized cells may be transplanted into a host to evaluate the therapeutic potential of the cells, or to treat a neurological disorder of the nervous system, as outlined above. In a preferred embodiment, the neurological disorder is a disorder of the peripheral nervous system.

In addition, the immortalized cell line may be used to screen drugs which may effect the development, differentiation and/or function of neural crest-derived neurons and glia. These include both small molecule organic pharmaceuticals as well as growth factors.

The availability of large amounts of cells of an otherwise minor population allows the generation of cDNA libraries which can permit the isolation of rare molecules expressed in the stem cells, such as growth factor receptors. Such receptors may be used to isolate novel growth factors. Alternatively, the cells may directly express novel growth factors. Thus, conditioned media may be screened in various assays to look for novel activities.

In addition, cell lines from animal models of human genetic disorders affecting neural crest cells or derivatives may be made. These cell lines could be valuable for testing various approaches to gene therapy.

In one embodiment, the cells are permanently immortalized. In the preferred embodiment, the cells are conditionally immortalized. Conditional immortalization refers to the immortalization of a cell in such a manner that the cell may be subsequently disimmortalized, as described below. For example, a multipotent stem cell may be immortalized for cloning and maintenance, and then disimmortalized prior to transplanting into an animal, thus removing the immortalizing gene. Disimmortalization may occur prior to differentiation, or after differentiation. Disimmortalized cells are particularly useful in transplant applications, since the immortalizing oncogenes are removed prior to introduction into the body, thus eliminating the potential creation of tumors as a result of the immortalizing gene.

By "disimmortalization" herein is meant a process whereby all or part of the immortalization gene of an immortalized cell is physically excised from the genome of the cell, allowing the cell to return to a more normal senescence cycle, such that it no longer grows and proliferates indefinitely in culture. A disimmortalized cell may have all or part of the conditional immortalization construct removed. Thus, as will be appreciated by those in the art, in conjunction with the disclosure herein, a variety of conditional immortalization constructs may be made, resulting in different amounts of exogenous nucleic acid left in the cell genome. In a preferred embodiment, all of the immortalization gene is removed from a disimmortalized cell.

The methods of conditional immortalization and disimmortalization of the invention are accomplished using a site-specific recombinase system. Several such systems are known, including the Cre recombinase from the bacteriophage P1, and the FLP ("flip") recombinase from *Saccharoinyces cerevisiae*. The Cre system utilizes the Cre recombinase, which is a 38 kDa protein, and two 34 basepair recombinase target sites (RTS), termed loxP. Recombination can occur between directly repeated loxP sites on the same molecule to excise the intervening DNA segment. See Sauer et al., Proc. Natl. Acad. Sci. USA 85:5166 (1988); Sauer et al., Nuc. Acids Res. 17:147 (1989); Lakso et al., Proc. Natl. Acad.

Sci. USA 89:6232; Hoess et al., J. Mol. Biol. 181:351–362 (1985); Abremski et al., Cell 32:1301 (1983); Sternberg et al., J. Mol. Biol. 150:467–486 (1981); and Orban et al., Proc. Natl. Acad. Sci. USA 89:6861 (1992). The FLP system utilizes the FLP protein and two FLP recombination target sites (termed FRT in the art; depicted herein as RTSs) that consist of two 13 inverted basepair repeats and an 8 basepair spacer (See for example O'Gorman, Science 251:1351 (1991); Jayaram, PNAS USA 82:5875–5879 (1985); Senecof et al., PNAS USA 82:7270 (1985); and Gronostajski et al., J. Biol. Chem. 260:12320 (1985)). All of these references are expressly incorporated by reference.

By "recombinase target site" (RTS) herein is meant a nucleic acid sequence which is recognized by a recombinase for the excision of the intervening sequence. It is to be understood that two RTSs are required for excision. Thus, when the cre recombinase is used, each RTS comprises a loxP site; when loxP sites are used, the corresponding recombinase is the cre recombinase. That is, the recombinase must correspond to or recognize the RTSs. When the FLP recombinase is used, each RTS comprises a FLP recombination target site (FRT); when FRT sites are used, the corresponding recombinase is the FLP recombinase.

Using these recombinase systems, the immortalization genes inserted into a host cell may be excised upon exposure to the appropriate recombinase. Thus, the conditional immortalization constructs are inserted into a cell in an orientation that results in the expression of the immortalization gene. For all of the embodiments, the host cells must not contain nucleic acid encoding the appropriate recombinase prior to the addition of the exogeneous nucleic acid of the invention. At some later time, the recombinase is expressed and contacts the recombinase target sites to excise the intervening immortalization gene.

Preferably, selection marker genes are used to detect or select for successful immortalization and disimmortalization. For example, the expression of a first selection marker allows the detection of successful immortalization; that is, the marker gene is expressed when the immortalization gene has been integrated into the cell genome. The expression of a second selection marker, preferably different from the first selection marker gene, indicates the excision of the immortalization gene, as is more fully described below. These selection markers can be either positive or negative selection markers. As is known in the art, "selection marker gene" or equivalents means genes that allow the selection of cells containing the gene. "Positive selection" refers to a process whereby only cells that contain the positive selection marker will survive upon exposure to the positive selection agent or be marked. For example, drug resistance is a common positive selection marker; cells containing the drug resistance gene will grow on medium containing the drug, and those cells which do not contain the resistance gene will die. Suitable drug resistance genes are histidinol dehydrogenase, neomycin-resistance, hygromycine-resistance, and puromycin-resistance, among others. Other positive selection marker genes include genes that allow the sorting or screening of cells. These genes include the alkaline phosphatase gene, the gene for green fluorescent protein, the lacZ gene, and surface markers such as CD8, among others. In one embodiment, as is described below, the immortalization gene may serve as a positive selection marker.

Of particular use in this invention are negative selection markers, the use of which is outlined below. "Negative selection" refers to a process whereby cells transfected with a negative selection marker are killed upon exposure to an appropriate negative selection agent which kills cells containing the negative selection marker. For example, cells which contain the herpes simplex virus-thymidine kinase (HSV-tk) gene are sensitive to gancyclovir ($GANC^S$). Similarly, the Gpt gene renders cells sensitive to 6-thioxanthine. When appropriately positioned in a conditional immortalization construct, the negative selection marker gene can be used to isolate cells which have been disimmortalized. That is, the negative selection marker is expressed with the immortalization gene, such that if the immortalization gene is still present, the cells will be killed.

Generally, the conditional immortalization-disimmortalization vectors and technique proceeds as follows. The gene constructions used for immortalization are set up in such a way that a first transformation with exogeneous nucleic acid results in immortalization. The cells may be grown and propagated and other genes may be added, as outlined above. In some instances, when the cells are stem cells, the immortalized cells may be differentiated if desired. Then prior to transplantation or at some later time, the cells are manipulated such that the immortalization gene is excised; i.e. the cells are disimmortalized.

In a preferred embodiment, the cloning vector which introduces the immortalization gene into the cells is constructed such that the immortalization gene, any selection markers, promoters and RTSs are integrated into the genome simultaneously. That is, further integration of DNA into the genome is not needed to facilitate disimmortalization. Alternatively, the immortalization gene may be introduced into the genome with sufficient flanking sequences to allow the construction of homologous recombination vectors to introduce the additional required sequences.

In a preferred embodiment, disimmortalization occurs as a result of a further transformation with exogeneous nucleic acid encoding the recombinase, as is outlined below.

In one embodiment, the invention provides conditionally immortalized cell lines. These immortalized cell lines contain nucleic acid which comprises a variety of different conditional immortalization constructs as outlined below. These immortalized cell lines may be made by transforming at least one cell with nucleic acid comprising the contructs of the invention.

These conditionally immortalized cell lines may be used in a variety of methods for disimmortalization, as outlined below.

In another embodiment, the cell lines contain nucleic acid comprising recombinase target sites that flank an immortalization gene in the genome of the cells of the cell lines. These target sites must be in an orientation such that the RTSs are capable of mediating excision of the immortalization gene when the RTSs are contacted with a recombinase. That is, in the absence of the recombinase which recognizes the RTSs, the immortalization gene is incorporated into the genome of the cell and expressed, to create an immortalized cell line. When the RTSs are exposed to the corresponding recombinase, excision of the sequence between the RTSs occurs. Since this sequence contains the immortalization gene, the excision event results in a loss of the gene, i.e. disimmortalization.

In a further embodiment, the invention provides immortalized cell lines that contain nucleic acid comprising a first recombinase target site, an immortalization gene, a negative selection marker gene, and a second recombinase target site, as is generally depicted in FIG. 3A. As above, in the absence of the recombinase which recognizes the RTSs, the immortalization gene is incorporated into the genome of the cell and expressed, to create an immortalized cell line. The RTSs are capable of mediating excision of the immortalization gene when the RTSs are contacted with a recombinase. In a preferred embodiment, the immortalization and negative selection marker genes are flanked by the RTSs. Thus, upon transformation, the immortalization gene and negative selection marker are expressed, and transformed cells may be selected on the basis of immortalization or expression of the negative selection marker. Upon exposure to or contact with a recombinase that recognizes the RTSs, the immortalization gene and negative selection marker are excised, and disimmortalized cells may be selected by exposure to the negative selection agent. That is, disimmortalized cells will survive, and those that still contain the immortalization gene and the negative selection marker gene will die.

In an additional embodiment, the inventin provides immortalized cell lines that contain nucleic acid comprising a first recombinase target site, an immortalization gene, a selection marker gene, and a second recombinase target site. As above, in the absence of the recombinase which recognizes the RTSs, the immortalization gene is incorporated into the genome of the cell and expressed, to create an immortalized cell line. The RTSs are capable of mediating excision of the immortalization gene when the RTSs are contacted with a recombinase. In one embodiment, the orientation of the construct is preferably such that in the absence of a recombinase, the immortalization gene is expressed but the selection marker gene is not. This is preferably done through the addition of a STOP site to the construct, such as is shown in FIGS. 1 and 4, although as depicted in FIG. 5, it may also be accomplished by having one of the RTSs in the middle of the selection marker gene. Upon exposure to a recombinase which recognizes the RTSs, the intervening sequence is excised, resulting in a loss of the immortalization gene and the expression of the selection marker gene, thus allowing for selection of disimmortalized cells. Alternatively, the orientation of the construct is such that upon transformation, the immortalization gene and the selection gene are expressed, thus allowing selection for immortalization. Upon exposure to a recombinase that recognizes the RTSs, the immortalization gene and selection gene are excised, and the resulting cells may be selected for disimmortalization by a loss of the selection gene.

In a further embodiment, the invention provides immortalized cell lines containing nucleic acid comprising a first recombinase target site, an immortalization gene, a first selection marker gene, a second recombinase target site, and a second selection marker gene. In this embodiment, the orientation of the construct is such that upon transformation, the immortalization gene and the first selection marker gene are expressed, and the second selection marker gene is not. This is preferably accomplished by the addition of a STOP site to the construct, although as above it may be done in alternative ways. Upon exposure or contact with a recombinase that recognizes the RTSs, the immortalization gene and the first selection marker gene are excised, and the second selection marker is expressed. This allows for selection of disimmortalized cells on the basis of the second selection marker gene.

Several specific embodiments are shown in the Figures, which utilize a preferred retroviral cloning vector with either the Cre/loxP or the FLP/FRT recombinase systems. Those skilled in the art will recognize that a variety of constructions will result in the creation of immortalized cells which can be subsequently disimmortalized, only several of which are shown in the Figures.

In a preferred embodiment, the conditional immortalization constructs are as depicted in FIGS. 1 and 2. First, a cloning vector is constructed which contains: a first selectable marker with a first promoter; a second promoter; a multiple polylinker cloning site (MPCS), flanked by the recombinase target sites (RTS); and a second selectable marker. The immortalizing gene, generally an oncogene, is inserted in the MPCS, along with a STOP sequence that prevents the expression of the second selectable marker. STOP sequences such as TGACTGACCTGA are known in the art. Thus, in the absence of a recombinase, the immortalizing gene is expressed using the second promoter and the first selectable marker is expressed using the first promoter. This allows the selection of transformed, immortalized cells, but the STOP sequence prevents the expression of the second marker. Thus the immortalized cells may be cloned and grown, and additional genes added if desired. For disimmortalization, expression (preferably transient) of the appropriate recombinase, using techniques well known in the art, is accomplished. This results in the excision of the recombinase target sites, the MPCS containing the immortalization gene, and the STOP sequence. Thus, the second selectable marker gene is now expressed, and disimmortalized cells may be selected on the basis of this marker gene.

In FIG. 1A, the first selectable marker is translated via the first promoter (or alternatively, from a promoter internal to the LTR), and the immortalization gene inserted in the MPCS is driven by the second promoter. In the absence of a recombinase, the STOP sequence prevents the translation of the second selectable marker. Upon exposure to the recombinase, the immortalization gene and the STOP sequence are excised, allowing the second selectable marker to run off the second promoter. In FIG. 1B, translation of the immortalization gene is driven by the internal LTR promoter, the first selectable marker is translated via the SV40 promoter or equivalents, but the STOP sequence prevents the translation of the second selectable marker. Upon exposure to the recombinase, the immortalization gene and the STOP sequence are excised, allowing the translation of the second selectable marker. In FIG. 1C, the first selectable marker and the immortalization gene are translated via either a first promoter or the LTR promoter, but the STOP sequence prevents the translation of the second selectable marker. Upon exposure to the recombinase, the immortalization gene and the STOP sequence are excised, allowing the translation of the second selectable marker via the promoter or the LTR. In FIG. 1D, translation of the green fluorescence protein and the immortalization gene occur via the LTR promoter (or another promoter). The green fluorescent protein serves as a selection marker. Upon exposure to the recombinase, the immortalization gene and the green fluorescent protein coding sequence are excised. Thus, the cells may be selected first by the presence of the green fluorescent protein and then by its absence. The RTSs are exposed to or contacted with a recombinase in any number of ways. By "exposed to" or "contacted with a recombinase that recognizes the RTSs" herein is meant that the recombinase protein must interact with the RTSs in a manner which allows the excision of the sequence between the RTSs. Generally, all that is required is that the recombinase be present within the cell containing the RTSs. This may be done by expressing the recombinase in the cells containing the conditional immortalization construct, as outlined below.

In a preferred embodiment, the expression of the recombinase is transient, since generally the site specific recombination is rapid and efficient. Transient expression is achieved by a variety of methods well known in the art, including, but not limited to, transfection of plasmid DNA by calcium phosphate precipitation, electroporation, lipofection or other physical-chemical methods, transduction using a retroviral vector, or expression from another recombinant viral vector such as an adenovirus. Adenoviral expression is particularly preferred since high expression efficiencies are common.

In an alternate embodiment, the gene encoding the recombinase is placed under the control of an inducible promoter and is part of the immortalization/disimmortalization construct. Generally, an inducible promoter operably linked to the recombinase gene may be included in any of the embodiments depicted in the Figures. Constructs of this type are generally depicted in FIGS. 6 and 3C. FIG. 6A corresponds to FIG. 1C with an inducible promoter/recombinase gene added, which will be left in the genome. FIG. 6B corresponds to FIG. 1C when the recombinase will be excised. Since only a small amount of recombinase is necessary to result in the excision of the sequences between the RTSs, it is desirable to use tightly regulated promoters to avoid premature recombination events. Transcription stop signals flanking the recombinase are also desirable. Recombination and excision of the immortalization gene, and preferably the recombinase gene, occurs as when the appropriate inducing conditions are administered.

In a preferred embodiment, negative selection markers are used, or a combination of positive and negative selection markers. Negative selection markers are particularly useful to prevent immortalized cells from being transplanted. For example, negative selection markers may be expressed with the immortalization gene. After disimmortalization, the cells are exposed to the negative selection agent, such as GANC, which kills any cells which still contain the HSV-tk gene that is closely linked to immortalization gene. Particular examples are shown in FIG. 3. In FIG. 3A, the RTSs flank an immortalization gene and a negative selection gene. As described above, the immortalization gene serves as the first selection marker. Alternatively, clonal colonies which contain the negative selection gene may be identified by using the negative selection marker; that is, clonal colonies are used to identify parent colonies which contain the negative selection gene. The promoter(s) used to drive the expression of the immortalization and negative selection genes may be located on either side of the first RTS. When contacted with a recombinase, the immortalization gene and negative selection gene are excised, and the cell is disimmortalized. Any remaining immortalized cells may be killed by exposing the putatively disimmortalized cells to the negative selection agent; in the case of the herpes simplex virus thymidine kinase gene, for example, the cells may be exposed to GANC. This reduces and potentially eliminates remaining immortalized cells, which is desirable when the cells are transplantation. This construct is particularly preferred since it results in very little if any exogeneous nucleic acid remaining in the genome of the cell, which is also desirable for transplantation. In FIG. 3B, there is a positive selection gene included in the construct to select for immortalized cells. In FIG. 3C, the system is similar to FIG. 3A except that the recombinase under the control of an inducible promoter is included, eliminating the need for further genetic manipulation.

In a preferred embodiment, STOP sites are used to prevent translation of selection markers prior to disimmortalization, as is generally outlined above for a variety of constructs. Alternatively, as depicted in FIG. 5, it is possible to prevent expression of functional selection markers by putting the RTSs in the middle of selection marker genes. This method relies on the faithful excision of the RTSs by the recombinase, since any remaining nucleotides will most likely result in frameshift mutations and thus a non-functional selection marker.

In an additional embodiment, more than one set of RTSs are used. This may be done using additional sets of RTSs which are recognized by the same recombinase, or alternatively, by using RTSs which are recognized by a different recombinase.

When additional sets of RTSs for the same recombinase are used, care should be taken in designing the constructions such that excision between any two RTSs gives a desired or measurable result. That is, since excision can occur between any two RTSs, it is possible that a single RTS, with flanking exogeneous nucleic acid will be left within the genome.

In a preferred embodiment, sets of RTSs from different recombinases are used. This may be of particular use when additional exogeneous genes are included in the genome. For example, using the construct depicted in FIG. 4A, immortalized cells are selected using the first selection marker. For disimmortalization, the recombinase which recognizes the RTS 1 sites is used, and the disimmortalized cells selected using the second selection marker. The exogeneous gene may be transcribed using the first promoter, in which case it will be turned on only upon disimmortalization, or its own promoter, which allows transcription during the immortalized and disimmortalized states. The disimmortalized cells which express the exogeneous protein are transplanted. At some later time, for example when the exogeneous gene product is no longer required, exposure to the second recombinase results in excision of the second selection marker and the exogeneous gene. Alternatively, the exogeneous gene may only be required ex vivo, in which case the second recombinase may be used prior to transplantation. As for the other constructs described herein, those skilled in the art will be able to construct a variety of functionally similar constructs using the teachings herein.

In an additional embodiment, two recombinases are used to eliminate any exogeneous nucleic acid prior to transplantation. For example, using the construct shown in FIG. 4B, immortalized cells are selected using the first selection marker. For disimmortalization, the recombinase which corresponds to the RTS 1 sites is contacted with the construct, and the cells selected on the basis of the second selection marker which is transcribed from the first promoter. The cells can then be contacted with a second recombinase which recognizes the RTS 2 sites prior to transplantation, to eliminate any exogeneous nucleic acid. Although the excision event is very efficient, a loss of the selection marker using clonal colonies may be used for selection.

In one embodiment, the recombination event excises the first selectable marker. This may be preferred in situations where the disimmortalized cells are to be transplanted, and the it is desirable to minimize the introduction of exogenous genes into a patient.

In a preferred embodiment, the first selectable marker is a drug resistance gene such as histidinol dehydrogenase, neomycin-resistance, hygromycin-resistance, and puromycin-resistance, among others. In this embodiment, the second selectable marker is a gene that will allow the sorting or screening of cells, and can include the alkaline phosphatase gene, the gene for green fluorescent protein, the lacZ gene, surface markers such as CD8, or any of the genes outlined for the first selectable marker, as long as the first and second selectable markers are different genes within any single cell. In some embodiments, the transformation frequency may be so high that either the first or the second selectable markers may be eliminated, although generally it is preferable to retain at least the second selectable marker if the disimmortalized cells are destined for transplantation, since it is desirable to ensure that no cells containing oncogenes are transplanted into an animal. In one embodiment, a single selection marker is used, for example a marker such as the green fluorescent protein which allows for cell sorting. In this embodiment, the marker is expressed when the immortalizing gene is introduced, and the transformed cells are separated from the non-transformed cells by cell sorting. Upon disimmortalization, the marker gene is eliminated, and the cells are resorted, with the disimmortalized cells lacking the marker.

In a further embodiment, the immortalized cells are selected on the basis of phenotype. For example, the immortalization gene may serve as the first selectable marker, since cells which do not contain the gene will not grow indefinitely in culture and may be eliminated on this basis. Alternatively, markers may be detected using clonal analysis; for example, when the HSV-TK gene is used, clones may be analyzed for TK activity.

As used herein, the term "genetically-engineered cell" or "recombinant cell" refers to a cell into which foreign (i.e., non-naturally occurring) nucleic acid, e.g., DNA, has been introduced. By "foreign" or "heterologous" or "exogenous" nucleic acid herein is meant nucleic acid which is not normally found within the genome of the cell, or is in a form not normally found within the genome. Thus, immortalization genes such as oncogenes or recombinase target sites may not be normally found in the genome of the host cell, and thus immortalized cells containing these sequences are genetically engineered. In some embodiments, the conditionally immortalized cells are manipulated to express one or more additional exogenous genes. Such genes may be normally contained within the genome, i.e. homologous, but not expressed to an appreciable extent, or are heterologous, i.e. not normally found within the genome. For example, homologous growth factor genes may be introduced to a cell in a form not normally found within the genome; i.e. with regulatory sequences such as promoters which allow expression of the growth factor at levels not normally seen in the cell, or within cell types that do not normally express the growth factor. Alternatively, heterologous genes can be introduced. Thus, the conditionally immortalized cells of the invention may be genetically engineered to contain more than one exogenous nucleic acid sequence.

The conditional immortalization constructs and method of the invention may also contain additional exogenous genes. For example, genes encoding growth factors may be introduced to facilitate the survival of transplanted cells, or for the treatment of the patient. For example, neurotrophins including nerve growth factor (NGF), neurotrophin-3 (NT3), neurotrophin-4 (NT4), and brain-derived neurotrophin factor (BDNF) may be useful. In the case where cells other than neural cells are used, appropriate exogenous genes include those encoding growth factors, such as human growth factor, epidermal growth factor, neural growth factors, etc.; cytokines; enzymes and enzyme inhibitors; interferons, such as α, β or γ-interferons; and other proteins.

Thus for example, cells may be immortalized for ex vivo manipulations such as the introduction of foreign DNA encoding therapeutic agents, and then disimmortalized, allowing the introduction into a patient of genetically engineered cells which express a therapeutic agent.

In one embodiment, the cells are removed from a patient with a genetic defect and engineered to contain at least one copy of a corrected gene before reintroduction of the cells using the techniques of the invention. Genetic disorders which may be treated in this manner are known in the art.

In addition to the immortalization gene, the cells of the invention have additional exogenous nucleic acid, as is more fully described below. This exogenous nucleic acid includes at least two recombinase target sites, and preferably selection and/or marker genes, transcription termination sites, linker sequences, and other genes of interest as described above.

The foreign nucleic acid or exogenous nucleic acid may be introduced by a variety of techniques known in the art, including, but not limited to, calcium-phosphate-mediated transfection, DEAE-mediated transfection, microinjection, retroviral transformation, protoplast fusion and lipofection.

In a preferred embodiment, foreign DNA is introduced into cells using the technique of retroviral transfection. Recombinant retroviruses are used to introduce immortalization genes, selection or marker genes, recombinase target sites, and recombinases. The recombinant retroviruses are produced in packaging cell lines to produce culture supernatants having a high titer of virus particles (generally $10^5$ to $10^6$ pfu/ml). The recombinant viral particles are used to infect cultures of the cells or their progeny by incubating the cell cultures with medium containing the viral particles as is known in the art. Following retroviral infection, the cells are rinsed and cultured in standard medium. The infected cells are then analyzed for the uptake and expression of the foreign DNA. The cells may be subjected to selective conditions which select for cells that have taken up and expressed a selectable marker gene.

In a preferred embodiment, the cloning vector is a retroviral vector, and utilize long terminal repeats (LTR) as shown in the figures. Alternative embodiments utilize traditional expression plasmids, herpes virus-based vectors and adenovirus-based vectors, as well as other equivalents well known to those skilled in the art.

In another embodiment, the foreign DNA is introduced using the technique of calcium-phosphate-mediated transfection as is known in the art. For example, a calcium-phosphate precipitate containing the conditional immortalization constructs of the invention is prepared using the technique of Wigler et al. (1979) Proc. Natl. Acad. Sci. USA 76:1373–1376. Cultures of the cells are established in tissue culture dishes. Twenty four hours after plating the cells, the calcium phosphate precipitate containing approximately 20 µg/ml of the foreign DNA is added. The cells are incubated at room temperature for 20 minutes. Tissue culture medium containing 30 µM chloroquine is added and the cells are incubated overnight at 37° C. Following transfection, the cells are analyzed for the uptake and expression of the foreign DNA. The cells may be subjected to selection conditions which select for cells that have taken up and expressed a selectable marker gene.

The above techniques may be performed more than once on a particular cell; for example, these techniques may be used to introduce the immortalization gene with recombinase sites, and then to introduce further exogenous nucleic acid to the immortalized cells, such as any expression plasmid encoding a recombinase.

As will be appreciated by those in the art, a wide variety of suitable promoters may be used in the invention. Particularly useful promoters include, but are not limited to, the internal promoter enhancer of the LTR of retroviruses, the SV40 promoter, and tissue- or cell-type specific promoters, especially promoters specific for the cell type which is to be conditionally immortalized.

The following is presented by way of example and is not to be construed as a limitation on the scope of the invention. Further, all references referred to herein are expressly incorporated by reference.

EXAMPLE 1

Preparation of Neural Crest Cells

For a given preparation 5–10 timed pregnant female Sprague-Dawley rats (Simonson Laboratories, Gilroy, Calif.) were killed by $CO_2$ asphyxiation. Embryos were removed and placed into Hank's Balanced Salt Solution (HBSS) (Gibco, Grand Island, N.Y.) at 4° C. for 2–4 hours. Under a dissecting microscope, at room temperature, a block of tissue from a region corresponding to approximately the caudal most 10 somites was dissected from each embryo using an L-shaped electrolytically sharpened tungsten needle. Trunk sections were transferred in HBSS into one well of a 3 well depression slid e that had been chilled to 4° C. Trunk sections were treated with collagenase (152 units/mg) (Worthington Biochemical, Freehold, N.J.) made to a concentration of 0.75 mg/ml in Howard's Ringer's solution (per 1 liter of $dH_2O$: NaCl 7.2 g; $CaCl_2$ 0.17 g; KCl 0.37 g) and sterilized, by passage through a 0.22 µm filter prior to use. The collagenase solution was exchanged at least 3 times and with each exchange the trunk sections were vigorously triturated by passage through a pasteur pipet. After incubation at 37° C. for 20 minutes in humidified $CO_2$ atmosphere, the trunk sections were triturated very gently until most of the neural tubes were free and clean of somites and notochords. The collagenase solution was quenched by repeated exchanges with cold complete medium (described below). The neural tubes were plated onto fibronectin-coated (substrate preparation is described below) 60mm tissue culture dishes (Corning, Corning, N.Y.) that had been rinsed with complete medium. After a 30 minute incubation to allow the neural tubes to attach, dishes were flooded with 5 ml of medium. After a 24 hour culture period, using an L-shaped electrolytically sharpened tungsten needle and an inverted phase contrast microscope equipped with a 4X objective lens, each neural tube was carefully scraped away from the neural crest cells that had migrated onto the substrate. Crest cells were removed by a 2 minute 37° C. treatment with 0.05% Trypsin solution (Gibco). The cells were centrifuged for 4 minutes at 2000 r.p.m. and the pellet was resuspended into 1 ml of fresh complete medium. Typically the cells were plated at a density of 225 cells/100 mm dish.

Substrate Preparation

A. Fibronectin (FN) Substrate

Tissue culture dishes were coated with human plasma fibronectin (New York Blood Center, New York, N.Y.) in the following way. Lyophilized fibronectin was resuspended in sterile distilled water ($dH_2O$) to a concentration of 10 mg/ml and stored at −80° C. until used. The fibronectin stock was diluted to a concentration of 250 mg/ml in Dulbecco's phosphate buffered saline (D-PBS) (Gibco). The fibronectin solution was then applied to tissue culture dishes and immediately withdrawn.

B. Poly-D-Lysine (PDL) and FN Substrate

Sterile poly-D-Lysine (PDL) was dissolved in $dH_2O$ to as concentration of 0.5 mg/ml. The PDL solution was applied to tissue culture plates and immediately withdrawn. The plates were allowed to dry at room temperature, rinsed with 5 ml of $dH_2O$ and allowed to dry again. Fibronectin was then applied, as described above, over the PDL.

EXAMPLE 2

Development of a Defined Medium for the Growth of Rat Neural Crest Stem Cells

A serum-free, chemically defined basal medium was developed based on the formulations of several existing defined media. This basal medium consists of L15-$CO_2$ formulated as described by Hawrot, E. et al. (1979) *Methods in Enzymology* 58:574–583 supplemented with additives described by Bottenstein, J. E. et al. (1979) *Proc. Natl. Acad. Sci. USA* 76:514–517 and further supplemented with the additives described by Sieber-Blum, M. et al. (1985) *Exp. Cell Res.* 158:267–272. The final recipe is given here: to L15-$CO_2$ add, 100 µg/ml transferrin (Calbiochem, San Diego, Calif.), 5 µg/ml insulin (Sigma, St. Louis, Mo.), 16 µg/ml putrescine (Sigma), 20 nM progesterone (Sigma), 30 nM selenious acid (Sigma), 1 mg/ml bovine serum albumin, crystallized (Gibco), 39 pg/ml dexamethasone (Sigma), 35 ng/ml retinoic acid (Sigma), 5 µg/ml α-d, 1-tocopherol (Sigma), 63 µg/ml p-hydroxybuyrate (Sigma), 25 ng/ml cobalt chloride (Sigma), 1 µg/ml biotin (Sigma), 10 ng/ml oleic acid (Sigma), 3.6 mg/ml glycerol, 100 ng/ml α-melanocyte stimulating hormone (Sigma), 10 ng/ml prostaglandin El (Sigma), 67.5 ng/ml triiodothyronine (Aldrich Chemical Company, Milwaukee, Wis.), 100 ng/ml epidermal growth factor (Upstate Biotechnology, Inc., Lake Placid, N.Y.), 4 ng/ml bFGF (UBI), and 20 ng/ml 2.55 NGF (UBI).

To allow the growth and regeneration of neural crest stem cells in feeder cell-independent cultures, it was necessary to supplement the basal medium with 10% chick embryo extract (CEE). This supplemented medium is termed complete medium.

CEE is prepared as follows: chicken eggs were incubated for 11 days at 38° C. in a humidified atmosphere. Eggs were washed and the embryos were removed, and placed into a petri dish containing sterile Minimal Essential Medium (MEM with Glutamine and Earle's salts) (Gibco) at 4° C. Approximately 10 embryos each were macerated by passage through a 30 ml syringe into a 50 ml test tube (Corning). This typically produced 25 ml of volume. To each 25 ml was added 25 ml of MEM. The tubes were rocked at 4° C. for 1 hour. Sterile hyaluronidase (1 mg/25 g of embryo) (Sigma) was added and the mixture was centrifuged for 6 hours at 30,000 g. The supernatant was collected, passed first through a 0.45 µm filter, then through a 0.22 µm filter and stored at −80° C. until used.

At the low cell densities necessary for survival and proliferation of individual neural crest cells, either fetal calf serum (FCS, JR Scientific) or CEE was required, in addition to the basal medium, for clone formation. When FCS was used to supplement the medium, it was heat inactivated by treatment at 55° C. for 30 minutes. FCS was stored at −20° C. and passed through a 0.22 µm filter prior to use.

CEE is preferred as a supplement, as in the presence of FCS, most of the cells derived from the neural crest exhibit a flattened, fibroblastic morphology and expression of LNGFR is extinguished. In the absence of both FCS and CEE, clone formation from neural crest cells was greatly attenuated.

EXAMPLE 3

Isolation and Cloning of Multipotent Rat Neural Crest Cells

A. Identification of Antibody Markers Expressed by Neural Crest Cells

In order to identify and isolate rat neural crest cells, it was necessary to identify antibody markers that could be used to recognize these cells. When E10.5 neural tubes were explanted onto a fibronectin (FN) substratum, many of the neural crest cells that emigrated from the neural tubes over the next 24 hours expressed the low-affinity NGF receptor (LNGFR), recognized by monoclonal antibodies 192-Ig and 217c. The outgrowth of neural crest cells from the dorsal side of the explanted neural tube following 24 hours growth in culture is shown in FIG. 1, panel A. FIG. 1, panel B shows the expression of LNGFR (green florescence) and nest in (red fluorescence) in neural crest cells.

Neural crest cells were labeled with antibodies as follows: For cell surface antigens, such as LNGFR, it was possible to label the living cells in culture. The cultures were incubated with primary antibody solution for 20 minutes at room temperature. The cultures were washed twice with L15 medium (Gibco) supplemented with 1:1:2, fresh vitamin mix (FVM) (Hawrot, E. et al. (1979), ibid), and 1 mg/ml bovine serum albumin (L15 Air). The cultures were then incubated for 20 minutes at room temperature with Phycoerythrin R conjugated secondary antibody (TAGO) at a dilution of 1:200 in L-15 Air. The cultures were then rinsed twice with L-15 Air and placed back in their original medium and examined with a fluorescence microscope. Rabbit anti-LNGFR antiserum (Weskamp, G. et al. (1991) Neuron 6:649–663) was a kind gift of Gisela Weskamp, University of California, San Francisco and was used at a 1:1000 dilution. Monoclonal anti-NCAM antibody 5A5 (Dodd, J. et al. (1988) Neuron 1:105–116) and monoclonal anti-sulfatide antibody $O_4$ (Sommer, I. et al. (1981) Dev. Biol. 83:311–327) were obtained as hybridoma cells from the Developmental Studies Hybridoma Bank (Johns Hopkins University, Baltimore, Md.) and prepared as described by the provider.

In order to label cells with antibodies directed against intracellular proteins, it was necessary to fix and permeabilize the cells prior to labeling. For most of the immunocytochemistry, formaldehyde fixation was done. Formaldehyde solution 37% was diluted 1:10 into S-MEM with 1 mM HEPES buffer (Gibco). Culture were treated for 10 minutes at room temperature with the 3.7% formaldehyde solution and then rinsed 3 times with D-PBS (Gibco).

For some intermediate filament proteins (NF and GFAP) formaldehyde fixation was not possible. Cultures were fixed by treatment with a solution of 95% ethanol and 5% glacial acetic acid at $-20°$ C. for 20 minutes.

For the staining of cytoplasmic antigens, fixed cells were first treated with a blocking solution comprising D-PBS, 0.1% Tween-20 (Bio-Rad Laboratories, Richmond, Calif.) and 10% heat inactivated normal goat serum (NGS) for 15 minutes at room temperature. Primary antibodies were diluted with a solution of D-PBS, 0.1% Tween-20 and 5% NGS. The fixed cells were incubated overnight at $4°$ C. in primary antibody solution then rinsed twice with DPBS, 0.05% Tween-20. Fluorescent secondary antibodies were diluted with D-PBS, 1% NGS and applied to cells for 1 hour at room temperature. The cells were rinsed twice with D-PBS, 0.05% Tween-20. To prevent photobleaching, a solution of 8 mg/ml N-propyl gallate in glycerol was placed over the stained cells prior to fluorescence microscopy.

Mouse monoclonal anti-GFAP, G-A-5 (Debus et al. (1983) Differentiation 25:193–203) was purchased from Sigma and used at a 1:100 dilution. Mouse monoclonal anti-NF200, SMI39 was purchased from Sternberger Monoclonals Inc., Baltimore, Md. and used at a 1:100 dilution. SMI39 reactivity is equivalent to the 06-53 monoclonal antibody described by Stemberger, L. A. et al. (1983) Proc. Natl. Acad. Sci. USA 80:6126–6130. Purified rabbit antibodies to peripherin (preparation 199-6) was obtained from Dr. Linda Parysek, University of Cincinnati, Ohio and was used at a dilution of 1:500.

Flow-cytometric analysis indicated that greater than 70% of the neural crest cells show some LNGFR immunoreactivity (FIG. 1, panel D). Approximately 25% of the neural crest cells expressed high levels of LNGFR. In some experiments, neural crest cells expressing high levels of LNGFR were further purified by labeling with 192-Ig (anti-LNGFR) and fluorescence-activated cell sorting (FACS). For single cell analysis, however, it proved more convenient to plate the bulk neural crest cell population at clonal density, and then subsequently identify LNGFR-positive cells by live cell-labeling with 192-Ig.

Most or all of the neural crest cells also expressed nestin, an intermediate filament protein found in CNS neuroepithelial cells. An individual neural crest cell co-expressing both nestin and LNGFR is shown in FIG. 2, panels A–C. Panel A shows the individual neural crest cell in phase contrast. Panels B and C show this cell following staining with both anti-LNGFR (panel B) and anti-nestin (panel C). FIG. 2, panels D–F show that the clonal progeny of this nestin$^+$, LNGFR$^+$ neural crest cell also co-express nestin and LNGFR.

B. Cloning of Multipotent Neural Crest Cells

To define the developmental potential of individual neural crest cells, conditions were established that permit the growth of these cells in clonal culture. FIG. 3 provides a flow chart depicting the following cell cloning experiments. In FIG. 3, plating medium refers to the complete medium, described above and differentiation medium refers to SCD medium, described below. Using an FCS-free, CEE-containing medium (complete or plating medium), single neural crest cells (FIG. 4, panel A, phase contrast and panel B, LNGFR staining) were plated on a FN/PDL substratum and allowed to proliferate and differentiate. After 9-14 days, many of the clones founded by single neural crest cells were large and contained cells with a neuronal morphology (FIG. 4, panel C, phase contrast). Quantification indicated that >60% of the clones contained a mixture of neuronal and non-neuronal cells (see below). These neuronal cells could be labeled by antibodies to pan-neuronal markers such as neurofilament (FIG. 4, panel E, anti-NF160 staining) and high-polysialyic acid (PSA) NCAM (FIG. 4, panel D, anti-NCAM staining), as well as by an antibody to peripherin, an intermediate filament protein that is preferentially expressed by peripheral nervous system (PNS) neurons (FIG. 4, panel F). Importantly, these neurons did not express either nestin or LNGFR, indicating that they have lost the two markers that characterize the undifferentiated neural crest cell.

The neuron-containing clones also contained non-neuronal cells. These cells continued to express LNGFR and nestin, in contrast to the neurons, and displayed an elongated morphology characteristic of Schwann cells. While immature Schwann cells are known to express both LNGFR and nestin, these markers are insufficient to identify Schwann cells in this system since they are expressed by the neural crest precursor cell as well. Expression of more definitive Schwann cell markers was elicited by transferring the cells into a medium known to enhance Schwann cell differentiation. This medium, called Schwann cell differentiation (SCD) medium, contained both 10% FCS and 5 $\mu$M forskolin, an activator of adenylate cyclase.

FIG. 5 shows the expression of a Schwann cell phenotype by neural crest-derived glia. Clones plated initially on FN were allowed to grow for a week in complete medium, then transferred into SCD medium and allowed to grow for another 1–2 weeks prior to fixation and immunocytochemistry. Cells of two morphologies, one elongated and the other flattened can be seen in phase contrast (Panels A and D). To demonstrate concordant expression of three markers, LNGFR, $O_4$ and GFAP, two different double-labeling experiments were performed. Living cells were surface-labeled with monoclonal anti-LNGFR 192IgG (Panel B) and monoclonal $O_4$ IgM (Panel C) and postfixed. In parallel, other cells from the same clone were first surface-labeled with $O_4$ and then fixed with acid-ethanol, permeabilized and stained with anti-GFAP (IgG). Note that LNGFR$^+$ cells (Panel B) are $O_4^+$ and that most or all of the $O_4^+$ cells are also GFAP$^+$ (Panels E and F). The quality of the $O_4$ staining in (Panel E) appears different from that in (Panel C) because a redistribution of the antigen occurs following acid-ethanol fixation. In Panel C, the flattened $O_4^+$ cells are more weakly stained for LNGFR (Panel B). Such flattening is indicative of myelination, and is consistent with the fact that Schwann cells undergoing myelination down-regulate LNGFR and up-regulate $O_4$.

Following 5–10 days in SCD medium, most or all of the non-neuronal cells in the clones expressed glial fibrillary acidic protein (GFAP), an intermediate filament specific to glial cells, and sulfatide, a cell-surface glycolipid recognized by the monoclonal antibody $O_4$. Triple-labeling of such "mature" clones with polyclonal anti-peripherin and monoclonal $O_4$ and anti-GFAP antibodies revealed that sulfatide and GFAP were not expressed by the peripherin-positive neurons and that these two glial markers were coincident in the non-neuronal cell population (FIG. 6). FIG. 6 shows a clone from a single founder cell in phase contrast (Panel A) which expresses LNGFR (Panel B). This clone was allowed to proliferate and differentiate in complete medium (containing CEE and lacking serum) and then transferred into SCD medium (containing serum and forskol in). After approximately 10 days, the culture was fixed and triple-labeled with rabbit anti-peripherin (Panels C and D, in green/yellow), anti-GFAP (IgG) (Panel C, in red) and $O_4$ (IgM) (Panel D, blue). Panels C and D are two separate fields from the same clone.

Although GFAP is expressed by astrocytes and sulfatide is expressed by oligodendrocytes in the CNS, the co-expression of these two markers in the same cell is unique to peripheral glial cells (Jessen, K. R. et al. (1990) *Devel.* 109:91–103 and Mirsky, R. et al. (1990) *Devel.* 109:105–116).

Therefore, these data indicate that single neural crest cells expressing nestin and LNGFR are able to give rise to clones of differentiated cells containing both peripheral neurons and glia. Differentiation to the neuronal phenotype involves both the loss of LNGFR and nestin expression, and the gain of neuronal markers such as neurofilament, high PSA-NCAM and peripherin. On the other hand, in the glial lineage LNGFR and nestin expression persist, and additional glial markers (GFAP and $O_4$) are acquired. All clones that produced neurons and glia also produced at least one other cell type that did not express any of the differentiation markers tested; the identity of these cells is unknown. Taken together, these data establish the multipotency of the rat neural crest cell identified and isolated by virtue of co-expression of LNGFR and nestin.

EXAMPLE 4

Self-renewal of Multipotent Neural Crest Cells in vitro

After 10 days in culture in medium supplemented with 10% CEE and on a FN/PDL substrate, all of the neural crest cell clones that contained neurons also contained non-neuronal cells expressing LNGFR and nestin (as described above). In order to determine whether these cells were immature glia, or multipotent neural crest cells that had undergone self-renewal, serial subcloning experiments were performed. FIG. 7 provides a flow chart summarizing these serial subcloning experiments. In FIG. 7, "plating medium" refers to complete medium containing CEE and lacking FCS and "differentiation medium" refers to SCD medium containing FCS and forskolin.

For serial sub-cloning experiments, clones were harvested and replated as follows. The primary clones were examined microscopically to ensure that there were no impinging colonies and that the whole clone fits within the inscribed circle. Using sterile technique throughout the procedure, glass cloning cylinders (3mm id.) were coated on one end with silicone grease (Dow Corning) and placed about the primary clone so that the grease formed a seal through which medium could not pass. The cells were removed from the cylinder by first treating them with 100 ml of 0.05% Trypsin solution (Gibco) for 3 minutes at 37° C. in a humidified 5% $CO_2$ incubator. At room temperature 70 μl of the trypsin solution was removed and replaced with 70 μl of complete medium. The cells were resuspended into the 100 μl volume by vigorous trituration through a pipet tip and the whole volume was diluted into 5 ml of complete medium. The 5 ml was then plated onto 1 or 2 60mm dishes which were placed in a humidified 5% $CO_2$ incubator for 2 hours at which time the medium was exchanged for fresh complete medium. Single founders cells were then identified and allowed to grow into secondary clones as described below.

Primary clones founded by LNGFR-positive progenitor cells were allowed to grow for 6 days (FIG. 8, Panel A) on a PDL/FN substrate. At this time, clones containing LNGFR-positive cells were identified by live cell surface labeling, and these clones were then removed from their original plates by trypsinization, as described above. The dissociated cells were then replated at clonal density under the same culture conditions as their founder cells. Individual secondary founder cells were identified by labeling live cells with 192-Ig and their positions marked (FIG. 8, Panels B and B' show two individual secondary founder cells; Panels C and C' show the clonal progeny of these individual cells at day 17). Both non-neuronal, neurite bearing cells are visible in the clones (FIG. 8, panels C and C').

A clone derived from secondary founder cells, such as that shown in FIG. 8, was transferred into SCD medium to allow the expression of Schwann cell markers. After approximately 10 days, the subclone was fixed, and double-labeled for NF160 and GFAP (FIG. 9, Panel A shows the clone in phase contrast; Panel B shows labeling with anti-NF160; Panel C shows labeling with anti-GFAP). The apparent labeling of neurons in panel C is an artifact due to bleed-through into the fluorescein channel of the Texas Red fluorochrome used on the goat anti-rabbit secondary antibody in panel B.

Additionally, following 10 days of secondary culture, living subclones were scored visually for the presence of neurons and glia by double labeling with 192-Ig (anti-LNGFR) and 5A5, a monoclonal antibody to high PSAN-CAM.

Single neural crest cells isolated from primary clones were able to proliferate and generate clones containing both neurons and non-neuronal cells, probably glia. Quantitative analysis of clones derived from 16 different primary and 151 secondary founders after ten days in plating medium indicated that over 30% of the total secondary founder cells gave rise to clones containing neurons (N), glia (G) and other (O) cells (Table I, N+G+O). Of the remaining 70% of the founder cells, however, almost 50% failed to form clones and died; thus of the clonogenic (i.e., surviving) founders, 54% were of the N+G+O type (Table I). To confirm that these mixed clones indeed contained glia or glial progenitors, they were transferred to SCD medium and allowed to develop for an additional 7 days, then fixed and double-stained for neurofilament and GFAP expression. As was the case for the primary clones, this treatment caused expression of GFAP in a high proportion of non-neuronal cells in the clones (FIG. 9), confirming the presence of glia. These data indicate that primary neural crest cells are able to give rise at high frequency to progeny cells retaining the multipotency of their progenitors, indicative of self renewal. However, in several cases secondary clones containing only neurons were found (Table I, N only), and many of the secondary clones contained glia and other cells but not neurons (Table I, G+O). This observation suggests that in addition to self-renewal, proliferating neural crest cells may undergo lineage restriction in vitro as well to give rise to glial or neuronal progenitor cells which are characterized by the capacity to divide and self-renew but are restricted to either the neuronal or glial lineage.

TABLE I

Sub-Clone Phenotype total # (%)

| Primary Clone ID | # of 2° Founders | N only | N + G + O | G + O | O | No clone found |
|---|---|---|---|---|---|---|
| 1.1 | 21 | 0 | 15 (71) | 0 | 0 | 6 (29) |
| 1.18 | 6 | 0 | 1 (17) | 1 (17) | 2 (33) | 2 (33) |
| 1.24 | 5 | 1 (20) | 0 | 1 (20) | 2 (40) | 1 (20) |
| 2.6 | 7 | 0 | 0 | 1 (14) | 1 (14) | 5 (72) |
| 2.18 | 7 | 0 | 0 | 1 (14) | 0 | 6 (86) |
| 3.14 | 20 | 0 | 2 (10) | 4 (20) | 0 | 14 (70) |
| 3.18 | 4 | 0 | 1 (25) | 0 | 0 | 3 (75) |
| 4.5 | 1 | 0 | 1 (100) | 0 | 0 | 0 |
| 4.8 | 9 | 0 | 0 | 1 (11) | 2 (22) | 6 (67) |
| 4.14 | 10 | 0 | 2 (20) | 3 (30) | 1 (10) | 4 (40) |
| 5.2 | 15 | 1 (7) | 8 (53) | 0 | 0 | 6 (40) |
| 6.1 | 13 | 0 | 2 (15) | 2 (15) | 0 | 9 (70) |
| 6.2 | 17 | 1 (6) | 2 (12) | 4 (24) | 0 | 10 (58) |
| 6.17 | 2 | 0 | 1 (50) | 0 | 0 | 1 (50) |
| 8.2 | 5 | 0 | 4 (80) | 0 | 0 | 1 (20) |
| 8.5 | 9 | 0 | 4 (44) | 0 | 0 | 5 (56) |
| Mean ± s.e.m. | | | | | | |
| % total founders | 2.1 ± 1.3 | 31 ± 7.9 | 10 ± 2.6 | 7.4 ± 3.3 | 49 ± 6 | |
| % clonogenic founders | 3.1 ± 1.8 | 54 ± 11 | 29 ± 8 | 15 ± 6 | | |

EXAMPLE 5

Substrate Composition Influences the Developmental Fate of Multipotent Neural Crest Cells The foregoing experiments indicate that neural crest cells grown on a PDL/FN substrate generate clones containing both peripheral neurons and glia. When the same cell population is grown at clonal density on a substrate containing FN only, the resulting clones contain glia and "other" cells but never neurons (FIGS. 10 and 11, Panels D,E,F). FIG. 10 provides a flow chart summarizing the following experiments which demonstrate the substrate effect on the fate of mammalian neural crest cells. FIG. 11 shows the immunoreactivity of cells stained for various markers.

On FN alone, G+O clones are obtained containing non-neuronal cells expressing high levels of LNGFR immunoreactivity, but neither NCAM$^+$ nor neurite-bearing cells (FIG. 11, panels E,F). By contrast on PDL/FN, the clones contain both LNGFR$^+$, NCAM$^-$ non-neuronal crest cells and LNGFR$^-$, NCAM$^+$ neurons (FIG. 11, panels B,C). Quantification indicated that on FN alone, 70–80% of the clones are of the G+O phenotype and none of the N+G+O phenotype (FIG. 12, panel A), whereas on PDL/FN 60% of the clones are of the N+C+O and only 20% are of the GAO phenotype (FIG. 12, panel B). These data indicate that the composition of the substrate affects the phenotype of neural crest cells that develop in culture.

To rule out the possibility that the foregoing results could be explained simply by the failure of neurogenic crest cells to adhere and survive on a FN substrate, a different experiment was performed in which all the crest cells were initially cloned on a FN substrate. FIG. 13 provides a flow chart summarizing these experiments. These experiments were performed to demonstrate that differences in attachment and/or survival do not account for differences in eventual clone composition. Subsequently, one group of cells was exposed to PDL as an overlay in liquid media (0.05 mg/ml) after 48 hrs, while a sister culture was retained on FN alone as a control (FIG. 13). Clones expressing LNGFR were identified by live cell surface labeling at the time of the PDL overlay and the development of only LNGFR$^+$ clones was further monitored. After two weeks, the cultures were transferred to SCD medium for an additional 10 days of culture, and their phenotypes then scored as previously described.

By contrast to clones maintained on FN, where no neurons developed, many of the clones exposed to a PDL overlay contained neurons at the end of the culture period (FIG. 14, panel A). Moreover, virtually none of the clones were of the G+O phenotype after the PDL overlay. These data indicate that an overlay of PDL is able to alter the differentiation of neural crest cells even if they are initially plated on an FN substrate. Moreover, they suggest that at least some of the N+G+O clones derived by conversion of founder cells that would have produced G+O clones on FN. However, because of the increased cytotoxicity obtained from the PDL overlay, it was not possible to rule out the possibility that many of the cells that would have produced G+O clones simply died. To address this issue, the PDL overlay was performed on a parallel set of cultures at day 5 rather than at 48 hrs. Under these conditions, virtually all of the LNGFR$^+$ clones survived and differentiated. 60% of these clones contained neurons, whereas 35% contained GAO (FIG. 14, panel B). By contrast, greater than 90% of the clones maintained on FN developed to a G+O phenotype. Since little or no clone death was obtained under these conditions, and since a majority of the clones contained neurons following the PDL overlay at day 5, these data suggest that PDL converts presumptive G+O clones into N+G+O clones. However the fact that 35% of the clones became G+O following PDL overlay at days, whereas virtually none did so when the overlay was performed at 48 hrs (FIG. 14, compare G+O, hatched bars, in panels A and B), suggests that some clones might become resistant to the effect of PDL between 48 hrs and days.

EXAMPLE 6

Substrate Influences Latent Developmental Potential of Neural Crest Cells

To demonstrate more directly that the substrate can alter the developmental fate of neural crest cells, a serial subcloning experiment was performed. Clones were established on FN, and after 5 days the progeny of each clone were subdivided and cloned onto both FN and PDL/FN substrates. Following 10 days of culture in standard medium, the clones were shifted to SCD medium for an additional week to ten days and then fixed, stained and scored for the presence of neurons and Schwann cells. Five of seven primary clones founded on FN gave rise to secondary clones containing neurons when replated onto a PDL/FN substrate at days (Table II). On average, 57±17% of the secondary clones contained neurons. By contrast, none of the sister secondary clones replated onto FN contained neurons (Table II). These data confirm that the PDL/FN substrate is able to alter the fate of neural crest cell clones initially grown on FN. They also reveal that the "neurogenic potential" of neural crest cells is retained, at least for a period of time, on FN even though overt neuronal differentiation is not observed. This suggested that FN is non-permissive for overt neuronal differentiation under these culture conditions. In support of this idea, when primary clones established on PDL/FN were replated onto FN, none of the secondary clones contained neurons, whereas 100% (5/5) of the primary clones gave rise to neuron-containing secondary clones when replated onto PDL/FN (Table II). Moreover, on average 93±7% of the secondary clones derived from each primary clone contained neurons on PDL/ FN, indicating that most or all of the clonogenic secondary crest cells retained neurogenic potential under these conditions.

While this experiment indicated that at least some neural crest clones retain neurogenic potential on FM, not all clones exhibited this capacity. This could indicate a heterogeneity in the clonogenic founder cells that grow on FN, or it could indicate a progressive loss of neurogenic potential with time in culture on FM. To address this issue, a second experiment was performed in which primary clones were replated at day 8 rather than at day 5. In this case, a more dramatic difference was observed between primary clones established on FM versus on PDL/FN. Only 1/6 primary FM clones replated at day 8 gave rise to any secondary clones containing neurons on PDL/FN, and in this one case only 17% of the secondary clones contained neurons (Table II). By contrast, 6/6 primary PDL/FN clones gave rise to neuron-containing secondary clones when replated on PDL/FN at day 8, and 52+7% of these secondary clones contained neurons (Table II). These data suggest that neurogenic potential is gradually lost by neural crest cells cultured on FM, but retained to a much greater extent by the same cells grown on PDL/FN. Thus the composition of the substrate influences not only the overt differentiation of the neural crest cells, but also their ability to maintain a latent developmental potential over multiple cell generations.

TABLE II

| 1° Substrate | FN | | % | pDL/FN | | % |
|---|---|---|---|---|---|---|
| 2° Substrate | FN | pDL/FN | Neuronal | FN | pDL/FN | Neuronal |
| Day 5 Replating | 0/7 | 5/7 | 57 ± 17 | 0/5 | 5/5 | 93 ± 7 |
| Day 8 Replating | 0/6 | 1/6 | 17 | 0/6 | 6/6 | 52 ± 7 |

EXAMPLE 7

Identification of Neural Crest Stem Cells by Transplantation

Neural crest stem cells are identified by two general criteria: by their antigenic phenotype, and by their functional properties. These functional properties may be assessed in culture (in vitro), as described above, or they may be assessed in an animal (in vivo). The above examples described how the self-renewal and differentiation of neural crest stem cells can be assayed in vitro, using clonal cell cultures. However, these properties may also be determined by transplanting neural crest cells into a suitable animal host. Such an assay requires a means of delivering the cells and of identifying the transplanted cells and their progeny so as to distinguish them from cells of the host animal. Using standard techniques, it is possible to deliver neural crest cells to a developing mammalian or avian embryo or to any tissue or compartment of the adult animal (e.g., brain, peritoneal cavity, etc.).

For example, neural crest cell cultures are prepared as described earlier. After a suitable period in primary or secondary culture, neural crest cells are identified by live cell-labeling with antibodies to LNGFR, and removed from the plate using trypsin and a cloning cylinder, as described in previous examples. The cells are diluted into serum-containing medium to inhibit the trypsin, centrifuged and resuspended to a concentration of $10^6$–$10^7$ cells per milliliter. The cells are maintained in a viable state prior to injection by applying them in small drops (ca. 10 $\mu$l each) to a 35 mm petri dish, and evaporation is prevented by overlaying the droplets with light mineral oil. The cells are kept cold by keeping the petri dishes on ice. For injections into mouse embryos, pregnant mothers at embryonic day 8.5–9.0 are anaesthetized and their uterus exposed by an incision into the abdomen. Neural crest cells are drawn into a sharpened glass micropipette (with a sealed tip and hole in the side to prevent clogging during penetration of tissues) by gentle suction. The pipette is inserted into the lower third of the deciduum and a volume of approximately 0.5 $\mu$l is expelled containing approximately 1000 cells. The micropipette is withdrawn and the incision is sutured shut. After an additional 3–4 days, the mother is sacrificed, and individual embryos are removed, fixed and analyzed for the presence and phenotype of cells derived from the injected neural crest cells.

To identify the progeny of the injected cells, it is necessary to have a means of distinguishing them from surrounding cells of the host embryo. This may be done as follows: rat neural crest cells are injected into a mouse embryo (following suitable immunosuppression of the mother or using a genetically immunodeficient strain such as the SCID strain of mice), the injected cells are identified by endogenous markers such as Thy1 or major histocompatibility complex (MHC) antigens using monoclonal antibodies specific for the rat Thy1 or MHC antigens. Alternatively, an exogenous genetic marker is introduced into the cells prior to their transplantation as a means of providing a marker on or in the injected cells. This is as follows: neural crest cells in culture are incubated with a suspension of replication-defective, helper-free retrovirus particles harboring the lacZ gene, at a titer of $10^5$–$10^6$ pfu/ml in the presence of 8 $\mu$l/ml polybrene for four hours. The cells are then washed several times with fresh medium and prepared for injection as described above. The harvested embryos are then assayed for expression of β-galactosidase by whole mount staining according to standard procedures. The blue cells (indicating expression of the lacZ gene) will correspond to the progeny of the injected neural crest cells. This procedure can be applied to any tissue or any stage of development in any animal suitable for transplantation studies. Following whole-mount staining, embryos bearing positive cells are embedded in freezing medium and sectioned at 10–20 $\mu$m on a cryostat. Sections containing blue cells are selected, and then counterstained for markers of mature neurons and glia using specific antibodies, according to standard techniques, and immunoperoxidase or alkalinephosphatase histochemistry. The identification of lacZ+ (blue) cells expressing neuronal or glial markers indicates that the progeny of the injected neural crest cells have differentiated appropriately. Thus, this technique provides a means of identifying mammalian neural crest stem cells through transplantation studies to reveal the function of said stem cells.

EXAMPLE 8

Genetic-Engineering of Neural Crest Stem Cells (NCSCs)

A. Retroviral infection of NCSCs

In this method, NCSCs are infected with a replication-incompetent, recombinant retrovirus harboring the foreign gene of interest. This foreign gene is under the control of the long terminal repeats (LTRs) of the retrovirus, in this case a Moloney Murine Leukemia Virus (MoMuLv) (Cepko et al. (1984) Cell 37:1053–1062). Alternatively, the foreign gene is under the control of a distinct promoter-enhancer contained within the recombinant portion of the virus (i.e., CMV or RSV LTR). In this particular example, the E. coli β-galactosidase gene was used, because it provides a blue histochemical reaction product that can easily be used to identify the genetically-engineered cells, and thereby determine the transformation efficiency.

Rat NCSC cultures were established as described above. Twenty-four hours after replating, the cells were exposed to a suspension of β-galactosidase-containing retrovirus (Turner et al. (1987) Nature 328:131–136) with a titer of approximately $10^5$–$10^6$ pfu/ml in the presence of 8 μg/ml polybrene. Following a 3 hr exposure to the viral suspension, the cultures were rinsed and transferred into standard medium. After three days of growth in this medium, the transformed cells were visualized using the X-gal histochemical reaction (Sanes et al. (1986) EMBO J. 5:3133–3142) FIG. 15, Panel A shows the NCSC culture three days after infection with the lacZ containing retrovirus, after fixation and staining using the X-gal reaction. β-galactosidase-expressing cells are indicated by the solid arrows. Non-expressing cells in the same microscopic field are visualized by phase contrast microscopy (B), and are indicated by open arrows. The blue, β-galactosidase+ cells represented approximately 5–10% of the total cells in the culture as visualized by phase-contrast microscopy (FIG. 15, Panel B).

B. Calcium-Phosphate-Mediated Transfection of NCSCs

In this method, NCSCs are transfected with an expression plasmid using the calcium phosphate method (Wigler et al. (1979) Proc. Natl. Acad. Sci. USA 76:1373–1376). As in the previous example, the β-galactosidase gene was used to facilitate visualization of the transfected cells.

In this case, the vector pRSVlacZ was used, in which the β-galactosidase gene (lacZ) is under the control of the Rous Sarcoma Virus (RSV) LTR, and the SV40 intron and poly A-addition site are provided at the 3' end of the gene (Johnson et al. (1992) Proc. Natl. Acad. Sci. USA 89:3596–3600).

NCSCs were established in 35 mm tissue culture dishes. 24 hr after plating, a calcium phosphate precipitate containing approximately 20 μg/ml of pRSVlacZ was prepared. 123 μl of this precipitate was added to each dish, and incubated at room temperature for 20 minutes. Two ml of standard medium containing 30 μM chloroquine was then added to each dish and incubation was continued overnight at 37° C. The next day, the medium was replaced and incubation continued for a further two days. The cultures were then fixed and assayed for β-galactosidase expression by the standard X-gal reaction. Approximately 10% of the NCSCs expressed the lacZ reaction product.

C. Immortalization of NCSCs

NCSC cultures are established as described above. The cultures are exposed, in the presence of 8 μg/ml polybrene, to a suspension of retrovirus harboring an oncogene preferably selected from the immortalizing oncogenes identified herein. These retroviruses contain, in addition to the oncogene sequences, a gene encoding a selectable marker, such as hisD, driven by the SV40 early promoter-enhancer (Stockschlaeder, M. A. R. et al. (1991) Human Gene Therapy 2:33). Cells which have taken up the hisD gene are selected for by growth in the presence of L-histidinol at a concentration of 4 mM. Alternatively, selection can be based upon growth in the presence of neomycin (500 μg/ml). NCSCs are infected with the above retroviruses which are concentrated to a titer of greater than $10^6$ pfu/ml by centrifugation. The virus is applied to the cells in two sequential incubations of 4–8 hours each in the presence of 8 μg/ml polybrene.

Following infection, the cells are grown in the presence of 4 mM L-histinol or 500 μg/ml neomycin (G418) for 5–10 days. Cells which survive the selection process are screened for expression of LNGFR by live-cell labeling using the monoclonal antibody 192 Ig as described above. Colonies containing a homogeneous population of LNGFR+ cells are cloned using a cloning cylinder and mild trypsinization, and transferred into duplicate FN/pDL-coated 96-well plates. After a short period of growth, one of the plates is directly frozen (Ramirez-Solis, R. et al. (1992) Meth. Enzymol., in press). The cells in the other plate are replated onto several replicate 96-well plates, one of which is maintained for carrying the lines. The cells on the other plates are fixed and analyzed for the expression of antigenic markers. Successful immortalization is indicated by (1) the cells homogeneously maintain an antigenic phenotype characterized by LNGFR+, nestin+, lin− (where "lin" refers to lineage markers characteristic of differentiated neuronal or glial crest derivatives, including neurofilament, peripherin, hi PSA-NCAM, GFAP, O4 and $P_o$); and (2) the cell population is phenotypically stable over several weeks of passage (as defined by lack of differentiation to morphologically- and antigenically-recognizable neurons and/or glia). The ability of the lines to differentiate is tested by transferring them to conditions that promote differentiation (omission of CEE in the case of neurons and addition of serum and 5 μM forskolin for Schwann cells). Maintenance of the ability to differentiate is a desirable, although not necessary, property of the constitutively-immortalized cells.

EXAMPLE 9

Generation of Monoclonal Antibody to Mouse LNGFR

Mouse monoclonal antibodies specific to LNGFR from primates (Loy et al. (1990), J. Neruosci. Res. 27:657–664) and rat (Chandler et al. (1984) J. Biol. Chem. 259:6882–6889) have been produced. No monoclonal antibodies to mouse LNGFR have been described. We have produced rat monoclonal antibodies to mouse LNGFR. These antibodies recognize epitopes present on the surface of living cells such as Schwann cells, making them suitable for use in immunologic isolation of multipotent neural stem cells (such as neural crest stem cells) and their differentiated derivatives (as well as neural progenitor cells from the CNS) from murine species. The isolation of such cells from mice is particularly desirable, as that species is the experimental organism of choice for genetic and immunological studies or human disease.

To generate monoclonal antibodies to mouse LNGFR, a genomic DNA fragment encoding the extracellular domain (ligand binding domain) of that protein was expressed in $E.$ $coil,$ as a fusion protein with glutathione-S-transferase (Lassar et al. (1989) $Cell$ 58:823–831). Briefly, a probe for the extracellular domain based on either of the known DNA sequences for rat and human LNGFR is used to screen a mouse genomic library. A cloned insert from a positively hybridizing clone is excised and recombined with DNA encoding glutathione with appropriate expression regulation sequences and transfected into $E.$ $coli.$ The fusion protein was affinity-purified on a glutathione-Sepharose column, and injected into rats. Sera obtained from tail bleeds of the rats were screened by surface-labeling of live Schwann cells isolated from mouse sciatic nerve by standard procedures (Brockea et al. (1979) $In$ $Vitro$ 15:773–778. Surface labeling was with labelled goat anti-rat antibody Following a boost, fusions were carried out between the rat spleen cells and mouse myeloma cells. Supernatants from the resulting hybridoma cultures were screened using the live Schwann cell assay. Positive clones were re-tested on NIH 3T3 fibroblasts, a mouse cell line that does not express LNGFR, and were found to be negative. The use of this live cell assay ensures that all antibodies selected are able to recognize LNGFR on the surface of living cells. Moreover the assay is rapid, simple and more efficient than other assays such as ELISA, which require large quantities of purified antigen.

Approximately 17 independent positive hybridoma lines were identified and subcloned. An example of the results obtained with the supernatant from one such line 19 shown in FIG. 16. A culture of mouse sciatic nerve Schwann cells was labeled with one of the rat anti-mouse LNGFR monoclonal antibodies and counterstained with DAPI to reveal the nuclei of 611 cells. The left panel (A) shows that most of the cells are labeled on their surface with the anti-LNGFR antibody (red staining; solid arrows), the right panel (B) reveals all the cell nuclei on the plate, and shows a few cells not labeled by the anti-LNGFR antibody (blue staining; open arrows; compare to left panel). These unlabeled cells most likely represent contaminating fibroblasts which are known not to express LNGFR. These cells provide an internal control which demonstrates the specificity of the labeling obtained with the anti-LNGFR antibody.

EXAMPLE 10

O Cells are Smooth Muscle Cells

To determine whether O cells could be smooth muscle cells, cultures of neural crest cells containing these cells were stained with a monoclonal antibody to smooth muscle actin (SMA), a marker of smooth muscle cells (Skalli et al (1966) $J.$ $Cell$ $Biol.$ 103:2787–2796). The cultures were counter-stained with anti-p75 to identify the neural crest stem cells. The anti-SMA antibody labeled a significant number of cells (FIG. 17B, open arrows), and these cells did not express p75 on their surface and were clearly distinct from the p75-expressing neural crest stem cells (FIG. 17B, closed arrow). However, clonal analysis indicated that both $p75^+$, $SMA^-$cells and $p75^-$, $SMA^+$cells derived from a $p75^+$ neural crest stem cell progenitors (see below).

To establish that individual neural crest stem cells could generate neurons, glia and smooth muscle cells, a clonal analysis was performed. Individual p75+ neural crest stem cells were identified and allowed to develop for two weeks in culture. The resultant clones were then fixed and triply-labeled with antibody to peripherin (to detect neurons), GFAP (to detect glia) and SMA (to detect smooth muscle cells). As shown in FIG. 18, within the same clone it was possible to identify neurons (FIGS. 18A, 18B, arrowhead), glia (FIGS. 18C, open arrows) and smooth muscle cells (FIG. 18C, closed arrow), confirming that the neural crest stem cell is able to generate all three lineages in our culture system.

The foregoing experiments were carried out in standard medium (SM) lacking fetal bovine serum. Previously, we observed that the addition of fetal bovine serum to this medium at early times of culture resulted in the extinction of LNGFR expression. Taken together with the foregoing observation that $SMA^+$ cells are $LNGFR^-$, we asked whether cells grown in SM+fetal bovine serum expressed smooth muscle markers. The results indicate that virtually all cells obtained in SM+fetal bovine serum express high levels of SMA (FIGS. 20A, 20B). To further establish their identity as smooth muscle cells, these cells were also stained with two other markers of smooth muscle: desmin (Lazarides, et al (1978) $Cell$ 14:429–438) and calponin (Gimona et al (1990) FEBS Lett. 274:159–162). The SMA+ cells were also labeled by anti-desmin antibody (FIG. 3C) and by anti-calponin (FIGS. 3A, B). These data confirm that the O cells are indeed smooth muscle cells, and also show that fetal bovine serum contains one or more substances able to drive virtually all neural crest stem cells into the smooth muscle lineage.

Differentiated smooth muscle cells have been isolated and cultured from the vasculature, for example, Chamley-Campbell et al (1990) $Phys.$ $Rev.$ 59:1–61, but previously it has not been possible to obtain the de novo differentiation of such cells from an undifferentiated progenitor. The data presented above identify neural crest stem cells as progenitors of smooth muscle, as well as of neurons and glia, and indicate that they can be induced to differentiate to smooth muscle in culture using fetal bovine serum. Such differentiation occurs at the expense of neuronal and glial differentiation, which does not occur in the present of fetal bovine serum (Stemple et al (1992), Id.). Thus, neural crest stem cells should be useful for identifying smooth muscle differentiation factors present in fetal bovine serum, as well as for identifying other growth, survival or differentiation factors for smooth muscle present in other sources.

EXAMPLE 11

Isolation and Cloning of Multipotent Mouse Neural Crest Cells

Cultures of mouse neural crest cells were performed as described for rat neural crest cells (Stemple et al., supra), with the following modifications. E8.5 day old mouse embryos were used rather than E10.5 day old rat embryos. Trypsin (1%) was used instead of collengenase to dissociate neural tubes. Neural crest cells were replated at 48 hours instead of 24 hours. Dissociation with trypsin EDTA, for clonal analysis and replating, was carried out for a period of two minutes rather than 3 minutes. The FGF concentration of the medium was 0.4 $\mu$g (one tenth the concentration used in rat crest cultures) per 500 ml.

EXAMPLE 12

Immortalization of Multipotent Mouse Neural Crest Stem Cells

Preparation of v-myc retrovirus and retroviral infection

Producer cell lines which expressed v-myc and the neomycin resistant gene were grown in DMEM and 10% FBS as described earlier (Lo et al., 1987). After cells had become confluent the medium was replaced with neural crest medium with 10% CEE. 48 hours after the medium change the viral conditioned medium was collected, filtered through a 0.45 μm filter and stored in aliquots sufficient for one viral infection. Repeated freeze thawing was avoided as that led to a substantial loss in the generation of infected clones. An aliquot of the frozen supernatant was tested for infectivity on fibroblasts though no attempt was made to titrate viral titers.

Neural crest cells were infected with the viral supernatant to which was added polybrene (8 μg/ml) 48 hours after emigration from the neural tube as attempts to infect at an earlier time point led to cell death. The cells were incubated with the virus for a period of four hours. The cells were then placed in neural crest medium for a period of 1 hour to allow them to recover. Cells were then reinfected for a period of 4 hours. In some experiments a third round of infection (4 hours of infection with an hour between infections) was also carried out. One hour after the last round of infection cells were trypsinized and replated at low density (10,000–20,000 cells/ 35 mm dish) for neomycin selection.

E8.5 neural tubes were dissected and plated as described above. Forty hours after plating the neural tubes were scraped away from the emigrated neural crest cells using a sharpened tungsten needle. The crest cells were then infected with a replication incompetent avian-myc virus as described above. 24 hours after infection cells were plated under neomycin selection (500 μg/ml) for a period of 4 days. Neomycin resistant colonies that were immunoreactive for p75 were picked and replated in 96 well dishes. Clones were replated into progressively larger dishes until they were frozen from 60 mm dishes. Clones selected on the basis of their growth rate, maintenance of a crest cell morphology and continued expression of p75 immunoreactivity were tested for their ability to differentiate into neurons and glia. One clone myc-1 was selected for further studies.

EXAMPLE 13

Differentiation of Immortalized Multipotent Mouse Neural Crest Stem Cells

To differentiate the myc-1 cell line, cells were trypsinized and replated onto dishes sequentially coated with poly-d-lysine (1 mg/ml) and fibronectin (0.5 mg/ml) in defined medium (see Stemple et al., 1993, supra). 24 hours after replating, serum (10%) and forskolin (5 μM) were added to the medium. Neuronal and glial differentiation as assayed by differentiation specific markers was seen 2–5 days after adition of serum and forskolin.

What is claimed is:

1. A method for creating an immortalized cell line comprising transforming neural crest stem cells with a vector comprising an immortalizing gene flanked by recombinase target sites to create an immortalized cell line, wherein said neural crest stem cells are capable of self-renewal in a feeder cell-independent culture medium, express low-affinity nerve growth factor receptor (LNGFR) and nestin, but do not express neuronal or glial lineage markers including glial fibrillary acidic protein (GFAP), wherein at least one of said stem cells is capable of differentiation to a peripheral nervous system (PNS) neuronal cell that does not express LNGFR or nestin but does express neurofilament-160, and wherein at least one of said stem cells is capable of differentiation to a PNS glial cell that expresses LNGFR, nestin, and GFAP.

2. A method according to claim 1 wherein said immortalizing gene is selected from the group consisting of v-myc, N-myc, T antigen, Ewing's sarcoma oncogene, bcr-abl, neurofibromin, neu, ret, p53, Rb, and Notch.

3. A method according to claim 2 wherein said immortalizing gene is v-myc.

4. An immortalized cell line made according to the method of claim 1.

5. An immortalized cell line according to claim 4 which contains a selection marker gene.

6. An immortalized cell line according to claim 4 which contains additional exogenous gene encoding a neurotrophic factor.

7. An immortalized mammalian neural crest stem cell line that contains in the genome of said cell line exogenous nucleic acid comprising at least a first and a second recombinase target sites flanking an immortalization gene, wherein said target sites are capable of mediating excision of said immortalization gene when said target sites are contacted with a recombinase, wherein said cell line is made according to the method of claim 1.

8. An immortalized cell line according to claim 7 wherein said exogenous nucleic acid further comprises a selection marker gene.

9. An immortalized cell line according to claim 8 wherein said selection marker gene is a negative selection marker gene.

10. An immortalized cell line according to claim 7 wherein said nucleic acid further comprises a STOP site.

11. An immortalized cell line according to claim 7 wherein said exogenous nucleic acid further comprises a first selection marker gene and a second selection marker gene.

12. A method for creating immortalized neural crest stem cells in vitro that contain recombinase target sites flanking an immortalization gene in the genome of said immortalized cells, said method comprising transforming neural crest stem cells with exogenous nucleic acid comprising:

a) a first recombinase site;

b) an immortalization gene; and c) a second recombinase site;

such that in the absence of a recombinase said exogenous nucleic acid is incorporated into the genome of said cell, wherein said neural crest stem cells are capable of self-renewal in a feeder cell-independent culture medium, express low-affinity nerve growth factor receptor (LNGFR) and nestin, but do not express neuronal or glial lineage markers including glial fibrillary acidic protein (GFAP), wherein at least one of said stem cells is capable of differentiation to a peripheral nervous system (PNS) neuronal cell that does not express LNGFR or nestin but does express neurofilament-160, and wherein at least one of said stem cells is capable of differentiation to a PNS glial cell that expresses LNGFR, nestin and GFAP.

13. A method according to claim 11 wherein said nucleic acid further comprises at least one selection marker gene.

14. A method according to claim 13 wherein said selection marker gene is a negative selection marker.

15. A method for the in vitro disimmortalization of immortalized neural crest stem cells that contain exogenous nucleic acid comprising recombinase target sites flanking an immortalization gene in the genome of said immortalized cells, said method comprising contacting said recombinase target sites with a recombinase capable of recognizing said recombinase target sites, wherein said neural crest stem cells are capable of self-renewal in a feeder cell-independent culture medium, express low-affinity nerve growth factor receptor (LNGFR) and nestin, but do not express neuronal or glial lineage markers including glial fibrillary acidic protein (GFAP), wherein at least one of said stem cells is capable of differentiation to a peripheral nervous system (PNS) neuronal cell that does not express LNGFR or nestin but does express neurofilament-160, and wherein at least one of said stem cells is capable of differentiation to a PNS glial cell that expresses LNGFR, nestin and GFAP.

16. A method according to claim 15 wherein said contacting is achieved by transforming said immortalized cell with a recombinase nucleic acid encoding said recombinase and maintaining said transformed cells under conditions where said recombinase is expressed and said immortalization gene is excised.

17. A method for the in vitro disimmortalization of immortalized neural crest stem cells comprising:
   a) incorporating exogenous nucleic acid comprising:
      i) a first recombinase target site;
      ii) an immortalization gene;
      iii) a negative selection marker gene; and
      iv) a second recombinase target site;
   into the genome of neural crest stem cells to produce immortalized cells which contain an excisable immortalization gene in an orientation such that excision of the sequence between the recombinase target sites excises the immortalization gene and the negative selection marker; and
   b) contacting said recombinase target sites with a recombinase which recognizes said recombinase target sites such that said immortalization gene and said negative selection marker gene are excised,
   wherein said neural crest stem cells are capable of self-renewal in a feeder cell-independent culture medium, express low-affinity nerve growth factor receptor (LNGFR) and nestin, but do not express neuronal or glial lineage markers including glial fibrillary acidic protein (GFAP), wherein at least one of said stem cells is capable of differentiation to a peripheral nervous system (PNS) neuronal cell that does not express LNGFR or nestin but does express neurofilament-160, and wherein at least one of said stem cells is capable of differentiation to a PNS glial cell that expresses LNGFR, nestin and GFAP.

18. A method according to claim 17 wherein said contacting is achieved by transforming said immortalized cells with a vector encoding a recombinase which recognizes said recombinase target sites under conditions wherein said recombinase is expressed.

19. A method according to claim 17 wherein said exogenous nucleic acid further comprises a gene for a recombinase that recognizes said recombinase target sites, wherein said recombinase gene is operably linked to an inducible promoter, and said contacting is achieved by growing said immortalized cells under conditions wherein said recombinase is expressed.

20. A method according to claim 17 wherein said exogenous nucleic acid further comprises a positive selection gene.

21. A method for the in vitro disimmortalization of immortalized neural crest stem cells comprising:
   a) incorporating exogenous nucleic acid comprising:
      i) a first recombinase target site;
      ii) an immortalization gene;
      iii) a selection marker gene; and
      iv) a second recombinase target site;
   into the genome of neural crest stem cells to produce an immortalized cell which contains an excisable immortalization gene in an orientation such that excision of the sequence between the recombinase target sites excises the immortalization gene, resulting in the expression of the selection marker; and
   b) contacting said recombinase target sites with a recombinase which recognizes said recombinase target sites such that said immortalization gene is excised,
   wherein said neural crest stem cells are capable of self-renewal in a feeder cell-independent culture medium, express low-affinity nerve growth factor receptor (LNGFR) and nestin, but do not express neuronal or glial lineage markers including glial fibrillary acidic protein (GFAP), wherein at least one of said stem cells is capable of differentiation to a peripheral nervous system (PNS) neuronal cell that does not express LNGFR or nestin but does express neurofilament-160, and wherein at least one of said stem cells is capable of differentiation to a PNS glial cell that expresses LNGFR, nestin and GFAP.

22. A method according to claim 21 wherein said nucleic acid further comprises a STOP site.

23. A method according to claim 21 wherein said contacting is achieved by transforming said immortalized cells with a vector encoding a recombinase which recognizes said recombinase target sites under conditions wherein said recombinase is expressed.

24. A method according to claim 21 wherein said exogenous nucleic acid further comprises a gene for a recombinase that recognizes said recombinase target sites operably linked to an inducible promoter, and said contacting is achieved by growing said immortalized cells under conditions wherein said recombinase is expressed.

25. A method for the in vitro disimmortalization of immortalized neural crest stem cells comprising:
   a) incorporating exogenous nucleic acid comprising:
      i) a first recombinase target site;
      ii) an immortalization gene;
      iii) a first selection marker gene;
      iv) a second recombinase target site; and
      v) a second selection marker gene;
   into the genome of neural crest stem cells to produce immortalized cells which contain an excisable immortalization gene in an orientation such that when the immortalization gene is expressed, the first selection marker gene is also expressed and the second selection marker gene is not expressed and when said immortalization gene is excised said second selection marker is expressed; and
   b) contacting said recombinase target sites with a recombinase which recognizes said recombinase target sites such that said immortalization gene is excised,
   wherein said neural crest stem cells are capable of self-renewal in a feeder cell-independent culture medium, express low-affinity nerve growth factor receptor (LNGFR) and nestin, but do not express neuronal or glial lineage markers including glial fibrillary acidic protein (GFAP), wherein at least one of said stem cells is capable of differentiation to a peripheral nervous system (PNS) neuronal cell that does not express LNGFR or nestin but does express neurofilament-160, and wherein at least one of said stem cells is capable of differentiation to a PNS glial cell that expresses LNGFR, nestin and GFAP.

* * * * *